United States Patent
Campbell, Jr. et al.

(10) Patent No.: US 6,500,949 B2
(45) Date of Patent: Dec. 31, 2002

(54) BRIDGED METAL COMPLEXES

(75) Inventors: Richard E. Campbell, Jr., Midland, MI (US); Kevin A. Frazier, Midland, MI (US); David D. Devore, Midland, MI (US); Paul C. Vosejpka, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 66 days.

(21) Appl. No.: 09/829,884

(22) Filed: Apr. 10, 2001

(65) Prior Publication Data

US 2001/0025115 A1 Sep. 27, 2001

Related U.S. Application Data

(60) Continuation-in-part of application No. 09/523,428, filed on Mar. 10, 2000, now Pat. No. 6,284,905, which is a division of application No. 09/383,996, filed on Aug. 26, 1999, now abandoned.
(60) Provisional application No. 60/103,511, filed on Oct. 8, 1998.

(51) Int. Cl.$^7$ ............................. C07F 17/00; C07F 7/00; B01J 31/00; C08F 4/64
(52) U.S. Cl. .................. 544/64; 544/225; 548/103; 556/7; 556/27; 556/53; 568/6; 502/103; 502/117; 526/161; 526/943
(58) Field of Search ................ 556/7, 27, 53; 548/103; 544/225, 64; 568/6; 502/103, 117; 526/161, 943

(56) References Cited

U.S. PATENT DOCUMENTS 5,399,636 A   3/1995   Alt et al. .................... 526/129

6,284,905 B1 * 9/2001   Ashe et al. .................... 556/7

FOREIGN PATENT DOCUMENTS

EP   416815     8/1990
WO   98/39369   9/1998

OTHER PUBLICATIONS

*Angew Chem. Int. Ed. Engl.*, vol. 36, No. 21, pp. 2338–2340, 1997.
*Phosphorus, Sulfur, and Silicon*, vol. 124 & 125, pp. 561–565, 1997.
*Chem. Ber.*, vol. 127, pp. 1901–1908, 1994.
*Eur. J. Inorg. Chem.*, pp. 505–509, 1998.
*J. Organomet. Chem.*, vol. 530, pp. 117–120, 1997.
*Organometallics*, vol. 16, pp. 4546–4550, 1997.
Heinrich Noth, et al., Contributions to the Chemistry of Boron, 185; "Reactions of Metal Carbene Complexes with (tert–Butylimino) (2,2,6,6–tetramethylpiperidino)borane", Chem. Ber., vol. 120, No. 5, pp. 863–865, (1987).
Guillermo Bazan, et al., "Aminoboratabenzene Derivatives of Zirconium: A new Class of Olefin Polymerization Catalysts", *J. Am. Chem. Soc.*, vol. 118, No. 9, pp. 2291–2292, (1996).
Chemical Abstracts, vol. 126, No. 26, (1997), Abstract No. 343636.

* cited by examiner

*Primary Examiner*—Porfirio Nazario-Gonzalez

(57) ABSTRACT

An improved process for forming bridged Group 4 transition metal complexes using boron trihalide and a magnesium dicyclopentadienyl compound to form a dicyclopentadienyl boron halide intermediate for subsequent metallation or other synthetic use and novel metal complexes.

11 Claims, No Drawings

BRIDGED METAL COMPLEXES

CROSS-REFERENCE TO RELATED APPLICATION

This application is a continuation-in-part of U.S. Ser. No. 09/523,428, filed Mar. 10, 2000, now U.S. Pat. No. 6,284,905 which is a divisional of U.S. application Ser. No. 09/383,996, filed Aug. 26, 1999, now abandoned which claims benefit of priority from provisional application 60/103511, filed Oct. 8, 1998.

BACKGROUND OF THE INVENTION

This invention relates to certain bridged Group 4 transition metal complexes possessing an unique bridging structure and to olefin polymerization catalysts obtained from such complexes. In another embodiment the invention relates to an unique process for preparing such metal complexes and intermediate compounds used in such synthesis. More particularly, the unique bridge of the foregoing metal complexes consists of amido-substituted boron atoms characterized in that the amido group contains a ligand containing an element from group 15 or 16 of the Periodic Table of the Elements.

In *Angew. Chem. Int. Ed. Engl.*, 36, 21, p2338–2340 (1997) and in *Phosphorus Sulfur, and Silicon*, 124 & 125, p561–565 (1997) amido substituted boron bridged ferrocenophanes useful for forming poly(ferrocenes) by a ring opening polymerization were disclosed. The synthesis and characterization of Group 1 and 2 metal and tin complexes of 1,2-bis(dimethylamino)-1,2-di-9-fluorenyldiboranes were disclosed in *Chem. Ber.*, 127, p1901–1908, (1994). Diboranes having structure similar to those employed in the foregoing study were disclosed by the same researchers in *Eur. J. Inorg. Chem.*, p505–509 (1998). Ferrocenophane derivatives of similar bisboranes for further molecular property studies were disclosed by *J. Organomet. Chem.*, 530 p117–120 (1997). In *Organometallics*, 16, p4546–4550 (1997) boron bridged ansa metallocene complexes including dimethylsulfide and phosphine adducts thereof of possible use in Ziegler-Natta-type olefin polymerizations were disclosed.

In the patent literature, bridged metal complexes for use as olefin polymerization catalyst components, including such complexes containing one or more boron atoms in the bridge are generically disclosed by EP-A-416,815 and WO 98/39369. Certain techniques for preparing boron bridged metallocenes, including the use of deprotonating agents that are weakly nucleophilic bases are disclosed in U.S. Pat. No. 5,962,718.

SUMMARY OF THE INVENTION

The present invention relates to an improved process for forming certain bridged Group 4 transition metal complexes corresponding to the formula:

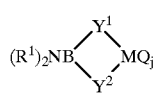

Formula 1 wherein:

M is a Group 4 metal, preferably zirconium, said metal M being in the +2, +3 or +4 formal oxidation state;

$Y^1$ and $Y^2$ are independently anionic, cyclic or non-cyclic, π-bonded groups, Q, independently each occurrence, is a neutral, anionic or dianionic ligand group, said Q having up to 50 atoms not counting hydrogen;

j is an integer from 1 to 4, selected with respect to the oxidation state of M and the electronic nature of Q to provide overall charge balance to the compound;

$R^1$ is independently each occurrence hydrogen, a hydrocarbyl group, a tri(hydrocarbyl)silyl group, or a tri(hydrocarbyl)silylhydrocarbyl group, or one of the foregoing multiatomic groups further substituted with one or more di(hydrocarbyl)amino- or hydrocarbyloxy- groups, said $R^1$ group containing up to 50 atoms not counting hydrogen, and optionally both $R^1$ groups may be joined together, optionally by means of one or more divalent bridging groups derived from the foregoing di(hydrocarbyl)amino- or hydrocarbyloxy- substituent groups, thereby forming a dianionic ligand group, the steps of the process comprising:

(1) contacting a boron trihalide with a magnesium dianionic salt corresponding to the formula $Mg(Y^1H)(Y^2H)$, wherein $Y^1$ and $Y^2$ are as previously defined to prepare a metal complex according to the formula:

Formula 2 wherein X is halide;

(2) aminating the boron bridging atom thereby forming a compound of Formula 3,

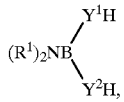

Formula 3 wherein $R^1$ is as previously defined, (3) deprotonating the product of step (2) of Formula 3 by contact with a deprotonating agent; especially a weak nucleophilic base, and (4) contacting the product of step (3) with a transition metal salt of the formula $MY^3{}_y(LB)_b$, wherein M is as previously defined;

$Y^3$ is Q or a leaving group, especially halide, more especially bromide or chloride;

y is an integer from 0 to 4 selected to provide charge balance in the transition metal salt;

LB is a Lewis base compound; and b is an integer from 0 to 3.

According to the present invention there is also provided a process for forming a compound corresponding to the formula:

Formula 2 wherein X is halide, preferably bromide or chloride; and $Y^1$ and $Y^2$ are independently anionic, cyclic or non-cyclic, π-bonded groups, the steps of the process comprising:

(1) contacting a boron trihalide with a magnesium dianionic salt corresponding to the formula $Mg(Y^1H)(Y^2H)$, wherein $Y^1$ and $Y^2$ are as previously defined under reaction conditions to thereby prepare the metal complex of formula 2.

In a final embodiment, the present invention relates to certain novel bridged Group 4 transition metal complexes corresponding to the formula:

Formula 1'

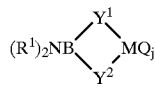

wherein:

M is a Group 4 metal, preferably zirconium, said metal M being in the +2, +3 or +4 formal oxidation state;

$Y^1$ and $Y^2$ are independently anionic, cyclic or non-cyclic, π-bonded groups, Q is a neutral, anionic or dianionic ligand group depending on the oxidation state of M, said Q having up to 50 atoms not counting hydrogen;

j is an integer from 1 to 4, selected with respect to the oxidation state of M and the electronic nature of Q to provide overall charge balance to the compound; and $R^1$ is independently each occurrence is a substituted hydrocarbyl group, a substituted tri(hydrocarbyl)silyl group, or a substituted tri(hydrocarbyl)silylhydrocarbyl group, said group being substituted with one or more di(hydrocarbyl)amino- or hydrocarbyloxy- groups and containing up to 50 atoms not counting hydrogen, and optionally both $R^1$ groups may be joined together, optionally by means of one or more divalent bridging groups derived from the foregoing di(hydrocarbyl)amino- or hydrocarbyloxy- substituent groups, thereby forming a dianionic ligand group.

The metal complexes according to Formula 1 or Formula 1', are usefully employed as components of olefin polymerization catalyst compositions.

DETAILED DESCRIPTION

All references to the Periodic Table of the Elements herein shall refer to the Periodic Table of the Elements, published and copyrighted by CRC Press, Inc., 1997. Also, any references to a Group or Groups shall be to the Groups or Groups reflected in this Periodic Table of the Elements using the IUPAC system for numbering groups. Where any reference is made herein to any publication, patent application or provisional patent application, the contents thereof are incorporated herein in its entirety by reference. By the term "X-bonded" as used herein is meant that bonding occurs through an interaction involving delocalized electrons. By the term, "leaving group" is meant a ligand that is readily displaced by another ligand under ligand exchange conditions.

Suitable Lewis base compounds, LB, in the foregoing reagents and products, include neutral Q groups, especially conjugated dienes, especially 1,4-diphenyl-1,3-butadiene, which are capable of donating an electron pair originating from delocalized π-electrons contained therein.

All of the foregoing process steps are desirably conducted in an inert solvent, especially an aliphatic or aromatic hydrocarbon or ether, employing temperatures from −100° C. to 150° C. Amination of the boron bridging atom (step (2)) may be accomplished by the use of either an alkali metal amide- or Grignard amide- reagent of the formula $MeNR^1_2$, wherein Me is an alkali metal cation or Grignard cation ($MgBr^+$ or $MgCl^+$) (step 2a), or a secondary amine of the formula $HNR^1_2$, preferably in excess, (or a mixture of the foregoing secondary amine reagent and a tertiary amine of the formula, $NR^3_3$), wherein $R^1$ is as previously defined and $R^3$ is $R^1$ or $C_{1-4}$ alkyl (step 2b). By performing the amination after addition of the cyclopentadienyl ligands to the boron bridging group instead of before such addition, the desired product is formed in higher yield and purity. Moreover, use of the foregoing neutral amination conditions of step 2b to prepare the desired product, is not possible, unless steps (1) and (2) are performed in the prescribed order, as disclosed herein.

Step (3) is accomplished by contacting the intermediate compound with the base under deprotonation conditions. Such process conditions are well known in the art. Preferred deprotonation agents are weak, nucleophilic bases, especially an alkalimetal bis(trialkysilyl)amide, most preferably lithium bis(trimethylsilyl)amide. Stronger bases, such as lithium alkyls may be used for the deprotonation step as well, particularly if moderating reaction conditions such as reduced temperatures and/or dilute concentrations of reagents are employed. To form the desired dianionic compound, at least two equivalents of the base are preferably employed.

Suitable transition metal reagents for step (4) of the formula $MY^3_y(LB)_b$, specifically include $ZrCl_4$, $ZrCl_3$, $ZrCl_2$ (1,4-diphenyl-1,3-butadiene), $HfCl_4$, $HfCl_3$, and adducts thereof with one or more Lewis bases selected from ethers, polyethers, amines, or polyamines, said Lewis base having up to 20 carbons, preferably THF. An especially preferred transition metal reagent is a transition metal/diene compound of the formula:

Formula 3

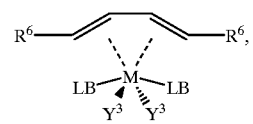

wherein,

M is Ti, Zr or Hf, $Y^3$ is a leaving group, especially halide;

$R^6$ independently each occurrence is hydrogen, a hydrocarbyl group, a tri(hydrocarbyl)silyl group, or a tri(hydrocarbyl)silylhydrocarbyl group, said $R^6$ groups containing up to 20 atoms not counting hydrogen; and LB is a Lewis base, especially an ether, amine, or phosphine of up to 20 carbons.

Use of the foregoing transition metal reagent of formula 3 allows for the preparation of complexes of formula 1 in high racemic purity in the +2 formal oxidation state. Any of the compounds may be raised to a higher oxidation state by contact with an oxidizing agent, preferably a chlorohydrocarbon- or chlorocarbon-compound.

Preferred Group 4 transition metal complexes formed according to the present invention correspond to formula 1a:

formula 1a

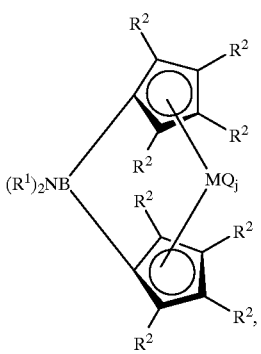

wherein

M, Q, j and $R^1$ are as defined above;

$R^2$ is hydrogen, or a hydrocarbyl, halohydrocarbyl, dihydrocarbylamino-hydrocarbyl, tri(hydrocarbylsilyl) hydrocarbyl, $Si(R^4)_3$, $N(R^4)_2$, or $OR^4$ group of up to 20 carbon or silicon atoms, and optionally two adjacent $R^2$ groups can be joined together, thereby forming a fused ring structure, especially an indenyl ligand or a substituted indenyl ligand, and $R^4$ is independently hydrogen, a hydrocarbyl group, a trihydrocarbylsilyl group or a tri(hydrocarbyl)silylhydrocarbyl group, said $R^4$ having up to 20 atoms not counting hydrogen.

Preferred metal complexes of formula 1' are similarly described as for the preferred complexes of formula 1a, excepting that $R^1$ is as previously defined with respect to formula 1'.

When M is in the +4 oxidation state, j=2 and Q independently each occurrence is halide, hydride, hydrocarbyl, trihydrocarbylsilyl, tri(hydrocarbyl)silylhydrocarbyl, hydrocarbyloxide, dihydrocarbylamide, or hydrocarbyleneamide, said Q having up to 20 atoms not counting hydrogen. Alternatively, two Q groups may be joined together to form a hydrocarbadiyl- or hydrocarbylene-group, especially a dianionic derivative of a conjugated, $C_{4-40}$ diene that together with M forms a metallocyclopentene.

When M is in the +3 oxidation state, j=1 and Q is either 1) a monovalent anionic stabilizing ligand selected from the group consisting of alkyl, cycloalkyl, aryl, silyl, amido, phosphido, alkoxy, aryloxy, sulfido groups, and mixtures thereof, and being further substituted with an amine, phosphine, ether, or thioether containing substituent able to form a coordinate-covalent bond or chelating bond with M said ligand having up to 50 atoms not counting hydrogen; or 2) a $C_{3-10}$ hydrocarbyl group comprising an ethylenic unsaturation able to form an $\eta^3$ bond with M.

When M is in the +2 oxidation state, j=1 and Q is a neutral conjugated diene, optionally substituted with one or more tri(hydrocarbyl)silyl or tri(hydrocarbyl)silylhydrocarbyl groups, said Q having up to 40 carbon atoms and forming a π-complex with M.

Specific examples of the above metal complexes wherein M is in the +4 oxidation state are those of formula 1a or 1', wherein the definitions of M, Z, $R^1$, and $R^2$ are as defined above, j is 2, and wherein Q, independently each occurrence, is a halide, or a hydrocarbyl- or trihydrocarbylsilyl-group of up to 10 atoms not counting hydrogen, or two Q groups together form a divalent derivative of a $C_{4-20}$ diene coordinated to M in a metallocyclopentene fashion. Most highly preferably Q independently each occurrence is chloride or a $C_{1-6}$ hydrocarbyl group, or two Q groups together form a 2-methyl-2-butene-1,4-diyl or 2,3-dimethyl-2-butene-1,4-diyl group.

Specific examples of the above metal complexes wherein M is in the +3 oxidation state are those of formula 1a or 1', wherein the definitions of M, Z, $R^1$, and $R^2$ are as defined above, j is 1, and wherein Q, each occurrence is a monovalent anionic stabilizing ligand selected from the group consisting of aryl and aralkyl groups which are further substituted with one or more amine, aminoalkyl, phosphine, or ether substituents able to form a coordinate-covalent bond or chelating bond with M, said Q having up to 30 non-hydrogen atoms; or Q is a $C_{3-10}$ hydrocarbyl group comprising an ethylenic unsaturation able to form an $\eta^3$ bond with M. Most highly preferred examples of such Q ligands are 2-N,N-dimethylaminobenzyl, allyl, and 1-methylallyl.

Specific examples of the above metal complexes wherein M is in the +2 oxidation state are those of formula 1a or 1', wherein the definitions of M, Z, $R^1$, and $R^2$ are as defined above, j is 1, and wherein Q, each occurrence, is a neutral conjugated diene, optionally substituted with one or more tri(hydrocarbyl)silyl groups or tri(hydrocarbyl)silylhydrocarbyl groups, said Q having up to 30 atoms not counting hydrogen and forming a π-complex with M. Most highly preferred Q groups are 1,4-diphenyl-1,3-butadiene, 1,3-pentadiene, 3-methyl-1,3-pentadiene, 2,4-hexadiene, 1-phenyl-1,3-pentadiene, 1,4-dibenzyl-1,3-butadiene, 1,4-ditolyl-1,3-butadiene, 1,4-bis(trimethylsilyl)-1,3-butadiene, and 1,4-dinaphthyl-1,3-butadiene.

Preferably in the foregoing formulas 1, 1' and 1a, $Y^1$ and $Y^2$ are both cyclopentadienyl, alkyl- or polyalkyl- substituted cyclopentadienyl, inden-1-yl, 2-alkyl-4-arylinden-1-yl, or 3-alkylinden-1-yl, or $Y^1$ is cyclopentadienyl, alkyl- or polyalkyl- substituted cyclopentadienyl and $Y^2$ is fluorenyl; and Q is halide, alkyl, trialkylsilyl, N,N-dialkylamido, or 1,4-diphenyl-1,3-butadiene (said alkyl or aryl groups having up to 10 carbons). Even more preferably in formula 1, 1' and 1a, M is zirconium or hafnium.

Most highly preferred metal complexes of formula 1 are those wherein $Y^1$ and $Y^2$ are both inden-1-yl, 2-methyl-4-phenylinden-1-yl, 2-methyl-4-(2-methylphenyl)inden-1-yl, 3-isopropylinden-1-yl, or 3-t-butylinden-1-yl groups, especially compositions comprising greater than 90 percent rac isomer.

Preferred Group 4 transition metal complexes of formula 1' are those wherein:

$R^1$ each occurrence is 4-dimethylaminophenyl or two $R^1$ groups together with N are an isoindolenino, N-methylpiperazino, or morpholino group, that is,

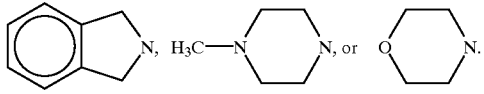

Highly preferred Q groups for the foregoing compounds of formula 1' wherein M is in the +2 formal oxidation state are 1,4-diphenyl-1,3-butadiene, 1,3-pentadiene, 3-methyl-1,3-pentadiene, 2,4-hexadiene, 1-phenyl-1,3-pentadiene, 1,4-dibenzyl-1,3-butadiene, 1,4-ditolyl-1,3-butadiene, 1,4-bis (trimethylsilyl)-1,3-butadiene, and 1,4-dinaphthyl-1,3-butadiene. Highly preferred Q groups for the foregoing compounds of formula 1' wherein M is in the +3 formal oxidation state are 2-(N,N-dimethylamino)benzyl, 2-(N,N-dimethylaminomethyl)phenyl, and allyl. Highly preferred Q groups for the foregoing compounds of formula 1' wherein M is in the +4 formal oxidation state are chloride, methyl, benzyl, trimethylsilyl or 2,3-dimethyl-2-butene-1,4-diyl.

Most highly preferred metal complexes of formula 1' are those wherein $Y^1$ and $Y^2$ are both inden-1-yl, 2-methyl-4-phenylinden-1-yl, 3-isopropylinden-1-yl, or 3-t-butylinden-1-yl groups, especially compositions comprising greater than 90 percent rac isomer.

Specific, but not limiting examples of metal complexes of formula 1 and formula 1' wherein M is in the +2 formal oxidation state are:

dimethylamidoborane-bis-$\eta^5$-cyclopentadienyl zirconium $\eta^4$-1,4-diphenyl-1,3-butadiene;
dimethylamidoborane-bis-$\eta^5$-cyclopentadienyl zirconium $\eta^4$-2,4-hexadiene;
dimethylamidoborane-bis-$\eta^5$-cyclopentadienyl zirconium $\eta^4$-1,4-dinaphthyl-1,3-butadiene;
dimethylamidoborane-bis-$\eta^5$-cyclopentadienyl zirconium $\eta^4$-1-phenyl-1,3-pentadiene;
dimethylamidoborane-bis-$\eta^5$-cyclopentadienyl zirconium $\eta^4$-1,3-pentadiene;
dimethylamidoborane-bis-$\eta^5$-n-butylcyclopentadienyl zirconium $\eta^4$-1,4-diphenyl-1,3-butadiene;
dimethylamidoborane-bis-$\eta^5$-n-butylcyclopentadienyl zirconium $\eta^4$-2,4-hexadiene;
dimethylamidoborane-bis-$\eta^5$-n-butylcyclopentadienyl zirconium $\eta^4$-1,4-dinaphthyl-1,3-butadiene;
dimethylamidoborane-bis-$\eta^5$-n-butylcyclopentadienyl zirconium $\eta^4$-1-phenyl-1,3-pentadiene;
dimethylamidoborane-bis-$\eta^5$-n-butylcyclopentadienyl zirconium $\eta^4$-1,3-pentadiene;
dimethylamidoborane-bis-$\eta^5$-inden-1-ylzirconium $\eta^4$-1,4-diphenyl-1,3-butadiene;
dimethylamidoborane-bis-$\eta^5$-inden-1-ylzirconium $\eta^4$-2,4-hexadiene;
dimethylamidoborane-bis-$\eta^5$-inden-1-ylzirconium $\eta^4$-1,4-dinaphthyl-1,3-butadiene;
dimethylamidoborane-bis-$\eta^5$-inden-1-ylzirconium $\eta^4$-1-phenyl-1,3-pentadiene;
dimethylamidoborane-bis-$\eta^5$-inden-1-ylzirconium $\eta^4$-1,3-pentadiene;
dimethylamidoborane-bis-$\eta^5$-(2-methylinden-1-yl)zirconium $\eta^4$-1,4-diphenyl-1,3-butadiene;
dimethylamidoborane-bis-$\eta^5$-(2-methylinden-1-yl)zirconium $\eta^4$-2,4-hexadiene;
dimethylamidoborane-bis-$\eta^5$-(2-methylinden-1-yl)zirconium $\eta^4$-1,4-dinaphthyl-1,3-butadiene;
dimethylamidoborane-bis-$\eta^5$-(2-methylinden-1-yl)zirconium $\eta^4$-1-phenyl-1,3-pentadiene;
dimethylamidoborane-bis-$\eta^5$-(2-methylinden-1-yl)zirconium $\eta^4$-1,3-pentadiene;
dimethylamidoborane-bis-$\eta^5$-(2-methyl-4-phenylinden-1-yl)zirconium $\eta^4$-1,4-diphenyl-1,3-butadiene;
dimethylamidoborane-bis-$\eta^5$-(2-methyl-4-phenylinden-1-yl)zirconium $\eta^4$-2,4-hexadiene;
dimethylamidoborane-bis-$\eta^5$-(2-methyl-4-phenylinden-1-yl)zirconium $\eta^4$-1,4-dinaphthyl-1,3-butadiene;
dimethylamidoborane-bis-$\eta^5$-(2-methyl-4-phenylinden-1-yl)zirconium $\eta^4$-1-phenyl-1,3-pentadiene;
dimethylamidoborane-bis-$\eta^5$-(2-methyl-4-phenylinden-1-yl)zirconium $\eta^4$-1,3-pentadiene;
dimethylamidoborane-bis-$\eta^5$-(2-ethyl-4-phenylinden-1-yl)zirconium $\eta^4$-1,4-diphenyl-1,3-butadiene;
dimethylamidoborane-bis-$\eta^5$-(2-ethyl-4-phenylinden-1-yl)zirconium $\eta^4$-2,4-hexadiene;
dimethylamidoborane-bis-$\eta^5$-(2-ethyl-4-phenylinden-1-yl)zirconium $\eta^4$-1,4-dinaphthyl-1,3-butadiene;
dimethylamidoborane-bis-$\eta^5$-(2-ethyl-4-phenylinden-1-yl)zirconium $\eta^4$-1-phenyl-1,3-pentadiene;
dimethylamidoborane-bis-$\eta^5$-(2-ethyl-4-phenylinden-1-yl)zirconium $\eta^4$-1,3-pentadiene;
dimethylamidoborane-bis-$\eta^5$-(2-isopropyl-4-phenylinden-1-yl)zirconium $\eta^4$-1,4-diphenyl-1,3-butadiene;
dimethylamidoborane-bis-$\eta^5$-(2-isopropyl-4-phenylinden-1-yl)zirconium $\eta^4$-2,4-hexadiene;
dimethylamidoborane-bis-$\eta^5$-(2-isopropyl-4-phenylinden-1-yl)zirconium $\eta^4$-1,4-dinaphthyl-1,3-butadiene;
dimethylamidoborane-bis-$\eta^5$-(2-isopropyl-4-phenylinden-1-yl)zirconium $\eta^4$-1-phenyl-1,3-pentadiene;
dimethylamidoborane-bis-$\eta^5$-(2-isopropyl-4-phenylinden-1-yl)zirconium $\eta^4$-1,3-pentadiene;
dimethylamidoborane-bis-$\eta^5$-(2-methyl-4-naphthylinden-1-yl)zirconium $\eta^4$-1,4-diphenyl-1,3-butadiene;
dimethylamidoborane-bis-$\eta^5$-(2-methyl-4-naphthylinden-1-yl)zirconium $\eta^4$-2,4-hexadiene;
dimethylamidoborane-bis-$\eta^5$-(2-methyl-4-naphthylinden-1-yl)zirconium $\eta^4$-1,4-dinaphthyl-1,3-butadiene;
dimethylamidoborane-bis-$\eta^5$-(2-methyl-4-naphthylinden-1-yl)zirconium $\eta^4$-phenyl-1,3-pentadiene;
dimethylamidoborane-bis-$\eta^5$-(2-methyl-4-naphthylinden-1-yl)zirconium $\eta^4$-1,3-pentadiene;
dimethylamidoborane-bis-$\eta^5$-(2-methyl-4-bis(3,5-trifluoromethyl)phenylinden-1-yl)zirconium $\eta^4$-1,4-diphenyl-1,3-butadiene;
dimethylamidoborane-bis-$\eta^5$-(2-methyl-4-bis(3,5-trifluoromethyl)phenylinden-1-yl)zirconium $\eta^4$-2,4-hexadiene;
dimethylamidoborane-bis-$\eta^5$-(2-methyl-4-bis(3,5-trifluoromethyl)phenylinden-1-yl)zirconium $\eta^4$-1,4-dinaphthyl-1,3-butadiene;
dimethylamidoborane-bis-$\eta^5$-(2-methyl-4-bis(3,5-trifluoromethyl)phenylinden-1-yl)zirconium $\eta^4$-4-phenyl-1,3-pentadiene;
dimethylamidoborane-bis-$\eta^5$-(2-methyl-4-bis(3,5-trifluoromethyl)phenylinden-1-yl)zirconium $\eta^4$-1,3-pentadiene;
dimethylamidoborane-bis-$\eta^5$-(2-ethyl-4-bis(3,5-trifluoromethyl)phenylinden-1-yl)zirconium $\eta^4$-1,4-diphenyl-1,3-butadiene;
dimethylamidoborane-bis-$\eta^5$-(2-ethyl-4-bis(3,5-trifluoromethyl)phenylinden-1-yl)zirconium $\eta^4$-2,4-hexadiene;
dimethylamidoborane-bis-$\eta^5$-(2-ethyl-4-bis(3,5-trifluoromethyl)phenylinden-1-yl)zirconium $\eta^4$-1,4-dinaphthyl-1,3-butadiene;
dimethylamidoborane-bis-$\eta^5$-(2-ethyl-4-bis(3,5-trifluoromethyl)phenylinden-1-yl)zirconium $\eta^4$-1-phenyl-1,3-pentadiene;
dimethylamidoborane-bis-$\eta^5$-(2-ethyl-4-bis(3,5-trifluoromethyl)phenylinden-1-yl)zirconium $\eta^4$-1,3-pentadiene;
dimethylamidoborane-bis-$\eta^5$-(2-isopropyl-4-bis(3,5-trifluoromethyl)phenylinden-1-yl)zirconium $\eta^4$-1,4-diphenyl-1,3-butadiene;
dimethylamidoborane-bis-$\eta^5$-(2-isopropyl-4-bis(3,5-trifluoromethyl)phenylinden-1-yl)zirconium $\eta^4$-2,4-hexadiene;
dimethylamidoborane-bis-$\eta^5$-(2-isopropyl-4-bis(3,5-trifluoromethyl)phenylinden-1-yl)zirconium $\eta^4$-1,4-dinaphthyl-1,3-butadiene;
dimethylamidoborane-bis-$\eta^5$-(2-isopropyl-4-bis(3,5-trifluoromethyl)phenylinden-1-yl)zirconium $\eta^4$-1-phenyl-1,3-pentadiene;
dimethylamidoborane-bis-$\eta^5$-(2-isopropyl-4-bis(3,5-trifluoromethyl)phenylinden-1-yl)zirconium $\eta^4$-1,3-pentadiene;
dimethylamidoborane-bis-$\eta^5$-(3-isopropylinden-1-yl)zirconium $\eta^4$-1-diphenyl-1,3-butadiene;

dimethylamidoborane-bis-$\eta^5$-(3-isopropylinden-1-yl)zirconium $\eta^4$-2,4-hexadiene;
dimethylamidoborane-bis-$\eta^5$-(3-isopropylinden-1-yl)zirconium $\eta^4$-1,4-dinaphthyl-1,3-butadiene;
dimethylamidoborane-bis-$\eta^5$-(3-isopropylinden-1-yl)zirconium $\eta^4$-1-phenyl-1,3-pentadiene;
dimethylamidoborane-bis-$\eta^5$-(3-isopropylinden-1-yl)zirconium $\eta^4$-1,3-pentadiene;
dimethylamidoborane-bis-$\eta^5$-(3-t-butylinden-1-yl)zirconium $\eta^4$-1,4-diphenyl-1,3-butadiene;
dimethylamidoborane-bis-$\eta^5$-(3-t-butylinden-1-yl)zirconium $\eta^4$-2,4-hexadiene;
dimethylamidoborane-bis-$\eta^5$-(3-t-butylinden-1-yl)zirconium $\eta^4$-1,4-dinaphthyl-1,3-butadiene;
dimethylamidoborane-bis-$\eta^5$-(3-t-butylinden-1-yl)zirconium $\eta^4$-1-phenyl-1,3-pentadiene;
dimethylamidoborane-bis-$\eta^5$-(3-t-butylinden-1-yl)zirconium $\eta^4$-1,3-pentadiene;
diisopropylamidoborane-bis-$\eta^5$-cyclopentadienylzirconium $\eta^4$-1,4-diphenyl-1,3-butadiene;
diisopropylamidoborane-bis-$\eta^5$-cyclopentadienylzirconium $\eta^4$-2,4-hexadiene;
diisopropylamidoborane-bis-$\eta^5$-cyclopentadienylzirconium $\eta^4$-1,4-dinaphthyl-1,3-butadiene;
diisopropylamidoborane-bis-$\eta^5$-cyclopentadienylzirconium $\eta^4$-1-phenyl-1,3-pentadiene;
diisopropylamidoborane-bis-$\eta^5$-cyclopentadienylzirconium $\eta^4$-1,3-pentadiene;
diisopropylamidoborane-bis-$\eta^5$-inden-1-ylzirconium $\eta^4$-1,4-diphenyl-1,3-butadiene;
diisopropylamidoborane-bis-$\eta^5$-inden-1-ylzirconium $\eta^4$-2,4-hexadiene;
diisopropylamidoborane-bis-$\eta^5$-inden-1-ylzirconium $\eta^4$-1,4-dinaphthyl-1,3-butadiene;
diisopropylamidoborane-bis-$\eta^5$-inden-1-ylzirconium $\eta^4$-1-phenyl-1,3-pentadiene;
diisopropylamidoborane-bis-$\eta^5$-inden-1-ylzirconium $\eta^4$-1,3-pentadiene;
diisopropylamidoborane-bis-$\eta^5$-(2-methylinden-1-yl)zirconium $\eta^4$-1-diphenyl-1,3-butadiene;
diisopropylamidoborane-bis-$\eta^5$-(2-methylinden-1-yl)zirconium $\eta^4$-2,4-hexadiene;
diisopropylamidoborane-bis-$\eta^5$-(2-methylinden-1-yl)zirconium $\eta^4$-1,4-dinaphthyl-1,3-butadiene;
diisopropylamidoborane-bis-$\eta^5$-(2-methylinden-1-yl)zirconium $\eta^4$-1-phenyl-1,3-pentadiene;
diisopropylamidoborane-bis-$\eta^5$-(2-methylinden-1-yl)zirconium $\eta^4$-1,3-pentadiene;
diisopropylamidoborane-bis-$\eta^5$-(2-methyl-4-phenylinden-1-yl)zirconium $\eta^4$-1,4-diphenyl-1,3-butadiene;
diisopropylamidoborane-bis-$\eta^5$-(2-methyl-4-phenylinden-1-yl)zirconium $\eta^4$-2,4-hexadiene;
diisopropylamidoborane-bis-$\eta^5$-(2-methyl-4-phenylinden-1-yl)zirconium $\eta^4$-1,4-dinaphthyl-1,3-butadiene;
diisopropylamidoborane-bis-$\eta^5$-(2-methyl-4-phenylinden-1-yl)zirconium $\eta^4$-1-phenyl-1,3-pentadiene;
diisopropylamidoborane-bis-$\eta^5$-(2-methyl-4-phenylinden-1-yl)zirconium $\eta^4$-1,3-pentadiene;
diisopropylamidoborane-bis-$\eta^5$-(2-methyl-4-naphthylinden-1-yl)zirconium $\eta^4$-1,4-diphenyl-1,3-butadiene;
diisopropylamidoborane-bis-$\eta^5$-(2-methyl-4-naphthylinden-1-yl)zirconium $\eta^4$-2,4-hexadiene;
diisopropylamidoborane-bis-$\eta^5$-(2-methyl-4-naphthylinden-1-yl)zirconium $\eta^4$-1,4-dinaphthyl-1,3-butadiene;
diisopropylamidoborane-bis-$\eta^5$-(2-methyl-4-naphthylinden-1-yl)zirconium $\eta^4$-1-phenyl-1,3-pentadiene;
diisopropylamidoborane-bis-$\eta^5$-(2-methyl-4-naphthylinden-1-yl)zirconium $\eta^4$-1,3-pentadiene;
diisopropylamidoborane-bis-$\eta^5$-(2-methyl-4-(3,5-dimethylphenyl)inden-1-yl)zirconium $\eta^4$-1,4-diphenyl-1,3-butadiene;
diisopropylamidoborane-bis-$\eta^5$-(2-methyl-4-(3,5-dimethylphenyl)inden-1-yl)zirconium $\eta^4$-2,4-hexadiene;
diisopropylamidoborane-bis-$\eta^5$-(2-methyl-4-(3,5-dimethylphenyl)inden-1-yl)zirconium $\eta^4$-1,4-dinaphthyl-1,3-butadiene;
diisopropylamidoborane-bis-$\eta^5$-(2-methyl-4-(3,5-dimethylphenyl)inden-1-yl)zirconium $\eta^4$-1-phenyl-1,3-pentadiene;
diisopropylamidoborane-bis-$\eta^5$-(2-methyl-4-(3,5-dimethylphenyl)inden-1-yl)zirconium $\eta^4$-1,3-pentadiene;
diisopropylamidoborane-bis-$\eta^5$-(2-methyl-4-(3,5-difluoromethylphenyl)inden-1-yl)zirconium $\eta^4$-1,4-diphenyl-1,3-butadiene;
diisopropylamidoborane-bis-$\eta^5$-(2-methyl-4-(3,5-difluoromethylphenyl)inden-1-yl)zirconium $\eta^4$-2,4-hexadiene;
diisopropylamidoborane-bis-$\eta^5$-(2-methyl-4-(3,5-difluoromethylphenyl)inden-1-yl)zirconium $\eta^4$-1,4-dinaphthyl-1,3-butadiene;
diisopropylamidoborane-bis-$\eta^5$-(2-methyl-4-(3,5-difluoromethylphenyl)inden-1-yl)zirconium $\eta^4$-phenyl-1,3-pentadiene;
diisopropylamidoborane-bis-$\eta^5$-(2-methyl-4-(3,5-difluoromethylphenyl)inden-1-yl)zirconium $\eta^4$-1,3-pentadiene;
diisopropylamidoborane-bis-$\eta^5$-(2-ethyl-4-phenylinden-1-yl)zirconium $\eta^4$-1,4-diphenyl-1,3-butadiene;
diisopropylamidoborane-bis-$\eta^5$-(2-ethyl-4-phenylinden-1-yl)zirconium $\eta^4$-2,4-hexadiene;
diisopropylamidoborane-bis-$\eta^5$-(2-ethyl-4-phenylinden-1-yl)zirconium $\eta^4$-1,4-dinaphthyl-1,3-butadiene;
diisopropylamidoborane-bis-$\eta^5$-(2-ethyl-4-phenylinden-1-yl)zirconium $\eta^4$-1-phenyl-1,3-pentadiene;
diisopropylamidoborane-bis-$\eta^5$-(2-ethyl-4-phenylinden-1-yl)zirconium $\eta^4$-1,3-pentadiene;
diisopropylamidoborane-bis-$\eta^5$-(2-isopropyl-4-phenylinden-1-yl)zirconium $\eta^4$-1,4-diphenyl-1,3-butadiene;
diisopropylamidoborane-bis-$\eta^5$-(2-isopropyl-4-phenylinden-1-yl)zirconium $\eta^4$-2,4-hexadiene;
diisopropylamidoborane-bis-$\eta^5$-(2-isopropyl-4-phenylinden-1-yl)zirconium $\eta^4$-1,4-dinaphthyl-1,3-butadiene;
diisopropylamidoborane-bis-$\eta^5$-(2-isopropyl-4-phenylinden-1-yl)zirconium $\eta^4$-1-phenyl-1,3-pentadiene;
diisopropylamidoborane-bis-$\eta^5$-(2-isopropyl-4-phenylinden-1-yl)zirconium $\eta^4$-1,3-pentadiene;
diisopropylamidoborane-bis-$\eta^5$-(3-isopropylinden-1-yl)zirconium $\eta^4$-1,4-diphenyl-1,3-butadiene;
diisopropylamidoborane-bis-$\eta^5$-(3-isopropylinden-1-yl)zirconium $\eta^4$-2,4-hexadiene;
diisopropylamidoborane-bis-$\eta^5$-(3-isopropylinden-1-yl)zirconium $\eta^4$-1,4-dinaphthyl-1,3-butadiene;
diisopropylamidoborane-bis-$\eta^5$-(3-isopropylinden-1-yl)zirconium $\eta^4$-1-phenyl-1,3-pentadiene;
diisopropylamidoborane-bis-$\eta^5$-(3-isopropylinden-1-yl)zirconium $\eta^4$-1,3-pentadiene;
diisopropylamidoborane-bis-$\eta^5$-(3-t-butylinden-1-yl)zirconium $\eta^4$-1,4-diphenyl-1,3-butadiene;
diisopropylamidoborane-bis-$\eta^5$-(3-t-butylinden-1-yl)zirconium $\eta^4$-2,4-hexadiene;
diisopropylamidoborane-bis-$\eta^5$-(3-t-butylinden-1-yl)zirconium $\eta^4$-1,4-dinaphthyl-1,3-butadiene;

diisopropylamidoborane-bis-$\eta^5$-(3-t-butylinden-1-yl) zirconium $\eta^4$-1-phenyl-1,3-pentadiene;
diisopropylamidoborane-bis-$\eta^5$-(3-t-butylinden-1-yl) zirconium $\eta^4$-1,3-pentadiene;
diphenylamidoborane-bis-$\eta^5$-cyclopentadienyl zirconium $\eta^4$-1,4-diphenyl-1,3-butadiene;
diphenylamidoborane-bis-$\eta^5$-cyclopentadienyl zirconium $\eta^4$-2,4-hexadiene;
diphenylamidoborane-bis-$\eta^5$-cyclopentadienyl zirconium $\eta^5$-1,4-dinaphthyl-1,3-butadiene;
diphenylamidoborane-bis-$\eta^5$-cyclopentadienyl zirconium $\eta^4$-1-phenyl-1,3-pentadiene;
diphenylamidoborane-bis-$\eta^5$-cyclopentadienyl zirconium $\eta^5$-1,3-pentadiene;
diphenylamidoborane-bis-$\eta^5$-n-butylcyclopentadienyl zirconium $\eta^4$-1,4-diphenyl-1,3-butadiene;
diphenylamidoborane-bis-$\eta^5$-n-butylcyclopentadienyl zirconium $\eta^4$-2,4-hexadiene;
diphenylamidoborane-bis-$\eta^5$-n-butylcyclopentadienyl zirconium $\eta^4$-1,4-dinaphthyl-1,3-butadiene;
diphenylamidoborane-bis-$\eta^5$-n-butylcyclopentadienyl zirconium $\eta^4$-1-phenyl-1,3-pentadiene;
diphenylamidoborane-bis-$\eta^5$-n-butylcyclopentadienyl zirconium $\eta^4$-1,3-pentadiene;
diphenylamidoborane-bis-$\eta^5$-inden-1-ylzirconium $\eta^4$-1,4-diphenyl-1,3-butadiene;
diphenylamidoborane-bis-$\eta^5$-inden-1-ylzirconium $\eta^4$-2,4-hexadiene;
diphenylamidoborane-bis-$\eta^5$-inden-1-ylzirconium $\eta^4$-1,4-dinaphthyl-1,3-butadiene;
diphenylamidoborane-bis-$\eta^5$-inden-1-ylzirconium $\eta^4$-1-phenyl-1,3-pentadiene;
diphenylamidoborane-bis-$\eta^5$-inden-1-ylzirconium $\eta^5$-1,3-pentadiene;
diphenylamidoborane-bis-$\eta^5$-(2-methylinden-1-yl) zirconium $\eta^4$-1,4-diphenyl-1,3-butadiene;
diphenylamidoborane-bis-$\eta^5$-(2-methylinden-1-yl) zirconium $\eta^4$-2,4-hexadiene;
diphenylamidoborane-bis-$\eta^5$-(2-methylinden-1-yl) zirconium $\eta^4$-1,4-dinaphthyl-1,3-butadiene;
diphenylamidoborane-bis-$\eta^5$-(2-methylinden-1-yl) zirconium $\eta^5$-1-phenyl-1,3-pentadiene;
diphenylamidoborane-bis-$\eta^5$-(2-methylinden-1-yl) zirconium $\eta^5$-1,3-pentadiene;
diphenylamidoborane-bis-$\eta^5$-(2-methyl-4-phenylinden-1-yl)zirconium $\eta^4$-1,4-diphenyl-1,3-butadiene;
diphenylamidoborane-bis-$\eta^5$-(2-methyl-4-phenylinden-1-yl)zirconium $\eta^4$-2,4-hexadiene;
diphenylamidoborane-bis-$\eta^5$-(2-methyl-4-phenylinden-1-yl)zirconium $\eta^4$-1,4-dinaphthyl-1,3-butadiene;
diphenylamidoborane-bis-$\eta^5$-(2-methyl-4-phenylinden-1-yl)zirconium $\eta^4$-1-phenyl-1,3-pentadiene;
diphenylamidoborane-bis-$\eta^5$-(2-methyl-4-phenylinden-1-yl)zirconium $\eta^4$-1,3-pentadiene;
diphenylamidoborane-bis-$\eta^5$-(2-ethyl-4-phenylinden-1-yl) zirconium $\eta^4$-1,4-diphenyl-1,3-butadiene;
diphenylamidoborane-bis-$\eta^5$-(2-ethyl-4-phenylinden-1-yl) zirconium $\eta^4$-2,4-hexadiene;
diphenylamidoborane-bis-$\eta^5$-(2-ethyl-4-phenylinden-1-yl) zirconium $\eta^4$-1,4-dinaphthyl-1,3-butadiene;
diphenylamidoborane-bis-$\eta^5$-(2-ethyl-4-phenylinden-1-yl) zirconium $\eta^4$-1-phenyl-1,3-pentadiene;
diphenylamidoborane-bis-$\eta^5$-(2-ethyl-4-phenylinden-1-yl) zirconium $\eta^4$-1,3-pentadiene;
diphenylamidoborane-bis-$\eta^5$-(2-isopropyl-4-phenylinden-1-yl)zirconium $\eta^4$-1,4-diphenyl-1,3-butadiene;
diphenylamidoborane-bis-$\eta^5$-(2-isopropyl-4-phenylinden-1-yl)zirconium $\eta^4$-2,4-hexadiene;
diphenylamidoborane-bis-$\eta^5$-(2-isopropyl-4-phenylinden-1-yl)zirconium $\eta^4$-1,4-dinaphthyl-1,3-butadiene;
diphenylamidoborane-bis-$\eta^5$-(2-isopropyl-4-phenylinden-1-yl)zirconium $\eta^4$-phenyl-1,3-pentadiene;
diphenylamidoborane-bis-$\eta^5$-(2-isopropyl-4-phenylinden-1-yl)zirconium $\eta^4$-1,3-pentadiene;
diphenylamidoborane-bis-$\eta^5$-(2-methyl-4-naphthylinden-1-yl)zirconium $\eta^4$-1,4-diphenyl-1,3-butadiene;
diphenylamidoborane-bis-$\eta^5$-(2-methyl-4-naphthylinden-1-yl)zirconium $\eta^4$-2,4-hexadiene;
diphenylamidoborane-bis-$\eta^5$-(2-methyl-4-naphthylinden-1-yl)zirconium $\eta^4$-1,4-dinaphthyl-1,3-butadiene;
diphenylamidoborane-bis-$\eta^5$-(2-methyl-4-naphthylinden-1-yl)zirconium $\eta^4$-phenyl-1,3-pentadiene;
diphenylamidoborane-bis-$\eta^5$-(2-methyl-4-naphthylinden-1-yl)zirconium $\eta^4$-1,3-pentadiene;
diphenylamidoborane-bis-$\eta^5$-(2-methyl-4-bis(3,5-trifluoromethyl)phenylinden-1-yl)zirconium $\eta^4$-1,4-diphenyl-1,3-butadiene;
diphenylamidoborane-bis-$\eta^5$-(2-methyl-4-bis(3,5-trifluoromethyl)phenylinden-1-yl)zirconium $\eta^4$-2,4-hexadiene;
diphenylamidoborane-bis-$\eta^5$-(2-methyl-4-bis(3,5-trifluoromethyl)phenylinden-1-yl)zirconium $\eta^4$-1,4-dinaphthyl-1,3-butadiene;
diphenylamidoborane-bis-$\eta^5$-(2-methyl-4-bis(3,5-trifluoromethyl)phenylinden-1-yl)zirconium $\eta^4$-1-phenyl-1,3-pentadiene;
diphenylamidoborane-bis-$\eta^5$-(2-methyl-4-bis(3,5-trifluoromethyl)phenylinden-1-yl)zirconium $\eta^4$-1,3-pentadiene;
diphenylamidoborane-bis-$\eta^5$-(2-ethyl-4-bis(3,5-trifluoromethyl)phenylinden-1-yl)zirconium $\eta^4$-1,4-diphenyl-1,3-butadiene;
diphenylamidoborane-bis-$\eta^5$-(2-ethyl-4-bis(3,5-trifluoromethyl)phenylinden-1-yl)zirconium $\eta^4$-2,4-hexadiene;
diphenylamidoborane-bis-$\eta^5$-(2-ethyl-4-bis(3,5-trifluoromethyl)phenylinden-1-yl)zirconium $\eta^4$-1,4-dinaphthyl-1,3-butadiene;
diphenylamidoborane-bis-$\eta^5$-(2-ethyl-4-bis(3,5-trifluoromethyl)phenylinden-1-yl)zirconium $\eta^4$-1-phenyl-1,3-pentadiene;
diphenylamidoborane-bis-$\eta^5$-(2-ethyl-4-bis(3,5-trifluoromethyl)phenylinden-1-yl)zirconium $\eta^4$-1,3-pentadiene;
diphenylamidoborane-bis-$\eta^5$-(2-isopropyl-4-bis(3,5-trifluoromethyl)phenylinden-1-yl)zirconium $\eta^4$-1,4-diphenyl-1,3-butadiene;
diphenylamidoborane-bis-$\eta^5$-(2-isopropyl-4-bis(3,5-trifluoromethyl)phenylinden-1-yl)zirconium $\eta^4$-2,4-hexadiene;
diphenylamidoborane-bis-$\eta^5$-(2-isopropyl-4-bis(3,5-trifluoromethyl)phenylinden-1-yl)zirconium $\eta^4$-1,4-dinaphthyl-1,3-butadiene;
diphenylamidoborane-bis-$\eta^5$-(2-isopropyl-4-bis(3,5-trifluoromethyl)phenylinden-1-yl)zirconium $\eta^4$-1-phenyl-1,3-pentadiene;
diphenylamidoborane-bis-$\eta^5$-(2-isopropyl-4-bis(3,5-trifluoromethyl)phenylinden-1-yl)zirconium $\eta^4$-1,3-pentadiene;
diphenylamidoborane-bis-$\eta^5$-(3-isopropylinden-1-yl) zirconium $\eta^4$-1,4-diphenyl-1,3-butadiene;
diphenylamidoborane-bis-$\eta^5$-(3-isopropylinden-1-yl) zirconium $\eta^4$-2,4-hexadiene;
diphenylamidoborane-bis-$\eta^5$-(3-isopropylinden-1-yl) zirconium $\eta^4$-1,4-dinaphthyl-1,3-butadiene;

diphenylamidoborane-bis-$\eta^5$-(3-isopropylinden-1-yl)zirconium $\eta^4$-1-phenyl-1,3-pentadiene;
diphenylamidoborane-bis-$\eta^5$-(3-isopropylinden-1-yl)zirconium $\eta^4$-1,3-pentadiene;
diphenylamidoborane-bis-$\eta^5$-(3-t-butylinden-1-yl)zirconium $\eta^4$-1,4-diphenyl-1,3-butadiene;
diphenylamidoborane-bis-$\eta^5$-(3-t-butylinden-1-yl)zirconium $\eta^4$-2,4-hexadiene;
diphenylamidoborane-bis-$\eta^5$-(3-t-butylinden-1-yl)zirconium $\eta^4$-1,4-dinaphthyl-1,3-butadiene;
diphenylamidoborane-bis-$\eta^5$-(3-t-butylinden-1-yl)zirconium $\eta^4$-1-phenyl-1,3-pentadiene;
diphenylamidoborane-bis-$\eta^5$-(3-t-butylinden-1-yl)zirconium $\eta^4$-1,3-pentadiene;
isoindolenidoborane-bis-$\eta^5$-cyclopentadienyl zirconium $\eta^4$-1,4-diphenyl-1,3-butadiene;
isoindolenidoborane-bis-$\eta^5$-cyclopentadienyl zirconium $\eta^4$-2,4-hexadiene;
isoindolenidoborane-bis-$\eta^5$-cyclopentadienyl zirconium $\eta^4$-1,4-dinaphthyl-1,3-butadiene;
isoindolenidoborane-bis-$\eta^5$-cyclopentadienyl zirconium $\eta^4$-1-phenyl-1,3-pentadiene;
isoindolenidoborane-bis-$\eta^5$-cyclopentadienyl zirconium $\eta^4$-1,3-pentadiene;
isoindolenidoborane-bis-$\eta^5$-n-butylcyclopentadienyl zirconium $\eta^4$-1,4-diphenyl-1,3-butadiene;
isoindolenidoborane-bis-$\eta^5$-n-butylcyclopentadienyl zirconium $\eta^4$-2,4-hexadiene;
isoindolenidoborane-bis-$\eta^5$-n-butylcyclopentadienyl zirconium $\eta^4$-1,4-dinaphthyl-1,3-butadiene;
isoindolenidoborane-bis-$\eta^5$-n-butylcyclopentadienyl zirconium $\eta^4$-1-phenyl-1,3-pentadiene;
isoindolenidoborane-bis-$\eta^5$-n-butylcyclopentadienyl zirconium $\eta^4$-1,3-pentadiene;
isoindolenidoborane-bis-$\eta^5$-inden-1-ylzirconium $\eta^4$-1,4-diphenyl-1,3-butadiene;
isoindolenidoborane-bis-$\eta^5$-inden-1-ylzirconium $\eta^4$-2,4-hexadiene;
isoindolenidoborane-bis-$\eta^5$-inden-1-ylzirconium $\eta^4$-1,4-dinaphthyl-1,3-butadiene;
isoindolenidoborane-bis-$\eta^5$-inden-1-ylzirconium $\eta^4$-1-phenyl-1,3-pentadiene;
isoindolenidoborane-bis-$\eta^5$-inden-1-ylzirconium $\eta^4$-1,3-pentadiene;
isoindolenidoborane-bis-$\eta^5$-(2-methylinden-1-yl)zirconium $\eta^4$-1,4-diphenyl-1,3-butadiene;
isoindolenidoborane-bis-$\eta^5$-(2-methylinden-1-yl)zirconium $\eta^4$-2,4-hexadiene;
isoindolenidoborane-bis-$\eta^5$-(2-methylinden-1-yl)zirconium $\eta^4$-1,4-dinaphthyl-1,3-butadiene;
isoindolenidoborane-bis-$\eta^5$-(2-methylinden-1-yl)zirconium $\eta^4$-1-phenyl-1,3-pentadiene;
isoindolenidoborane-bis-$\eta^5$-(2-methylinden-1-yl)zirconium $\eta^4$-1,3-pentadiene;
isoindolenidoborane-bis-$\eta^5$-(2-methyl-4-phenylinden-1-yl)zirconium $\eta^4$-1,4-diphenyl-1,3-butadiene;
isoindolenidoborane-bis-$\eta^5$-(2-methyl-4-phenylinden-1-yl)zirconium $\eta^4$-2,4-hexadiene;
isoindolenidoborane-bis-$\eta^5$-(2-methyl-4-phenylinden-1-yl)zirconium $\eta^4$-1,4-dinaphthyl-1,3-butadiene;
isoindolenidoborane-bis-$\eta^5$-(2-methyl-4-phenylinden-1-yl)zirconium $\eta^4$-1-phenyl-1,3-pentadiene;
isoindolenidoborane-bis-$\eta^5$-(2-methyl-4-phenylinden-1-yl)zirconium $\eta^4$-1,3-pentadiene;
isoindolenidoborane-bis-$\eta^5$-(2-ethyl-4-phenylinden-1-yl)zirconium $\eta^4$-1,4-diphenyl-1,3-butadiene;
isoindolenidoborane-bis-$\eta^5$-(2-ethyl-4-phenylinden-1-yl)zirconium $\eta^4$-2,4-hexadiene;
isoindolenidoborane-bis-$\eta^5$-(2-ethyl-4-phenylinden-1-yl)zirconium $\eta^4$-1,4-dinaphthyl-1,3-butadiene;
isoindolenidoborane-bis-$\eta^5$-(2-ethyl-4-phenylinden-1-yl)zirconium $\eta^4$-1-phenyl-1,3-pentadiene;
isoindolenidoborane-bis-$\eta^5$-(2-ethyl-4-phenylinden-1-yl)zirconium $\eta^4$-1,3-pentadiene;
isoindolenidoborane-bis-$\eta^5$-(2-isopropyl-4-phenylinden-1-yl)zirconium $\eta^4$-1,4-diphenyl-1,3-butadiene;
isoindolenidoborane-bis-$\eta^5$-(2-isopropyl-4-phenylinden-1-yl)zirconium $\eta^4$-2,4-hexadiene;
isoindolenidoborane-bis-$\eta^5$-(2-isopropyl-4-phenylinden-1-yl)zirconium $\eta^4$-1,4-dinaphthyl-1,3-butadiene;
isoindolenidoborane-bis-$\eta^5$-(2-isopropyl-4-phenylinden-1-yl)zirconium $\eta^4$-1-phenyl-1,3-pentadiene;
isoindolenidoborane-bis-$\eta^5$-(2-isopropyl-4-phenylinden-1-yl)zirconium $\eta^4$-1,3-pentadiene;
isoindolenidoborane-bis-$\eta^5$-(2-methyl-4-naphthylinden-1-yl)zirconium $\eta^4$-1,4-diphenyl-1,3-butadiene;
isoindolenidoborane-bis-$\eta^5$-(2-methyl-4-naphthylinden-1-yl)zirconium $\eta^4$-2,4-hexadiene;
isoindolenidoborane-bis-$\eta^5$-(2-methyl-4-naphthylinden-1-yl)zirconium $\eta^4$-1,4-dinaphthyl-1,3-butadiene;
isoindolenidoborane-bis-$\eta^5$-(2-methyl-4-naphthylinden-1-yl)zirconium $\eta^4$-1-phenyl-1,3-pentadiene;
isoindolenidoborane-bis-$\eta^5$-(2-methyl-4-naphthylinden-1-yl)zirconium $\eta^4$-1,3-pentadiene;
isoindolenidoborane-bis-$\eta^5$-(2-methyl-4-bis(3,5-trifluoromethyl)phenylinden-1-yl)zirconium $\eta^4$-1,4-diphenyl-1,3-butadiene;
isoindolenidoborane-bis-$\eta^5$-(2-methyl-4-bis(3,5-trifluoromethyl)phenylinden-1-yl)zirconium $\eta^4$-2,4-hexadiene;
isoindolenidoborane-bis-$\eta^5$-(2-methyl-4-bis(3,5-trifluoromethyl)phenylinden-1-yl)zirconium $\eta^4$-1,4-dinaphthyl-1,3-butadiene;
isoindolenidoborane-bis-$\eta^5$-(2-methyl-4-bis(3,5-trifluoromethyl)phenylinden-1-yl)zirconium $\eta^4$-1-phenyl-1,3-pentadiene;
isoindolenidoborane-bis-$\eta^5$-(2-methyl-4-bis(3,5-trifluoromethyl)phenylinden-1-yl)zirconium $\eta^4$-1,3-pentadiene;
isoindolenidoborane-bis-$\eta^5$-(2-ethyl-4-bis(3,5-trifluoromethyl)phenylinden-1-yl)zirconium $\eta^4$-1,4-diphenyl-1,3-butadiene;
isoindolenidoborane-bis-$\eta^5$-(2-ethyl-4-bis(3,5-trifluoromethyl)phenylinden-1-yl)zirconium $\eta^4$-2,4-hexadiene;
isoindolenidoborane-bis-$\eta^5$-(2-ethyl-4-bis(3,5-trifluoromethyl)phenylinden-1-yl)zirconium $\eta^4$-1,4-dinaphthyl-1,3-butadiene;
isoindolenidoborane-bis-$\eta^5$-(2-ethyl-4-bis(3,5-trifluoromethyl)phenylinden-1-yl)zirconium $\eta^4$-1-phenyl-1,3-pentadiene;
isoindolenidoborane-bis-$\eta^5$-(2-ethyl-4-bis(3,5-trifluoromethyl)phenylinden-1-yl)zirconium $\eta^4$-1,3-pentadiene;
isoindolenidoborane-bis-$\eta^5$-(2-isopropyl-4-bis(3,5-trifluoromethyl)phenylinden-1-yl)zirconium $\eta^4$-1,4-diphenyl-1,3-butadiene;
isoindolenidoborane-bis-$\eta^5$-(2-isopropyl-4-bis(3,5-trifluoromethyl)phenylinden-1-yl)zirconium $\eta^4$-2,4-hexadiene;
isoindolenidoborane-bis-$\eta^5$-(2-isopropyl-4-bis(3,5-trifluoromethyl)phenylinden-1-yl)zirconium $\eta^4$-1,4-dinaphthyl-1,3-butadiene;
isoindolenidoborane-bis-$\eta^5$-(2-isopropyl-4-bis(3,5-trifluoromethyl)phenylinden-1-yl)zirconium $\eta^4$-1-phenyl-1,3-pentadiene;

isoindolenidoborane-bis-$\eta^5$-(2-isopropyl-4-bis(3,5-trifluoromethyl)phenylinden-1-yl)zirconium $\eta^4$-1,3-pentadiene;
isoindolenidoborane-bis-$\eta^5$-(3-isopropylinden-1-yl)zirconium $\eta^4$-1,4-diphenyl-1,3-butadiene;
isoindolenidoborane-bis-$\eta^5$-(3-isopropylinden-1-yl)zirconium $\eta^4$-2,4-hexadiene;
isoindolenidoborane-bis-$\eta^5$-(3-isopropylinden-1-yl)zirconium $\eta^5$-1,4-dinaphthyl-1,3-butadiene;
isoindolenidoborane-bis-$\eta^5$-(3-isopropylinden-1-yl)zirconium $\eta^4$-1-phenyl-1,3-pentadiene;
isoindolenidoborane-bis-$\eta^5$-(3-isopropylinden-1-yl)zirconium $\eta^4$-1,3-pentadiene;
isoindolenidoborane-bis-$\eta^5$-(3-t-butylinden-1-yl)zirconium $\eta^4$-1,4-diphenyl-1,3-butadiene;
isoindolenidoborane-bis-$\eta^5$-(3-t-butylinden-1-yl)zirconium $\eta^4$-2,4-hexadiene;
isoindolenidoborane-bis-$\eta^5$-(3-t-butylinden-1-yl)zirconium $\eta^4$-1,4-dinaphthyl-1,3-butadiene;
isoindolenidoborane-bis-$\eta^5$-(3-t-butylinden-1-yl)zirconium $\eta^4$-1-phenyl-1,3-pentadiene;
isoindolenidoborane-bis-$\eta^5$-(3-t-butylinden-1-yl)zirconium $\eta^4$-1,3-pentadiene;
bis(4-dimethylaminophenyl)borane-bis-$\eta^5$-cyclopentadienyl zirconium $\eta^4$-1,4-diphenyl-1,3-butadiene;
bis(4-dimethylaminophenyl)borane-bis-$\eta^5$-cyclopentadienyl zirconium $\eta^4$-2,4-hexadiene;
bis(4-dimethylaminophenyl)borane-bis-$\eta^5$-cyclopentadienyl zirconium $\eta^4$-1,4-dinaphthyl-1,3-butadiene;
bis(4-dimethylaminophenyl)borane-bis-$\eta^5$-cyclopentadienyl zirconium $\eta^4$-1-phenyl-1,3-pentadiene;
bis(4-dimethylaminophenyl)borane-bis-$\eta^5$-cyclopentadienyl zirconium $\eta^4$-1,3-pentadiene;
bis(4-dimethylaminophenyl)borane-bis-$\eta^5$-n-butylcyclopentadienyl zirconium $\eta^4$-1,4-diphenyl-1,3-butadiene;
bis(4-dimethylaminophenyl)borane-bis-$\eta^5$-n-butylcyclopentadienyl zirconium $\eta^4$-2,4-hexadiene;
bis(4-dimethylaminophenyl)borane-bis-$\eta^5$-n-butylcyclopentadienyl zirconium $\eta^4$-1,4-dinaphthyl-1,3-butadiene;
bis(4-dimethylaminophenyl)borane-bis-$\eta^5$-n-butylcyclopentadienyl zirconium $\eta^4$-1-phenyl-1,3-pentadiene;
bis(4-dimethylaminophenyl)borane-bis-$\eta^5$-n-butylcyclopentadienyl zirconium $\eta^4$-1,3-pentadiene;
bis(4-dimethylaminophenyl)borane-bis-$\eta^5$-inden-1-ylzirconium $\eta^4$-1,4-diphenyl-1,3-butadiene;
bis(4-dimethylaminophenyl)borane-bis-$\eta^5$-inden-1-ylzirconium $\eta^4$-2,4-hexadiene;
bis(4-dimethylaminophenyl)borane-bis-$\eta^5$-inden-1-ylzirconium $\eta^4$-1,4-dinaphthyl-1,3-butadiene;
bis(4-dimethylaminophenyl)borane-bis-$\eta^5$-inden-1-ylzirconium $\eta^4$-1-phenyl-1,3-pentadiene;
bis(4-dimethylaminophenyl)borane-bis-$\eta^5$-inden-1-ylzirconium $\eta^4$-1,3-pentadiene;
bis(4-dimethylaminophenyl)borane-bis-$\eta^5$-(2-methylinden-1-yl)zirconium $\eta^4$-1,4-diphenyl-1,3-butadiene;
bis(4-dimethylaminophenyl)borane-bis-$\eta^5$-(2-methylinden-1-yl)zirconium $\eta^4$-2,4-hexadiene;
bis(4-dimethylaminophenyl)borane-bis-$\eta^5$-(2-methylinden-1-yl)zirconium $\eta^4$-1,4-dinaphthyl-1,3-butadiene;
bis(4-dimethylaminophenyl)borane-bis-$\eta^5$-(2-methylinden-1-yl)zirconium $\eta^4$-1-phenyl-1,3-pentadiene;
bis(4-dimethylaminophenyl)borane-bis-$\eta^5$-(2-methylinden-1-yl)zirconium $\eta^4$-1,3-pentadiene;
bis(4-dimethylaminophenyl)borane-bis-$\eta^5$-(2-methyl-4-phenylinden-1-yl)zirconium $\eta^4$-1,4-diphenyl-1,3-butadiene;
bis(4-dimethylaminophenyl)borane-bis-$\eta^5$-(2-methyl-4-phenylinden-1-yl)zirconium $\eta^4$-2,4-hexadiene;
bis(4-dimethylaminophenyl)borane-bis-$\eta^5$-(2-methyl-4-phenylinden-1-yl)zirconium $\eta^4$-1,4-dinaphthyl-1,3-butadiene;
bis(4-dimethylaminophenyl)borane-bis-$\eta^5$-(2-methyl-4-phenylinden-1-yl)zirconium $\eta^4$-1-phenyl-1,3-pentadiene;
bis(4-dimethylaminophenyl)borane-bis-$\eta^5$-(2-methyl-4-phenylinden-1-yl)zirconium $\eta^4$-1,3-pentadiene;
bis(4-dimethylaminophenyl)borane-bis-$\eta^5$-(2-ethyl-4-phenylinden-1-yl)zirconium $\eta^4$-1,4-diphenyl-1,3-butadiene;
bis(4-dimethylaminophenyl)borane-bis-$\eta^5$-(2-ethyl-4-phenylinden-1-yl)zirconium $\eta^4$-2,4-hexadiene;
bis(4-dimethylaminophenyl)borane-bis-$\eta^5$-(2-ethyl-4-phenylinden-1-yl)zirconium $\eta^4$-1,4-dinaphthyl-1,3-butadiene;
bis(4-dimethylaminophenyl)borane-bis-$\eta^5$-(2-ethyl-4-phenylinden-1-yl)zirconium $\eta^4$-1-phenyl-1,3-pentadiene;
bis(4-dimethylaminophenyl)borane-bis-$\eta^5$-(2-ethyl-4-phenylinden-1-yl)zirconium $\eta^4$-1,3-pentadiene;
bis(4-dimethylaminophenyl)borane-bis-$\eta^5$-(2-isopropyl-4-phenylinden-1-yl)zirconium $\eta^4$-1,4-diphenyl-1,3-butadiene;
bis(4-dimethylaminophenyl)borane-bis-$\eta^5$-(2-isopropyl-4-phenylinden-1-yl)zirconium $\eta^4$-2,4-hexadiene;
bis(4-dimethylaminophenyl)borane-bis-$\eta^5$-(2-isopropyl-4-phenylinden-1-yl)zirconium $\eta^4$-1,4-dinaphthyl-1,3-butadiene;
bis(4-dimethylaminophenyl)borane-bis-$\eta^5$-(2-isopropyl-4-phenylinden-1-yl)zirconium $\eta^4$-1-phenyl-1,3-pentadiene;
bis(4-dimethylaminophenyl)borane-bis-$\eta^5$-(2-isopropyl-4-phenylinden-1-yl)zirconium $\eta^4$-1,3-pentadiene;
bis(4-dimethylaminophenyl)borane-bis-$\eta^5$-(2-methyl-4-naphthylinden-1-yl)zirconium $\eta^4$-1,4-diphenyl-1,3-butadiene;
bis(4-dimethylaminophenyl)borane-bis-$\eta^5$-(2-methyl-4-naphthylinden-1-yl)zirconium $\eta^4$-2,4-hexadiene;
bis(4-dimethylaminophenyl)borane-bis-$\eta^5$-(2-methyl-4-naphthylinden-1-yl)zirconium $\eta^4$-1,4-dinaphthyl-1,3-butadiene;
bis(4-dimethylaminophenyl)borane-bis-$\eta^5$-(2-methyl-4-naphthylinden-1-yl)zirconium $\eta^4$-1-phenyl-1,3-pentadiene;
bis(4-dimethylaminophenyl)borane-bis-$\eta^5$-(2-methyl-4-naphthylinden-1-yl)zirconium $\eta^4$-1,3-pentadiene;
bis(4-dimethylaminophenyl)borane-bis-$\eta^5$-(2-methyl-4-bis(3,5-trifluoromethyl)phenylinden-1-yl)zirconium $\eta^4$-1,4-diphenyl-1,3-butadiene;
bis(4-dimethylaminophenyl)borane-bis-$\eta^5$-(2-methyl-4-bis(3,5-trifluoromethyl)phenylinden-1-yl)zirconium $\eta^4$-2,4-hexadiene;
bis(4-dimethylaminophenyl)borane-bis-$\eta^5$-(2-methyl-4-bis(3,5-trifluoromethyl)phenylinden-1-yl)zirconium $\eta^4$-1,4-dinaphthyl-1,3-butadiene;
bis(4-dimethylaminophenyl)borane-bis-$\eta^5$-(2-methyl-4-bis(3,5-trifluoromethyl)phenylinden-1-yl)zirconium $\eta^4$-1-phenyl-1,3-pentadiene;
bis(4-dimethylaminophenyl)borane-bis-$\eta^5$-(2-methyl-4-bis(3,5-trifluoromethyl)phenylinden-1-yl)zirconium $\eta^4$-1,3-pentadiene;
bis(4-dimethylaminophenyl)borane-bis-$\eta^5$-(2-ethyl-4-bis(3,5-trifluoromethyl)phenylinden-1-yl)zirconium $\eta^4$-1,4-diphenyl-1,3-butadiene;

bis(4-dimethylaminophenyl)borane-bis-η$^5$-(2-ethyl-4-bis(3, 5-trifluoromethyl)phenylinden-1-yl)zirconium η$^4$-2,4-hexadiene;
bis(4-dimethylaminophenyl)borane-bis-η$^5$-(2-ethyl-4-bis(3, 5-trifluoromethyl)phenylinden-1-yl)zirconium η$^4$-1,4-dinaphthyl-1,3-butadiene;
bis(4-dimethylaminophenyl)borane-bis-η$^5$-(2-ethyl-4-bis(3, 5-trifluoromethyl)phenylinden-1-yl)zirconium η$^4$-1-phenyl-1,3-pentadiene;
bis(4-dimethylaminophenyl)borane-bis-η$^5$-(2-ethyl-4-bis(3, 5-trifluoromethyl)phenylinden-1-yl)zirconium η$^4$-1,3-pentadiene;
bis(4-dimethylaminophenyl)borane-bis-η$^5$-(2-isopropyl-4-bis(3,5-trifluoromethyl)phenylinden-1-yl)zirconium η$^4$-1,4-diphenyl-1,3-butadiene;
bis(4-dimethylaminophenyl)borane-bis-η$^5$-(2-isopropyl-4-bis(3,5-trifluoromethyl)phenylinden-1-yl)zirconium η$^4$-2,4-hexadiene;
bis(4-dimethylaminophenyl)borane-bis-η$^5$-(2-isopropyl-4-bis(3,5-trifluoromethyl)phenylinden-1-yl)zirconium η$^5$-1,4-dinaphthyl-1,3-butadiene;
bis(4-dimethylaminophenyl)borane-bis-η$^5$-(2-isopropyl-4-bis(3,5-trifluoromethyl)phenylinden-1-yl)zirconium η$^4$-1-phenyl-1,3-pentadiene;
bis(4-dimethylaminophenyl)borane-bis-η$^5$-(2-isopropyl-4-bis(3,5-trifluoromethyl)phenylinden-1-yl)zirconium η$^4$-1,3-pentadiene;
bis(4-dimethylaminophenyl)borane-bis-η$^5$-(3-isopropylinden-1-yl)zirconium η$^4$-1,4-diphenyl-1,3-butadiene;
bis(4-dimethylaminophenyl)borane-bis-η$^5$-(3-isopropylinden-1-yl)zirconium η$^4$-2,4-hexadiene;
bis(4-dimethylaminophenyl)borane-bis-η$^5$-(3-isopropylinden-1-yl)zirconium η$^4$-1,4-dinaphthyl-1,3-butadiene;
bis(4-dimethylaminophenyl)borane-bis-η$^5$-(3-isopropylinden-1-yl)zirconium η$^4$-1-phenyl-1,3-pentadiene;
bis(4-dimethylaminophenyl)borane-bis-η$^5$-(3-isopropylinden-1-yl)zirconium η$^4$-1,3-pentadiene;
bis(4-dimethylaminophenyl)borane-bis-η$^5$-(3-t-butylinden-1-yl)zirconium η$^4$-1,4-diphenyl-1,3-butadiene;
bis(4-dimethylaminophenyl)borane-bis-η$^5$-(3-t-butylinden-1-yl)zirconium η$^4$-2,4-hexadiene;
bis(4-dimethylaminophenyl)borane-bis-η$^5$-(3-t-butylinden-1-yl)zirconium η$^4$-1,4-dinaphthyl-1,3-butadiene;
bis(4-dimethylaminophenyl)borane-bis-η$^5$-(3-t-butylinden-1-yl)zirconium η$^4$-1-phenyl-1,3-pentadiene;
bis(4-dimethylaminophenyl)borane-bis-η$^5$-(3-t-butylinden-1-yl)zirconium η$^4$-1,3-pentadiene;
N-methylpiperazinoborane-bis-η$^5$-cyclopentadienyl zirconium η$^4$-1,4-diphenyl-1,3-butadiene;
N-methylpiperazinoborane-bis-η$^5$-cyclopentadienyl zirconium η$^4$-2,4-hexadiene;
N-methylpiperazinoborane-bis-η$^5$-cyclopentadienyl zirconium η$^4$-1,4-dinaphthyl-1,3-butadiene;
N-methylpiperazinoborane-bis-η$^5$-cyclopentadienyl zirconium η$^4$-1-phenyl-1,3-pentadiene;
N-methylpiperazinoborane-bis-η$^5$-cyclopentadienyl zirconium η$^5$-1,3-pentadiene;
N-methylpiperazinoborane-bis-η$^5$-n-butylcyclopentadienyl zirconium η$^4$-1,4-diphenyl-1,3-butadiene;
N-methylpiperazinoborane-bis-η$^5$-n-butylcyclopentadienyl zirconium η$^4$-2,4-hexadiene;
N-methylpiperazinoborane-bis-η$^5$-n-butylcyclopentadienyl zirconium η$^4$-1,4-dinaphthyl-1,3-butadiene;
N-methylpiperazinoborane-bis-η$^5$-n-butylcyclopentadienyl zirconium η$^4$-1-phenyl-1,3-pentadiene;
N-methylpiperazinoborane-bis-η$^5$-n-butylcyclopentadienyl zirconium η$^4$-1,3-pentadiene;
N-methylpiperazinoborane-bis-η$^5$-inden-1-ylzirconium η$^4$-1,4-diphenyl-1,3-butadiene;
N-methylpiperazinoborane-bis-η$^5$-inden-1-ylzirconium η$^4$-2,4-hexadiene;
N-methylpiperazinoborane-bis-η$^5$-inden-1-ylzirconium η$^4$-1,4-dinaphthyl-1,3-butadiene;
N-methylpiperazinoborane-bis-η$^5$-inden-1-ylzirconium η$^4$-phenyl-1,3-pentadiene;
N-methylpiperazinoborane-bis-η$^5$-inden-1-ylzirconium η$^4$-1,3-pentadiene;
N-methylpiperazinoborane-bis-η$^5$-(2-methylinden-1-yl)zirconium -η$^4$-1,4-diphenyl-1,3-butadiene;
N-methylpiperazinoborane-bis-η$^5$-(2-methylinden-1-yl)zirconium η$^4$-2,4-hexadiene;
N-methylpiperazinoborane-bis-η$^5$-(2-methylinden-1-yl)zirconium η$^4$-1,4-dinaphthyl-1,3-butadiene;
N-methylpiperazinoborane-bis-η$^5$-(2-methylinden-1-yl)zirconium η$^4$-1-phenyl-1,3-pentadiene;
N-methylpiperazinoborane-bis-η$^5$-(2-methylinden-1-yl)zirconium η$^4$-1,3-pentadiene;
N-methylpiperazinoborane-bis-η$^5$-(2-methyl-4-phenylinden-1-yl)zirconium η$^4$-1,4-diphenyl-1,3-butadiene;
N-methylpiperazinoborane-bis-η$^5$-(2-methyl-4-phenylinden-1-yl)zirconium η$^4$-2,4-hexadiene;
N-methylpiperazinoborane-bis-η$^5$-(2-methyl-4-phenylinden-1-yl)zirconium η$^4$-1,4-dinaphthyl-1,3-butadiene;
N-methylpiperazinoborane-bis-η$^5$-(2-methyl-4-phenylinden-1-yl)zirconium η$^4$-1-phenyl-1,3-pentadiene;
N-methylpiperazinoborane-bis-η$^5$-(2-methyl-4-phenylinden-1-yl)zirconium η$^4$-1,3-pentadiene;
N-methylpiperazinoborane-bis-η$^5$-(2-ethyl-4-phenylinden-1-yl)zirconium η$^4$-1,4-diphenyl-1,3-butadiene;
N-methylpiperazinoborane-bis-η$^5$-(2-ethyl-4-phenylinden-1-yl)zirconium η$^4$-2,4-hexadiene;
N-methylpiperazinoborane-bis-η$^5$-(2-ethyl-4-phenylinden-1-yl)zirconium η$^4$-1,4-dinaphthyl-1,3-butadiene;
N-methylpiperazinoborane-bis-η$^5$-(2-ethyl-4-phenylinden-1-yl)zirconium η$^4$-1-phenyl-1,3-pentadiene;
N-methylpiperazinoborane-bis-η$^5$-(2-ethyl-4-phenylinden-1-yl)zirconium η$^4$-1,3-pentadiene;
N-methylpiperazinoborane-bis-η$^5$-(2-isopropyl-4-phenylinden-1-yl)zirconium η$^4$-1,4-diphenyl-1,3-butadiene;
N-methylpiperazinoborane-bis-η$^5$-(2-isopropyl-4-phenylinden-1-yl)zirconium η$^4$-2,4-hexadiene;
N-methylpiperazinoborane-bis-η$^5$-(2-isopropyl-4-phenylinden-1-yl)zirconium η$^4$-1,4-dinaphthyl-1,3-butadiene;
N-methylpiperazinoborane-bis-η$^5$-(2-isopropyl-4-phenylinden-1-yl)zirconium η$^4$-1-phenyl-1,3-pentadiene;
N-methylpiperazinoborane-bis-η$^5$-(2-isopropyl-4-phenylinden-1-yl)zirconium η$^4$-1,3-pentadiene;
N-methylpiperazinoborane-bis-η$^5$-(2-methyl-4-naphthylinden-1-yl)zirconium η$^4$-1,4-diphenyl-1,3-butadiene;
N-methylpiperazinoborane-bis-η$^5$-(2-methyl-4-naphthylinden-1-yl)zirconium η$^4$-2,4-hexadiene;
N-methylpiperazinoborane-bis-η$^5$-(2-methyl-4-naphthylinden-1-yl)zirconium η$^4$-1,4-dinaphthyl-1,3-butadiene;
N-methylpiperazinoborane-bis-η$^5$-(2-methyl-4-naphthylinden-1-yl)zirconium η$^4$-1-phenyl-1,3-pentadiene;

N-methylpiperazinoborane-bis-$\eta^5$-(2-methyl-4-naphthylinden-1-yl)zirconium $\eta^4$-1,3-pentadiene;
N-methylpiperazinoborane-bis-$\eta^5$-(2-methyl-4-bis(3,5-trifluoromethyl)phenylinden-1-yl)zirconium $\eta^4$-1,4-diphenyl-1,3-butadiene;
N-methylpiperazinoborane-bis-$\eta^5$-(2-methyl-4-bis(3,5-trifluoromethyl)phenylinden-1-yl)zirconium $\eta^4$-2,4-hexadiene;
N-methylpiperazinoborane-bis-$\eta^5$-(2-methyl-4-bis(3,5-trifluoromethyl)phenylinden-1-yl)zirconium $\eta^4$-1,4-dinaphthyl-1,3-butadiene;
N-methylpiperazinoborane-bis-$\eta^5$(2-methyl-4-bis(3,5-trifluoromethyl)phenylinden-1-yl)zirconium $\eta^4$-1-phenyl-1,3-pentadiene;
N-methylpiperazinoborane-bis-$\eta^5$-(2-methyl-4-bis(3,5-trifluoromethyl)phenylinden-1-yl)zirconium $\eta^4$-1,3-pentadiene;
N-methylpiperazinoborane-bis-$\eta^5$-(2-ethyl-4-bis(3,5-trifluoromethyl)phenylinden-1-yl)zirconium $\eta^4$-1,4-diphenyl-1,3-butadiene;
N-methylpiperazinoborane-bis-$\eta^5$-(2-ethyl-4-bis(3,5-trifluoromethyl)phenylinden-1-yl)zirconium $\eta^4$-2,4-hexadiene;
N-methylpiperazinoborane-bis-$\eta^5$-(2-ethyl-4-bis(3,5-trifluoromethyl)phenylinden-1-yl)zirconium $\eta^4$-1,4-dinaphthyl-1,3-butadiene;
N-methylpiperazinoborane-bis-$\eta^5$-(2-ethyl-4-bis(3,5-trifluoromethyl)phenylinden-1-yl)zirconium $\eta^4$-1-phenyl-1,3-pentadiene;
N-methylpiperazinoborane-bis-$\eta^5$-(2-ethyl-4-bis(3,5-trifluoromethyl)phenylinden-1-yl)zirconium $\eta^4$-1,3-pentadiene;
N-methylpiperazinoborane-bis-$\eta^5$-(2-isopropyl-4-bis(3,5-trifluoromethyl)phenylinden-1-yl)zirconium $\eta^4$-1,4-diphenyl-1,3-butadiene;
N-methylpiperazinoborane-bis-$\eta^5$-(2-isopropyl-4-bis(3,5-trifluoromethyl)phenylinden-1-yl)zirconium $\eta^4$-2,4-hexadiene;
N-methylpiperazinoborane-bis-$\eta^5$-(2-isopropyl-4-bis(3,5-trifluoromethyl)phenylinden-1-yl)zirconium $\eta^4$-1,4-dinaphthyl-1,3-butadiene;
N-methylpiperazinoborane-bis-$\eta^5$-(2-isopropyl-4-bis(3,5-trifluoromethyl)phenylinden-1-yl)zirconium $\eta^4$-1-phenyl-1,3-pentadiene;
N-methylpiperazinoborane-bis-$\eta^5$-(2-isopropyl-4-bis(3,5-trifluoromethyl)phenylinden-1-yl)zirconium $\eta^4$-1,3-pentadiene;
N-methylpiperazinoborane-bis-$\eta^5$-(3-isopropylinden-1-yl)zirconium $\eta^4$-1,4-diphenyl-1,3-butadiene;
N-methylpiperazinoborane-bis-$\eta^5$-(3-isopropylinden-1-yl)zirconium $\eta^4$-2,4-hexadiene;
N-methylpiperazinoborane-bis-$\eta^5$-(3-isopropylinden-1-yl)zirconium $\eta^4$-1,4-dinaphthyl-1,3-butadiene;
N-methylpiperazinoborane-bis-$\eta^5$-(3-isopropylinden-1-yl)zirconium $\eta^4$-1-phenyl-1,3-pentadiene;
N-methylpiperazinoborane-bis-$\eta^5$-(3-isopropylinden-1-yl)zirconium $\eta^4$-1,3-pentadiene;
N-methylpiperazinoborane-bis-$\eta^5$-(3-t-butylinden-1-yl)zirconium $\eta^4$-1,4-diphenyl-1,3-butadiene;
N-methylpiperazinoborane-bis-$\eta^5$-(3-t-butylinden-1-yl)zirconium $\eta^4$-2,4-hexadiene;
N-methylpiperazinoborane-bis-$\eta^5$-(3-t-butylinden-1-yl)zirconium $\eta^4$-1,4-dinaphthyl-1,3-butadiene;
N-methylpiperazinoborane-bis-$\eta^5$-(3-t-butylinden-1-yl)zirconium $\eta^4$-1-phenyl-1,3-pentadiene;
N-methylpiperazinoborane-bis-$\eta^5$-(3-t-butylinden-1-yl)zirconium $\eta^4$-1,3-pentadiene;
morpholinoborane-bis-$\eta^5$-cyclopentadienyl zirconium $\eta^4$-1,4-diphenyl-1,3-butadiene;
morpholinoborane-bis-$\eta^5$-cyclopentadienyl zirconium $\eta^4$-2,4-hexadiene;
morpholinoborane-bis-$\eta^5$-cyclopentadienyl zirconium $\eta^4$-1,4-dinaphthyl-1,3-butadiene;
morpholinoborane-bis-$\eta^5$-cyclopentadienyl zirconium $\eta^4$-1-phenyl-1,3-pentadiene;
morpholinoborane-bis-$\eta^5$-cyclopentadienyl zirconium $\eta^5$-1,3-pentadiene;
morpholinoborane-bis-$\eta^5$-n-butylcyclopentadienyl zirconium $\eta^4$-1,4-diphenyl-1,3-butadiene;
morpholinoborane-bis-$\eta^5$-n-butylcyclopentadienyl zirconium $\eta^4$-2,4-hexadiene;
morpholinoborane-bis-$\eta^5$-n-butylcyclopentadienyl zirconium $\eta^4$-1,4-dinaphthyl-1,3-butadiene;
morpholinoborane-bis-$\eta^5$-n-butylcyclopentadienyl zirconium $\eta^4$-1-phenyl-1,3-pentadiene;
morpholinoborane-bis-$\eta^5$-n-butylcyclopentadienyl zirconium $\eta^4$-1,3-pentadiene;
morpholinoborane-bis-$\eta^5$-inden-1-ylzirconium $\eta^4$-1,4-diphenyl-1,3-butadiene;
morpholinoborane-bis-$\eta^5$-inden-1-ylzirconium $\eta^4$-2,4-hexadiene;
morpholinoborane-bis-$\eta^5$-inden-1-ylzirconium $\eta^4$-1,4-dinaphthyl-1,3-butadiene;
morpholinoborane-bis-$\eta^5$-inden-1-ylzirconium $\eta^4$-1-phenyl-1,3-pentadiene;
morpholinoborane-bis-$\eta^5$-inden-1-ylzirconium $\eta^4$-1,3-pentadiene;
morpholinoborane-bis-$\eta^5$-(2-methylinden-1-yl)zirconium $\eta^4$-1,4-diphenyl-1,3-butadiene;
morpholinoborane-bis-$\eta^5$-(2-methylinden-1-yl)zirconium $\eta^4$-2,4-hexadiene;
morpholinoborane-bis-$\eta^5$-(2-methylinden-1-yl)zirconium $\eta^4$-1,4-dinaphthyl-1,3-butadiene;
morpholinoborane-bis-$\eta^5$-(2-methylinden-1-yl)zirconium $\eta^4$-1-phenyl-1,3-pentadiene;
morpholinoborane-bis-$\eta^5$-(2-methylinden-1-yl)zirconium $\eta^4$-1,3-pentadiene;
morpholinoborane-bis-$\eta^5$-(2-methyl-4-phenylinden-1-yl)zirconium $\eta^4$-1,4-diphenyl-1,3-butadiene;
morpholinoborane-bis-$\eta^5$-(2-methyl-4-phenylinden-1-yl)zirconium $\eta^4$-2,4-hexadiene;
morpholinoborane-bis-$\eta^5$-(2-methyl-4-phenylinden-1-yl)zirconium $\eta^4$-1,4-dinaphthyl-1,3-butadiene;
morpholinoborane-bis-$\eta^5$-(2-methyl-4-phenylinden-1-yl)zirconium $\eta^4$-1-phenyl-1,3-pentadiene;
morpholinoborane-bis-$\eta^5$-(2-methyl-4-phenylinden-1-yl)zirconium $\eta^4$-1,3-pentadiene;
morpholinoborane-bis-$\eta^5$-(2-ethyl-4-phenylinden-1-yl)zirconium $\eta^4$-1,4-diphenyl-1,3-butadiene;
morpholinoborane-bis-$\eta^5$-(2-ethyl-4-phenylinden-1-yl)zirconium $\eta^4$-2,4-hexadiene;
morpholinoborane-bis-$\eta^5$-(2-ethyl-4-phenylinden-1-yl)zirconium $\eta^4$-1,4-dinaphthyl-1,3-butadiene;
morpholinoborane-bis-$\eta^5$-(2-ethyl-4-phenylinden-1-yl)zirconium $\eta^4$-1-phenyl-1,3-pentadiene;
morpholinoborane-bis-$\eta^5$-(2-ethyl-4-phenylinden-1-yl)zirconium $\eta^4$-1,3-pentadiene;
morpholinoborane-bis-$\eta^5$-(2-isopropyl-4-phenylinden-1-yl)zirconium $\eta^4$-1,4-diphenyl-1,3-butadiene;
morpholinoborane-bis-$\eta^5$-(2-isopropyl-4-phenylinden-1-yl)zirconium $\eta^4$-2,4-hexadiene;
morpholinoborane-bis-$\eta^5$-(2-isopropyl-4-phenylinden-1-yl)zirconium $\eta^4$-1,4-dinaphthyl-1,3-butadiene;
morpholinoborane-bis-$\eta^5$-(2-isopropyl-4-phenylinden-1-yl)zirconium $\eta^4$-1-phenyl-1,3-pentadiene;

morpholinoborane-bis-$\eta^5$-(2-isopropyl-4-phenylinden-1-yl) zirconium $\eta^4$-1,3-pentadiene;
morpholinoborane-bis-$\eta^5$-(2-methyl-4-naphthylinden-1-yl) zirconium $\eta^4$-1,4-diphenyl-1,3-butadiene;
morpholinoborane-bis-$\eta^5$-(2-methyl-4-naphthylinden 1-yl) zirconium $\eta^4$-2,4-hexadiene;
morpholinoborane-bis-$\eta^5$-(2-methyl-4-naphthylinden-1-yl) zirconium $\eta^4$-1,4-dinaphthyl-1,3-butadiene;
morpholinoborane-bis-$\eta^5$-(2-methyl-4-naphthylinden-1-yl) zirconium $\eta^4$-1-phenyl-1,3-pentadiene;
morpholinoborane-bis-$\eta^5$-(2-methyl-4-naphthylinden-1-yl) zirconium $\eta^4$-1,3-pentadiene;
morpholinoborane-bis-$\eta^5$-(2-methyl-4-bis(3,5-trifluoromethyl)phenylinden-1-yl)zirconium $\eta^4$-1,4-diphenyl-1,3-butadiene;
morpholinoborane-bis-$\eta^5$-(2-methyl-4-bis(3,5-trifluoromethyl)phenylinden-1-yl)zirconium $\eta^4$-2,4-hexadiene;
morpholinoborane-bis-$\eta^5$-(2-methyl-4-bis(3,5-trifluoromethyl)phenylinden-1-yl)zirconium $\eta^4$-1,4-dinaphthyl-1,3-butadiene;
morpholinoborane-bis-$\eta^5$-(2-methyl-4-bis(3,5-trifluoromethyl)phenylinden-1-yl)zirconium $\eta^4$-1-phenyl-1,3-pentadiene ;
morpholinoborane-bis-$\eta^5$-(2-methyl-4-bis(3,5-trifluoromethyl)phenylinden-1-yl)zirconium $\eta^4$-1,3-pentadiene;
morpholinoborane-bis-$\eta^5$-(2-ethyl-4-bis(3,5-trifluoromethyl)phenylinden-1-yl)zirconium $\eta^4$-1,4-diphenyl-1,3-butadiene;
morpholinoborane-bis-$\eta^5$-(2-ethyl-4-bis(3,5-trifluoromethyl)phenylinden-1-yl)zirconium $\eta^4$-2,4-hexadiene;
morpholinoborane-bis-$\eta^5$-(2-ethyl-4-bis(3,5-trifluoromethyl)phenylinden-1-yl)zirconium $\eta^4$-1,4-dinaphthyl-1,3-butadiene;
morpholinoborane-bis-$\eta^5$-(2-ethyl-4-bis(3,5-trifluoromethyl)phenylinden-1-yl)zirconium $\eta^4$-1-phenyl-1,3-pentadiene;
morpholinoborane-bis-$\eta^5$-(2-ethyl-4-bis(3,5-trifluoromethyl)phenylinden-1-yl)zirconium $\eta^4$-1,3-pentadiene;
morpholinoborane-bis-$\eta^5$-(2-isopropyl-4-bis(3,5-trifluoromethyl)phenylinden-1-yl)zirconium $\eta^4$-1,4-diphenyl-1,3-butadiene;
morpholinoborane-bis-$\eta^5$-(2-isopropyl-4-bis(3,5-trifluoromethyl)phenylinden-1-yl)zirconium $\eta^4$-2,4-hexadiene;
morpholinoborane-bis-$\eta^5$-(2-isopropyl-4-bis(3,5-trifluoromethyl)phenylinden-1-yl)zirconium $\eta^4$-1,4-dinaphthyl-1,3-butadiene;
morpholinoborane-bis-$\eta^5$-(2-isopropyl-4-bis(3,5-trifluoromethyl)phenylinden-1-yl)zirconium $\eta^4$-1-phenyl-1,3-pentadiene;
morpholinoborane-bis-$\eta^5$-(2-isopropyl-4-bis(3,5-trifluoromethyl)phenylinden-1-yl)zirconium $\eta^4$-1,3-pentadiene;
morpholinoborane-bis-$\eta^5$-(3-isopropylinden-1-yl) zirconium $\eta^4$-1,4-diphenyl-1,3-butadiene;
morpholinoborane-bis-$\eta^5$-(3-isopropylinden-1-yl) zirconium $\eta^4$-2,4-hexadiene;
morpholinoborane-bis-$\eta^5$-(3-isopropylinden-1-yl) zirconium $\eta^4$-1,4-dinaphthyl-1,3-butadiene;
morpholinoborane-bis-$\eta^5$-(3-isopropylinden-1-yl) zirconium $\eta^4$-3-phenyl-1,3-pentadiene;
morpholinoborane-bis-$\eta^5$-(3-isopropylinden-1-yl) zirconium $\eta^4$-1,3-pentadiene;
morpholinoborane-bis-$\eta^5$-(3-t-butylinden-1-yl)zirconium $\eta^4$-1,4-diphenyl-1,3-butadiene;
morpholinoborane-bis-$\eta^5$-(3-t-butylinden-1-yl)zirconium $\eta^4$-2,4-hexadiene;
morpholinoborane-bis-$\eta^5$-(3-t-butylinden-1-yl)zirconium $\eta^4$-1,4-dinaphthyl-1,3-butadiene;
morpholinoborane-bis-$\eta^5$-(3-t-butylinden-1-yl)zirconium $\eta^4$-1-phenyl-1,3-pentadiene; and
morpholinoborane-bis-$\eta^5$-(3-t-butylinden-1-yl)zirconium $\eta^4$-1,3-pentadiene.

Specific, but not limiting examples of metal complexes of formula 1 and formula 1' wherein M is in the +4 formal oxidation state are:
dimethylamidoborane-bis-$\eta^5$-cyclopentadienyl zirconium dichloride;
dimethylamidoborane-bis-$\eta^5$-cyclopentadienyl zirconium dimethyl;
dimethylamidoborane-bis-$\eta^5$-cyclopentadienyl zirconium dibenzyl;
dimethylamidoborane-bis-$\eta^5$-cyclopentadienyl zirconium bis(trimethylsilyl);
dimethylamidoborane-bis-$\eta^5$-cyclopentadienyl zirconium-2,3-dimethyl-2-butene-1,4-diyl;
dimethylamidoborane-bis-$\eta^5$-n-butylcyclopentadienyl zirconium dichloride;
dimethylamidoborane-bis-$\eta^5$-n-butylcyclopentadienyl zirconium dimethyl;
dimethylamidoborane-bis-$\eta^5$-n-butylcyclopentadienyl zirconium dibenzyl;
dimethylamidoborane-bis-$\eta^5$-n-butylcyclopentadienyl zirconium bis(trimethylsilyl);
dimethylamidoborane-bis-$\eta^5$-n-butylcyclopentadienyl zirconium-2,3-dimethyl-2-butene-1,4-diyl;
dimethylamidoborane-bis-$\eta^5$-inden-1-yl zirconium dichloride;
dimethylamidoborane-bis-$\eta^5$-inden-1-yl zirconium dimethyl;
dimethylamidoborane-bis-$\eta^5$-inden-1-yl zirconium dibenzyl;
dimethylamidoborane-bis-$\eta^5$-inden-1-yl zirconium bis(trimethylsilyl);
dimethylamidoborane-bis-$\eta^5$-inden-1-yl zirconium-2,3-dimethyl-2-butene-1,4-diyl;
dimethylamidoborane-bis-$\eta^5$-2-methylinden-1-yl zirconium dichloride;
dimethylamidoborane-bis-$\eta^5$-2-methylinden-1-yl zirconium dimethyl;
dimethylamidoborane-bis-$\eta^5$-2-methylinden-1-yl zirconium dibenzyl;
dimethylamidoborane-bis-$\eta^5$-2-methylinden-1-yl zirconium bis(trimethylsilyl);
dimethylamidoborane-bis-$\eta^5$-2-methylinden-1-yl zirconium-2,3-dimethyl-2-butene-1,4-diyl;
dimethylamidoborane-bis-$\eta^5$-(2-methyl-4-phenylinden-1-yl)zirconium dichloride;
dimethylamidoborane-bis-$\eta^5$-(2-methyl-4-phenylinden-1-yl)zirconium dimethyl;
dimethylamidoborane-bis-$\eta^5$-(2-methyl-4-phenylinden-1-yl)zirconium dibenzyl;
dimethylamidoborane-bis-$\eta^5$-(2-methyl-4-phenylinden-1-yl)zirconium bis(trimethylsilyl);
dimethylamidoborane-bis-$\eta^5$-(2-methyl-4-phenylinden-1-yl)zirconium -2,3-dimethyl-2-butene-1,4-diyl;
dimethylamidoborane-bis-$\eta^5$-(2-ethyl-4-phenylinden-1-yl) zirconium dichloride;
dimethylamidoborane-bis-$\eta^5$-(2-ethyl-4-phenylinden-1-yl) zirconium dimethyl;

dimethylamidoborane-bis-$\eta^5$-(2-ethyl-4-phenylinden-1-yl) zirconium dibenzyl;
dimethylamidoborane-bis-$\eta^5$-(2-ethyl-4-phenylinden-1-yl) zirconium bis(trimethylsilyl);
dimethylamidoborane-bis-$\eta^5$-(2-ethyl-4-phenylinden-1-yl) zirconium-2,3-dimethyl-2-butene-1,4-diyl;
dimethylamidoborane-bis-$\eta^5$-(2-isopropyl-4-phenylinden-1-yl)zirconium dichloride;
dimethylamidoborane-bis-$\eta^5$-(2-isopropyl-4-phenylinden-1-yl)zirconium dimethyl;
dimethylamidoborane-bis-$\eta^5$-(2-isopropyl-4-phenylinden-1-yl)zirconium dibenzyl;
dimethylamidoborane-bis-$\eta^5$-(2-isopropyl-4-phenylinden-1-yl)zirconium bis(trimethylsilyl);
dimethylamidoborane-bis-$\eta^5$-(2-isopropyl-4-phenylinden-1-yl)zirconium-2,3-dimethyl-2-butene-1,4-diyl;
dimethylamidoborane-bis-$\eta^5$-(2-methyl-4-naphthylinden-1-yl)zirconium dichloride;
dimethylamidoborane-bis-$\eta^5$-(2-methyl-4-naphthylinden-1-yl)zirconium dimethyl;
dimethylamidoborane-bis-$\eta^5$-(2-methyl-4-naphthylinden-1-yl)zirconium dibenzyl;
dimethylamidoborane-bis-$\eta^5$-(2-methyl-4-naphthylinden-1-yl)zirconium bis(trimethylsilyl);
dimethylamidoborane-bis-$\eta^5$-(2-methyl-4-naphthylinden-1-yl)zirconium-2,3-dimethyl-2-butene-1,4-diyl;
dimethylamidoborane-bis-$\eta^5$-(2-methyl-4-bis(3,5-trifluoromethyl)phenylinden-1-yl)zirconium dichloride;
dimethylamidoborane-bis-$\eta^5$-(2-methyl-4-bis(3,5-trifluoromethyl)phenylinden-1-yl)zirconium dimethyl;
dimethylamidoborane-bis-$\eta^5$-(2-methyl-4-bis(3,5-trifluoromethyl)phenylinden-1-yl)zirconium dibenzyl;
dimethylamidoborane-bis-$\eta^5$-(2-methyl-4-bis(3,5-trifluoromethyl)phenylinden-1-yl)zirconium bis(trimethylsilyl);
dimethylamidoborane-bis-$\eta^5$-(2-methyl-4-bis(3,5-trifluoromethyl)phenylinden-1-yl)zirconium-2,3-dimethyl-2-butene-1,4-diyl;
dimethylamidoborane-bis-$\eta^5$-(2-ethyl-4-bis(3,5-trifluoromethyl)phenylinden-1-yl)zirconium dichloride;
dimethylamidoborane-bis-$\eta^5$-(2-ethyl-4-bis(3,5-trifluoromethyl)phenylinden-1-yl)zirconium dimethyl;
dimethylamidoborane-bis-$\eta^5$-(2-ethyl-4-bis(3,5-trifluoromethyl)phenylinden-1-yl)zirconium dibenzyl;
dimethylamidoborane-bis-$\eta^5$-(2-ethyl-4-bis(3,5-trifluoromethyl)phenylinden-1-yl)zirconium bis(trimethylsilyl);
dimethylamidoborane-bis-$\eta^5$-(2-ethyl-4-bis(3,5-trifluoromethyl)phenylinden-1-yl)zirconium-2,3-dimethyl-2-butene-1,4-diyl;
dimethylamidoborane-bis-$\eta^5$-(2-isopropyl-4-bis(3,5-trifluoromethyl)phenylinden-1-yl)zirconium dichloride;
dimethylamidoborane-bis-$\eta^5$-(2-isopropyl-4-bis(3,5-trifluoromethyl)phenylinden-1-yl)zirconium dimethyl;
dimethylamidoborane-bis-$\eta^5$-(2-isopropyl-4-bis(3,5-trifluoromethyl)phenylinden-1-yl)zirconium dibenzyl;
dimethylamidoborane-bis-$\eta^5$-(2-isopropyl-4-bis(3,5-trifluoromethyl)phenylinden-1-yl)zirconium bis(trimethylsilyl);
dimethylamidoborane-bis-$\eta^5$-(2-isopropyl-4-bis(3,5-trifluoromethyl)phenylinden-1-yl)zirconium-2,3-dimethyl-2-butene-1,4-diyl;
dimethylamidoborane-bis-$\eta^5$-(3-isopropylinden-1-yl) zirconium dichloride;
dimethylamidoborane-bis-$\eta^5$-(3-isopropylinden-1-yl) zirconium dimethyl;
dimethylamidoborane-bis-$\eta^5$-(3-isopropylinden-1-yl) zirconium dibenzyl;
dimethylamidoborane-bis-$\eta^5$-(3-isopropylinden-1-yl) zirconium bis(trimethylsilyl);
dimethylamidoborane-bis-$\eta^5$-(3-isopropylinden-1-yl) zirconium-2,3-dimethyl-2-butene-1,4-diyl;
dimethylamidoborane-bis-$\eta^5$-(3-t-butylinden-1-yl) zirconium dichloride;
dimethylamidoborane-bis-$\eta^5$-(3-t-butylinden-1-yl) zirconium dimethyl;
dimethylamidoborane-bis-$\eta^5$-(3-t-butylinden-1-yl) zirconium dibenzyl;
dimethylamidoborane-bis-$\eta^5$-(3-t-butylinden-1-yl) zirconium bis(trimethylsilyl);
dimethylamidoborane-bis-$\eta^5$-(3-t-butylinden-1-yl) zirconium-2,3-dimethyl-2-butene-1,4-diyl;
diisopropylamidoborane-bis-$\eta^5$-cyclopentadienyl zirconium dichloride;
diisopropylamidoborane-bis-$\eta^5$-cyclopentadienyl zirconium dimethyl;
diisopropylamidoborane-bis-$\eta^5$-cyclopentadienyl zirconium dibenzyl;
diisopropylamidoborane-bis-$\eta^5$-cyclopentadienyl zirconium bis(trimethylsilyl);
diisopropylamidoborane-bis-$\eta^5$-cyclopentadienyl zirconium-2,3-dimethyl-2-butene-1,4-diyl;
diisopropylamidoborane-bis-$\eta^5$-n-butylcyclopentadienyl zirconium dichloride;
diisopropylamidoborane-bis-$\eta^5$-n-butylcyclopentadienyl zirconium dimethyl;
diisopropylamidoborane-bis-$\eta^5$-n-butylcyclopentadienyl zirconium dibenzyl;
diisopropylamidoborane-bis-$\eta^5$-n-butylcyclopentadienyl zirconium bis(trimethylsilyl);
diisopropylamidoborane-bis-$\eta^5$-n-butylcyclopentadienyl zirconium-2,3-dimethyl-2-butene-1,4-diyl;
diisopropylamidoborane-bis-$\eta^5$-inden-1-yl zirconium dichloride;
diisopropylamidoborane-bis-$\eta^5$-inden-1-yl zirconium dimethyl;
diisopropylamidoborane-bis-$\eta^5$-inden-1-yl zirconium dibenzyl;
diisopropylamidoborane-bis-$\eta^5$-inden-1-yl zirconium bis (trimethylsilyl);
diisopropylamidoborane-bis-$\eta^5$-inden-1-yl zirconium-2,3-dimethyl-2-butene-1,4-diyl;
diisopropylamidoborane-bis-$\eta^5$-2-methylinden-1-yl zirconium dichloride;
diisopropylamidoborane-bis-$\eta^5$-2-methylinden-1-yl zirconium dimethyl;
diisopropylamidoborane-bis-$\eta^5$-2-methylinden-1-yl zirconium dibenzyl;
diisopropylamidoborane-bis-$\eta^5$-2-methylinden-1-yl zirconium bis(trimethylsilyl);
diisopropylamidoborane-bis-$\eta^5$-2-methylinden-1-yl zirconium-2,3-dimethyl-2-butene-1,4-diyl;
diisopropylamidoborane-bis-$\eta^5$-(2-methyl-4-phenylinden-1-yl)zirconium dichloride;
diisopropylamidoborane-bis-$\eta^5$-(2-methyl-4-phenylinden-1-yl)zirconium dimethyl;
diisopropylamidoborane-bis-$\eta^5$-(2-methyl-4-phenylinden-1-yl)zirconium dibenzyl;
diisopropylamidoborane-bis-$\eta^5$-(2-methyl-4-phenylinden-1-yl)zirconium bis(trimethylsilyl);
diisopropylamidoborane-bis-$\eta^5$-(2-methyl-4-phenylinden-1-yl)zirconium -2,3-dimethyl-2-butene-1,4-diyl;
diisopropylamidoborane-bis-$\eta^5$-(2-ethyl-4-phenylinden-1-yl)zirconium dichloride;
diisopropylamidoborane-bis-$\eta^5$-(2-ethyl-4-phenylinden-1-yl)zirconium dimethyl;

diisopropylamidoborane-bis-$\eta^5$-(2-ethyl-4-phenylinden-1-yl)zirconium dibenzyl;
diisopropylamidoborane-bis-$\eta^5$-(2-ethyl-4-phenylinden-1-yl)zirconium bis(trimethylsilyl);
diisopropylamidoborane-bis-$\eta^5$-(2-ethyl-4-phenylinden-1-yl)zirconium-2,3-dimethyl-2-butene-1,4-diyl;
diisopropylamidoborane-bis-$\eta^5$-(2-isopropyl-4-phenylinden-1-yl)zirconium dichloride;
diisopropylamidoborane-bis-$\eta^5$-(2-isopropyl-4-phenylinden-1-yl)zirconium dimethyl;
diisopropylamidoborane-bis-$\eta^5$-(2-isopropyl-4-phenylinden-1-yl)zirconium dibenzyl;
diisopropylamidoborane-bis-$\eta^5$-(2-isopropyl-4-phenylinden-1-yl)zirconium
diisopropylamidoborane-bis-$\eta^5$-(2-isopropyl-4-phenylinden-1-yl)zirconium bis(trimethylsilyl);
diisopropylamidoborane-bis-$\eta^5$-(2-isopropyl-4-phenylinden-1-yl)zirconium-2,3-dimethyl-2-butene-1,4-diyl;
diisopropylamidoborane-bis-$\eta^5$-(2-methyl-4-naphthylinden-1-yl)zirconium dichloride;
diisopropylamidoborane-bis-$\eta^5$-(2-methyl-4-naphthylinden-1-yl)zirconium dimethyl;
diisopropylamidoborane-bis-$\eta^5$-(2-methyl-4-naphthylinden-1-yl)zirconium dibenzyl;
diisopropylamidoborane-bis-$\eta^5$-(2-methyl-4-naphthylinden-1-yl)zirconium bis(trimethylsilyl);
diisopropylamidoborane-bis-$\eta^5$-(2-methyl-4-naphthylinden-1-yl)zirconium-2,3-dimethyl-2-butene-1,4-diyl;
diisopropylamidoborane-bis-$\eta^5$-(2-methyl-4-bis(3,5-trifluoromethyl)phenylinden-1-yl)zirconium dichloride;
diisopropylamidoborane-bis-$\eta^5$-(2-methyl-4-bis(3,5-trifluoromethyl)phenylinden-1-yl)zirconium dimethyl;
diisopropylamidoborane-bis-$\eta^5$-(2-methyl-4-bis(3,5-trifluoromethyl)phenylinden-1-yl)zirconium dibenzyl;
diisopropylamidoborane-bis-$\eta^5$-(2-methyl-4-bis(3,5-trifluoromethyl)phenylinden-1-yl)zirconium bis(trimethylsilyl);
diisopropylamidoborane-bis-$\eta^5$-(2-methyl-4-bis(3,5-trifluoromethyl)phenylinden-1-yl)zirconium-2,3-dimethyl-2-butene-1,4-diyl;
diisopropylamidoborane-bis-$\eta^5$-(2-ethyl-4-bis(3,5-trifluoromethyl)phenylinden-1-yl)zirconium dichloride;
diisopropylamidoborane-bis-$\eta^5$-(2-ethyl-4-bis(3,5-trifluoromethyl)phenylinden-1-yl)zirconium dimethyl;
diisopropylamidoborane-bis-$\eta^5$-(2-ethyl-4-bis(3,5-trifluoromethyl)phenylinden-1-yl)zirconium dibenzyl;
diisopropylamidoborane-bis-$\eta^5$-(2-ethyl-4-bis(3,5-trifluoromethyl)phenylinden-1-yl)zirconium bis(trimethylsilyl);
diisopropylamidoborane-bis-$\eta^5$-(2-ethyl-4-bis(3,5-trifluoromethyl)phenylinden-1-yl)zirconium-2,3-dimethyl-2-butene-1,4-diyl;
diisopropylamidoborane-bis-$\eta^5$-(2-isopropyl-4-bis(3,5-trifluoromethyl)phenylinden-1-yl)zirconium dichloride;
diisopropylamidoborane-bis-$\eta^5$-(2-isopropyl-4-bis(3,5-trifluoromethyl)phenylinden-1-yl)zirconium dimethyl;
diisopropylamidoborane-bis-$\eta^5$-(2-isopropyl-4-bis(3,5-trifluoromethyl)phenylinden-1-yl)zirconium dibenzyl;
diisopropylamidoborane-bis-$\eta^5$-(2-isopropyl-4-bis(3,5-trifluoromethyl)phenylinden-1-yl)zirconium bis(trimethylsilyl);
diisopropylamidoborane-bis-$\eta^5$-(2-isopropyl-4-bis(3,5-trifluoromethyl)phenylinden-1-yl)zirconium-2,3-dimethyl-2-butene-1,4-diyl;
diisopropylamidoborane-bis-$\eta^5$-(3-isopropylinden-1-yl)zirconium dichloride;
diisopropylamidoborane-bis-$\eta^5$-(3-isopropylinden-1-yl)zirconium dimethyl;
diisopropylamidoborane-bis-$\eta^5$-(3-isopropylinden-1-yl)zirconium dibenzyl;
diisopropylamidoborane-bis-$\eta^5$-(3-isopropylinden-1-yl)zirconium bis(trimethylsilyl);
diisopropylamidoborane-bis-$\eta^5$-(3-isopropylinden-1-yl)zirconium-2,3-dimethyl-2-butene-1,4-diyl;
diisopropylamidoborane-bis-$\eta^5$-(3-t-butylinden-1-yl)zirconium dichloride;
diisopropylamidoborane-bis-$\eta^5$-(3-t-butylinden-1-yl)zirconium dimethyl;
diisopropylamidoborane-bis-$\eta^5$-(3-t-butylinden-1-yl)zirconium dibenzyl;
diisopropylamidoborane-bis-$\eta^5$-(3-t-butylinden-1-yl)zirconium bis(trimethylsilyl);
diisopropylamidoborane-bis-$\eta^5$-(3-t-butylinden-1-yl)zirconium-2,3-dimethyl-2-butene-1,4-diyl;
diphenylamidoborane-bis-$\eta^5$-cyclopentadienyl zirconium dichloride;
diphenylamidoborane-bis-$\eta^5$-cyclopentadienyl zirconium dimethyl;
diphenylamidoborane-bis-$\eta^5$-cyclopentadienyl zirconium dibenzyl;
diphenylamidoborane-bis-$\eta^5$-cyclopentadienyl zirconium bis(trimethylsilyl);
diphenylamidoborane-bis-$\eta^5$-cyclopentadienyl zirconium-2,3-dimethyl-2-butene-1,4-diyl;
diphenylamidoborane-bis-$\eta^5$-n-butylcyclopentadienyl zirconium dichloride;
diphenylamidoborane-bis-$\eta^5$-n-butylcyclopentadienyl zirconium dimethyl;
diphenylamidoborane-bis-$\eta^5$-n-butylcyclopentadienyl zirconium dibenzyl;
diphenylamidoborane-bis-$\eta^5$-n-butylcyclopentadienyl zirconium bis(trimethylsilyl);
diphenylamidoborane-bis-$\eta^5$-n-butylcyclopentadienyl zirconium-2,3-dimethyl-2-butene-1,4-diyl;
diphenylamidoborane-bis-$\eta^5$-inden-1-yl zirconium dichloride;
diphenylamidoborane-bis-$\eta^5$-inden-1-yl zirconium dimethyl;
diphenylamidoborane-bis-$\eta^5$-inden-1-yl zirconium dibenzyl;
diphenylamidoborane-bis-$\eta^5$-inden-1-yl zirconium bis (trimethylsilyl);
diphenylamidoborane-bis-$\eta^5$-inden-1-yl zirconium-2,3-dimethyl-2-butene-1,4-diyl;
diphenylamidoborane-bis-$\eta^5$-2-methylinden-1-yl zirconium dichloride;
diphenylamidoborane-bis-$\eta^5$-2-methylinden-1-yl zirconium dimethyl;
diphenylamidoborane-bis-$\eta^5$-2-methylinden-1-yl zirconium dibenzyl;
diphenylamidoborane-bis-$\eta^5$-2-methylinden-1-yl zirconium bis(trimethylsilyl);
diphenylamidoborane-bis-$\eta^5$-2-methylinden-1-yl zirconium-2,3-dimethyl-2-butene-1,4-diyl;
diphenylamidoborane-bis-$\eta^5$-(2-methyl-4-phenylinden-1-yl)zirconium dichloride;
diphenylamidoborane-bis-$\eta^5$-(2-methyl-4-phenylinden-1-yl)zirconium dimethyl;
diphenylamidoborane-bis-$\eta^5$-(2-methyl-4-phenylinden-1-yl)zirconium dibenzyl;
diphenylamidoborane-bis-$\eta^5$-(2-methyl-4-phenylinden-1-yl)zirconium bis(trimethylsilyl);
diphenylamidoborane-bis-$\eta^5$-(2-methyl-4-phenylinden-1-yl)zirconium -2,3-dimethyl-2-butene-1,4-diyl;

diphenylamidoborane-bis-η⁵-(2-ethyl-4-phenylinden-1-yl) zirconium dichloride;
diphenylamidoborane-bis-η⁵-(2-ethyl-4-phenylinden-1-yl) zirconium dimethyl;
diphenylamidoborane-bis-η⁵-(2-ethyl-4-phenylinden-1-yl) zirconium dibenzyl;
diphenylamidoborane-bis-η⁵-(2-ethyl-4-phenylinden-1-yl) zirconium bis(trimethylsilyl);
diphenylamidoborane-bis-η⁵-(2-ethyl-4-phenylinden-1-yl) zirconium-2,3-dimethyl-2-butene-1,4-diyl;
diphenylamidoborane-bis-η⁵-(2-isopropyl-4-phenylinden-1-yl)zirconium dichloride;
diphenylamidoborane-bis-η⁵-(2-isopropyl-4-phenylinden-1-yl)zirconium dimethyl;
diphenylamidoborane-bis-η⁵-(2-isopropyl-4-phenylinden-1-yl)zirconium dibenzyl;
diphenylamidoborane-bis-η⁵-(2-isopropyl-4-phenylinden-1-yl)zirconium bis(trimethylsilyl);
diphenylamidoborane-bis-η⁵-(2-isopropyl-4-phenylinden-1-yl)zirconium-2,3-dimethyl-2-butene-1,4-diyl;
diphenylamidoborane-bis-η⁵-(2-methyl-4-naphthylinden-1-yl)zirconium dichloride;
diphenylamidoborane-bis-η⁵-(2-methyl-4-naphthylinden-1-yl)zirconium dimethyl;
diphenylamidoborane-bis-η⁵-(2-methyl-4-naphthylinden-1-yl)zirconium dibenzyl;
diphenylamidoborane-bis-η⁵-(2-methyl-4-naphthylinden-1-yl)zirconium bis(trimethylsilyl);
diphenylamidoborane-bis-η⁵-(2-methyl-4-naphthylinden-1-yl)zirconium-2,3-dimethyl-2-butene-1,4-diyl;
diphenylamidoborane-bis-η⁵-(2-methyl-4-bis(3,5-trifluoromethyl)phenylinden-1-yl)zirconium dichloride;
diphenylamidoborane-bis-η⁵-(2-methyl-4-bis(3,5-trifluoromethyl)phenylinden-1-yl)zirconium dimethyl;
diphenylamidoborane-bis-η⁵-(2-methyl-4-bis(3,5-trifluoromethyl)phenylinden-1-yl)zirconium dibenzyl;
diphenylamidoborane-bis-η⁵-(2-methyl-4-bis(3,5-trifluoromethyl)phenylinden-1-yl)zirconium bis(trimethylsilyl);
diphenylamidoborane-bis-η⁵-(2-methyl-4-bis(3,5-trifluoromethyl)phenylinden-1-yl)zirconium-2,3-dimethyl-2-butene-1,4-diyl;
diphenylamidoborane-bis-η⁵-(2-ethyl-4-bis(3,5-trifluoromethyl)phenylinden-1-yl)zirconium dichloride;
diphenylamidoborane-bis-η⁵-(2-ethyl-4-bis(3,5-trifluoromethyl)phenylinden-1-yl)zirconium dimethyl;
diphenylamidoborane-bis-η⁵-(2-ethyl-4-bis(3,5-trifluoromethyl)phenylinden-1-yl)zirconium dibenzyl;
diphenylamidoborane-bis-η⁵-(2-ethyl-4-bis(3,5-trifluoromethyl)phenylinden-1-yl)zirconium bis(trimethylsilyl);
diphenylamidoborane-bis-η⁵-(2-ethyl-4-bis(3,5-trifluoromethyl)phenylinden-1-yl)zirconium-2,3-dimethyl-2-butene-1,4-diyl;
diphenylamidoborane-bis-η⁵-(2-isopropyl-4-bis(3,5-trifluoromethyl)phenylinden-1-yl)zirconium dichloride;
diphenylamidoborane-bis-η⁵-(2-isopropyl-4-bis(3,5-trifluoromethyl)phenylinden-1-yl)zirconium dimethyl;
diphenylamidoborane-bis-η⁵-(2-isopropyl-4-bis(3,5-trifluoromethyl)phenylinden-1-yl)zirconium dibenzyl;
diphenylamidoborane-bis-η⁵-(2-isopropyl-4-bis(3,5-trifluoromethyl)phenylinden-1-yl)zirconium bis(trimethylsilyl);
diphenylamidoborane-bis-η⁵-(2-isopropyl-4-bis(3,5-trifluoromethyl)phenylinden-1-yl)zirconium-2,3-dimethyl-2-butene-1,4-diyl;
diphenylamidoborane-bis-η⁵-(3-isopropylinden-1-yl) zirconium dichloride;
diphenylamidoborane-bis-η⁵-(3-isopropylinden-1-yl) zirconium dimethyl;
diphenylamidoborane-bis-η⁵-(3-isopropylinden-1-yl) zirconium dibenzyl;
diphenylamidoborane-bis-η⁵-(3-isopropylinden-1-yl) zirconium bis(trimethylsilyl);
diphenylamidoborane-bis-η⁵-(3-isopropylinden-1-yl) zirconium-2,3-dimethyl-2-butene-1,4-diyl;
diphenylamidoborane-bis-η⁵-(3-t-butylinden-1-yl) zirconium dichloride;
diphenylamidoborane-bis-η⁵-(3-t-butylinden-1-yl) zirconium dimethyl;
diphenylamidoborane-bis-η⁵-(3-t-butylinden-1-yl) zirconium dibenzyl;
diphenylamidoborane-bis-η⁵-(3-t-butylinden-1-yl) zirconium bis(trimethylsilyl);
diphenylamidoborane-bis-η⁵-(3-t-butylinden-1-yl) zirconium-2,3-dimethyl-2-butene-1,4-diyl;
isoindolinidoborane-bis-η⁵-cyclopentadienyl zirconium dichloride;
isoindolinidoborane-bis-η⁵-cyclopentadienyl zirconium dimethyl;
isoindolinidoborane-bis-η⁵-cyclopentadienyl zirconium dibenzyl;
isoindolinidoborane-bis-η⁵-cyclopentadienyl zirconium bis (trimethylsilyl);
isoindolinidoborane-bis-η⁵-cyclopentadienyl zirconium-2,3-dimethyl-2-butene-1,4-diyl;
isoindolinidoborane-bis-η⁵-n-butylcyclopentadienyl zirconium dichloride;
isoindolinidoborane-bis-η⁵-n-butylcyclopentadienyl zirconium dimethyl;
isoindolinidoborane-bis-η⁵-n-butylcyclopentadienyl zirconium dibenzyl;
isoindolinidoborane-bis-η⁵-n-butylcyclopentadienyl zirconium bis(trimethylsilyl);
isoindolinidoborane-bis-η⁵-n-butylcyclopentadienyl zirconium-2,3-dimethyl-2-butene-1,4-diyl;
isoindolinidoborane-bis-η⁵-inden-1-yl zirconium dichloride;
isoindolinidoborane-bis-η⁵-inden-1-yl zirconium dimethyl;
isoindolinidoborane-bis-η⁵-inden-1-yl zirconium dibenzyl;
isoindolinidoborane-bis-η⁵-inden-1-yl zirconium bis (trimethylsilyl);
isoindolinidoborane-bis-η⁵-inden-1-yl zirconium-2,3-dimethyl-2-butene-1,4-diyl;
isoindolinidoborane-bis-η⁵-2-methylinden-1-yl zirconium dichloride;
isoindolinidoborane-bis-η⁵-2-methylinden-1-yl zirconium dimethyl;
isoindolinidoborane-bis-η⁵-2-methylinden-1-yl zirconium dibenzyl;
isoindolinidoborane-bis-η⁵-2-methylinden-1-yl zirconium dibenzyl;
isoindolinidoborane-bis-η⁵-2-methylinden-1-yl zirconium bis(trimethylsilyl);
isoindolinidoborane-bis-η⁵-(2-methylinden-1-yl zirconium-2,3-dimethyl-2-butene-1,4-diyl;
isoindolinidoborane-bis-η⁵-(2-methyl-4-phenylinden-1-yl) zirconium dichloride;
isoindolinidoborane-bis-η⁵-(2-methyl-4-phenylinden-1-yl) zirconium dimethyl;
isoindolinidoborane-bis-η⁵-(2-methyl-4-phenylinden-1-yl) zirconium dibenzyl;
isoindolinidoborane-bis-η⁵-(2-methyl-4-phenylinden-1-yl) zirconium bis(trimethylsilyl);
isoindolinidoborane-bis-η⁵-(2-methyl-4-phenylinden-1-yl) zirconium -2,3-dimethyl-2-butene-1,4-diyl;

isoindolinidoborane-bis-$\eta^5$-(2-ethyl-4-phenylinden-1-yl) zirconium dichloride;
isoindolinidoborane-bis-$\eta^5$-(2-ethyl-4-phenylinden-1-yl) zirconium dimethyl;
isoindolinidoborane-bis-$\eta^5$-(2-ethyl-4-phenylinden-1-yl) zirconium dibenzyl;
isoindolinidoborane-bis-$\eta^5$-(2-ethyl-4-phenylinden-1-yl) zirconium bis(trimethylsilyl);
isoindolinidoborane-bis-$\eta^5$-(2-ethyl-4-phenylinden-1-yl) zirconium-2,3-dimethyl-2-butene-1,4-diyl;
isoindolinidoborane-bis-$\eta^5$-(2-isopropyl-4-phenylinden-1-yl)zirconium dichloride;
isoindolinidoborane-bis-$\eta^5$-(2-isopropyl-4-phenylinden-1-yl)zirconium dimethyl;
isoindolinidoborane-bis-$\eta^5$-(2-isopropyl-4-phenylinden-1-yl)zirconium dibenzyl;
isoindolinidoborane-bis-$\eta^5$-(2-isopropyl-4-phenylinden-1-yl)zirconium bis(trimethylsilyl);
isoindolinidoborane-bis-$\eta^5$-(2-isopropyl-4-phenylinden-1-yl)zirconium-2,3-dimethyl-2-butene-1,4-diyl;
isoindolinidoborane-bis-$\eta^5$-(2-methyl-4-naphthylinden-1-yl)zirconium dichloride;
isoindolinidoborane-bis-$\eta^5$-(2-methyl-4-naphthylinden-1-yl)zirconium dimethyl;
isoindolinidoborane-bis-$\eta^5$-(2-methyl-4-naphthylinden-1-yl)zirconium dibenzyl;
isoindolinidoborane-bis-$\eta^5$-(2-methyl-4-naphthylinden-1-yl)zirconium bis(trimethylsilyl);
isoindolinidoborane-bis-$\eta^5$-(2-methyl-4-naphthylinden-1-yl)zirconium-2,3-dimethyl-2-butene-1,4-diyl;
isoindolinidoborane-bis-$\eta^5$-(2-methyl-4-bis(3,5-trifluoromethyl)phenylinden-1-yl)zirconium dichloride;
isoindolinidoborane-bis-$\eta^5$-(2-methyl-4-bis(3,5-trifluoromethyl)phenylinden-1-yl)zirconium dimethyl;
isoindolinidoborane-bis-$\eta^5$-(2-methyl-4-bis(3,5-trifluoromethyl)phenylinden-1-yl)zirconium dibenzyl;
isoindolinidoborane-bis-$\eta^5$-(2-methyl-4-bis(3,5-trifluoromethyl)phenylinden-1-yl)zirconium bis(trimethylsilyl);
isoindolinidoborane-bis-$\eta^5$-(2-methyl-4-bis(3,5-trifluoromethyl)phenylinden-1-yl)zirconium-2,3-dimethyl-2-butene-1,4-diyl;
isoindolinidoborane-bis-$\eta^5$-(2-ethyl-4-bis(3,5-trifluoromethyl)phenylinden-1-yl)zirconium dichloride;
isoindolinidoborane-bis-$\eta^5$-(2-ethyl-4-bis(3,5-trifluoromethyl)phenylinden-1-yl)zirconium dimethyl;
isoindolinidoborane-bis-$\eta^5$-(2-ethyl-4-bis(3,5-trifluoromethyl)phenylinden-1-yl)zirconium dibenzyl;
isoindolinidoborane-bis-$\eta^5$-(2-ethyl-4-bis(3,5-trifluoromethyl)phenylinden-1-yl)zirconium bis(trimethylsilyl);
isoindolinidoborane-bis-$\eta^5$-(2-ethyl-4-bis(3,5-trifluoromethyl)phenylinden-1-yl)zirconium-2,3-dimethyl-2-butene-1,4-diyl;
isoindolinidoborane-bis-$\eta^5$-(2-isopropyl-4-bis(3,5-trifluoromethyl)phenylinden-1-yl)zirconium dichloride;
isoindolinidoborane-bis-$\eta^5$-(2-isopropyl-4-bis(3,5-trifluoromethyl)phenylinden-1-yl)zirconium dimethyl;
isoindolinidoborane-bis-$\eta^5$-(2-isopropyl-4-bis(3,5-trifluoromethyl)phenylinden-1-yl)zirconium dibenzyl;
isoindolinidoborane-bis-$\eta^5$-(2-isopropyl-4-bis(3,5-trifluoromethyl)phenylinden-1-yl)zirconium bis(trimethylsilyl);
isoindolinidoborane-bis-$\eta^5$-(2-isopropyl-4-bis(3,5-trifluoromethyl)phenylinden-1-yl)zirconium-2,3-dimethyl-2-butene-1,4-diyl;
isoindolinidoborane-bis-$\eta^5$-(3-isopropylinden-1-yl) zirconium dichloride;
isoindolinidoborane-bis-$\eta^5$-(3-isopropylinden-1-yl) zirconium dimethyl;
isoindolinidoborane-bis-$\eta^5$-(3-isopropylinden-1-yl) zirconium dibenzyl;
isoindolinidoborane-bis-$\eta^5$-(3-isopropylinden-1-yl) zirconium bis(trimethylsilyl);
isoindolinidoborane-bis-$\eta^5$-(3-isopropylinden-1-yl) zirconium-2,3-dimethyl-2-butene-1,4-diyl;
isoindolinidoborane-bis-$\eta^5$-(3-t-butylinden-1-yl)zirconium dichloride;
isoindolinidoborane-bis-$\eta^5$-(3-t-butylinden-1-yl)zirconium dimethyl;
isoindolinidoborane-bis-$\eta^5$-(3-t-butylinden-1-yl)zirconium dibenzyl;
isoindolinidoborane-bis-$\eta^5$-(3-t-butylinden-1-yl)zirconium bis(trimethylsilyl);
isoindolinidoborane-bis-$\eta^5$-(3-t-butylinden-1-yl)zirconium-2,3-dimethyl-2-butene-1,4-diyl;
bis(4-dimethylaminophenyl)borane-bis-$\eta^5$-cyclopentadienyl zirconium dichloride;
bis(4-dimethylaminophenyl)borane-bis-$\eta^5$-cyclopentadienyl zirconium dimethyl;
bis(4-dimethylaminophenyl)borane-bis-$\eta^5$-cyclopentadienyl zirconium dibenzyl;
bis(4-dimethylaminophenyl)borane-bis-$\eta^5$-cyclopentadienyl zirconium bis(trimethylsilyl);
bis(4-dimethylaminophenyl)borane-bis-$\eta^5$-cyclopentadienyl zirconium-2,3-dimethyl-2-butene-1,4-diyl;
bis(4-dimethylaminophenyl)borane-bis-$\eta^5$-n-butylcyclopentadienyl zirconium dichloride;
bis(4-dimethylaminophenyl)borane-bis-$\eta^5$-n-butylcyclopentadienyl zirconium dimethyl;
bis(4-dimethylaminophenyl)borane-bis-$\eta^5$-n-butylcyclopentadienyl zirconium dibenzyl;
bis(4-dimethylaminophenyl)borane-bis-$\eta^5$-n-butylcyclopentadienyl zirconium bis(trimethylsilyl);
bis(4-dimethylaminophenyl)borane-bis-$\eta^5$-n-butylcyclopentadienyl zirconium-2,3-dimethyl-2-butene-1,4-diyl;
bis(4-dimethylaminophenyl)borane-bis-$\eta^5$-inden-1-yl zirconium dichloride;
bis(4-dimethylaminophenyl)borane-bis-$\eta^5$-inden-1-yl zirconium dimethyl;
bis(4-dimethylaminophenyl)borane-bis-$\eta^5$-inden-1-yl zirconium dibenzyl;
bis(4-dimethylaminophenyl)borane-bis-$\eta^5$-inden-1-yl zirconium bis(trimethylsilyl);
bis(4-dimethylaminophenyl)borane-bis-$\eta^5$-inden-1-yl zirconium-2,3-dimethyl-2-butene-1,4-diyl;
bis(4-dimethylaminophenyl)borane-bis-$\eta^5$-2-methylinden-1-yl zirconium dichloride;
bis(4-dimethylaminophenyl)borane-bis-$\eta^5$-2-methylinden-1-yl zirconium dimethyl;
bis(4-dimethylaminophenyl)borane-bis-$\eta^5$-2-methylinden-1-yl zirconium dibenzyl;
bis(4-dimethylaminophenyl)borane-bis-$\eta^5$-2-methylinden-1-yl zirconium bis(trimethylsilyl);
bis(4-dimethylaminophenyl)borane-bis-$\eta^5$-2-methylinden-1-yl zirconium-2,3-dimethyl-2-butene-1,4-diyl;
bis(4-dimethylaminophenyl)borane-bis-$\eta^5$-(2-methyl-4-phenylinden-1-yl)zirconium dichloride;
bis(4-dimethylaminophenyl)borane-bis-$\eta^5$-(2-methyl-4-phenylinden-1-yl)zirconium dimethyl;
bis(4-dimethylaminophenyl)borane-bis-$\eta^5$-(2-methyl-4-phenylinden-1-yl)zirconium dibenzyl;
bis(4-dimethylaminophenyl)borane-bis-$\eta^5$-(2-methyl-4-phenylinden-1-yl)zirconium bis(trimethylsilyl);

bis(4-dimethylaminophenyl)borane-bis-η⁵-(2-methyl-4-phenylinden-1-yl)zirconium -2,3-dimethyl-2-butene-1,4-diyl;

bis(4-dimethylaminophenyl)borane-bis-η⁵-(2-ethyl-4-phenylinden-1-yl)zirconium dichloride;

bis(4-dimethylaminophenyl)borane-bis-η⁵-(2-ethyl-4-phenylinden-1-yl)zirconium dimethyl;

bis(4-dimethylaminophenyl)borane-bis-η⁵-(2-ethyl-4-phenylinden-1-yl)zirconium dibenzyl;

bis(4-dimethylaminophenyl)borane-bis-η⁵-(2-ethyl-4-phenylinden-1-yl)zirconium bis(trimethylsilyl);

bis(4-dimethylaminophenyl)borane-bis-η⁵-(2-ethyl-4-phenylinden-1-yl)zirconium-2,3-dimethyl-2-butene-1,4-diyl;

bis(4-dimethylaminophenyl)borane-bis-η⁵-(2-isopropyl-4-phenylinden-1-yl)zirconium dichloride;

bis(4-dimethylaminophenyl)borane-bis-η⁵-(2-isopropyl-4-phenylinden-1-yl)zirconium dimethyl;

bis(4-dimethylaminophenyl)borane-bis-η⁵-(2-isopropyl-4-phenylinden-1-yl)zirconium dibenzyl;

bis(4-dimethylaminophenyl)borane-bis-η⁵-(2-isopropyl-4-phenylinden-1-yl)zirconium bis(trimethylsilyl);

bis(4-dimethylaminophenyl)borane-bis-η⁵-(2-isopropyl-4-phenylinden-1-yl)zirconium-2,3-dimethyl-2-butene-1,4-diyl;

bis(4-dimethylaminophenyl)borane-bis-η⁵-(2-methyl-4-naphthylinden-1-yl)zirconium dichloride;

bis(4-dimethylaminophenyl)borane-bis-η⁵-(2-methyl-4-naphthylinden-1-yl)zirconium dimethyl;

bis(4-dimethylaminophenyl)borane-bis-η⁵-(2-methyl-4-naphthylinden-1-yl)zirconium dibenzyl;

bis(4-dimethylaminophenyl)borane-bis-η⁵-(2-methyl-4-naphthylinden-1-yl)zirconium bis(trimethylsilyl);

bis(4-dimethylaminophenyl)borane-bis-η⁵-(2-methyl-4-naphthylinden-1-yl)zirconium-2,3-dimethyl-2-butene-1,4-diyl;

bis(4-dimethylaminophenyl)borane-bis-η⁵-(2-methyl-4-bis(3,5-trifluoromethyl)phenylinden-1-yl)zirconium dichloride;

bis(4-dimethylaminophenyl)borane-bis-η⁵-(2-methyl-4-bis(3,5-trifluoromethyl)phenylinden-1-yl)zirconium dimethyl;

bis(4-dimethylaminophenyl)borane-bis-η⁵-(2-methyl-4-bis(3,5-trifluoromethyl)phenylinden-1-yl)zirconium dibenzyl;

bis(4-dimethylaminophenyl)borane-bis-η⁵-(2-methyl-4-bis(3,5-trifluoromethyl)phenylinden-1-yl)zirconium bis(trimethylsilyl);

bis(4-dimethylaminophenyl)borane-bis-η⁵-(2-methyl-4-bis(3,5-trifluoromethyl)phenylinden-1-yl)zirconium-2,3-dimethyl-2-butene-1,4-diyl;

bis(4-dimethylaminophenyl)borane-bis-η⁵-(2-ethyl-4-bis(3,5-trifluoromethyl)phenylinden-1-yl)zirconium dichloride;

bis(4-dimethylaminophenyl)borane-bis-η⁵-(2-ethyl-4-bis(3,5-trifluoromethyl)phenylinden-1-yl)zirconium dimethyl;

bis(4-dimethylaminophenyl)borane-bis-η⁵-(2-ethyl-4-bis(3,5-trifluoromethyl)phenylinden-1-yl)zirconium dibenzyl;

bis(4-dimethylaminophenyl)borane-bis-η⁵-(2-ethyl-4-bis(3,5-trifluoromethyl)phenylinden-1-yl)zirconium bis(trimethylsilyl);

bis(4-dimethylaminophenyl)borane-bis-η⁵-(2-ethyl-4-bis(3,5-trifluoromethyl)phenylinden-1-yl)zirconium-2,3-dimethyl-2-butene-1,4-diyl;

bis(4-dimethylaminophenyl)borane-bis-η⁵-(2-isopropyl-4-bis(3,5-trifluoromethyl)phenylinden-1-yl)zirconium dichloride;

bis(4-dimethylaminophenyl)borane-bis-η⁵-(2-isopropyl-4-bis(3,5-trifluoromethyl)phenylinden-1-yl)zirconium dimethyl;

bis(4-dimethylaminophenyl)borane-bis-η⁵-(2-isopropyl-4-bis(3,5-trifluoromethyl)phenylinden-1-yl)zirconium dibenzyl;

bis(4-dimethylaminophenyl)borane-bis-η⁵-(2-isopropyl-4-bis(3,5-trifluoromethyl)phenylinden-1-yl)zirconium bis(trimethylsilyl);

bis(4-dimethylaminophenyl)borane-bis-η⁵-(2-isopropyl-4-bis(3,5-trifluoromethyl)phenylinden-1-yl)zirconium-2,3-dimethyl-2-butene-1,4-diyl;

bis(4-dimethylaminophenyl)borane-bis-η⁵-(3-isopropylinden-1-yl)zirconium dichloride;

bis(4-dimethylaminophenyl)borane-bis-η⁵-(3-isopropylinden-1-yl)zirconium dimethyl;

bis(4-dimethylaminophenyl)borane-bis-η⁵-(3-isopropylinden-1-yl)zirconium dibenzyl;

bis(4-dimethylaminophenyl)borane-bis-η⁵-(3-isopropylinden-1-yl)zirconium bis(trimethylsilyl);

bis(4-dimethylaminophenyl)borane-bis-η⁵-(3-isopropylinden-1-yl)zirconium-2,3-dimethyl-2-butene-1,4-diyl;

bis(4-dimethylaminophenyl)borane-bis-η⁵-(3-t-butylinden-1-yl)zirconium dichloride;

bis(4-dimethylaminophenyl)borane-bis-η⁵-(3-t-butylinden-1-yl)zirconium dimethyl;

bis(4-dimethylaminophenyl)borane-bis-η⁵-(3-t-butylinden-1-yl)zirconium dibenzyl;

bis(4-dimethylaminophenyl)borane-bis-η⁵-(3-t-butylinden-1-yl)zirconium bis(trimethylsilyl);

bis(4-dimethylaminophenyl)borane-bis-η⁵-(3-t-butylinden-1-yl)zirconium-2,3-dimethyl-2-butene-1,4-diyl;

N-methylpiperazinoborane-bis-η⁵-cyclopentadienyl zirconium dichloride;

N-methylpiperazinoborane-bis-η⁵-cyclopentadienyl zirconium dimethyl;

N-methylpiperazinoborane-bis-η⁵-cyclopentadienyl zirconium dibenzyl;

N-methylpiperazinoborane-bis-η⁵-cyclopentadienyl zirconium bis(trimethylsilyl);

N-methylpiperazinoborane-bis-η⁵-cyclopentadienyl zirconium-2,3-dimethyl-2-butene-1,4-diyl;

N-methylpiperazinoborane-bis-η⁵-n-butylcyclopentadienyl zirconium dichloride;

N-methylpiperazinoborane-bis-η⁵-n-butylcyclopentadienyl zirconium dimethyl;

N-methylpiperazinoborane-bis-η⁵-n-butylcyclopentadienyl zirconium dibenzyl;

N-methylpiperazinoborane-bis-η⁵-n-butylcyclopentadienyl zirconium bis(trimethylsilyl);

N-methylpiperazinoborane-bis-η⁵-n-butylcyclopentadienyl zirconium-2,3-dimethyl-2-butene-1,4-diyl;

N-methylpiperazinoborane-bis-η⁵-inden-1-yl zirconium dichloride;

N-methylpiperazinoborane-bis-η⁵-inden-1-yl zirconium dimethyl;

N-methylpiperazinoborane-bis-η⁵-inden-1-yl zirconium dibenzyl;

N-methylpiperazinoborane-bis-η⁵-inden-1-yl zirconium bis(trimethylsilyl);

N-methylpiperazinoborane-bis-η⁵-inden-1-yl zirconium-2,3-dimethyl-2-butene-1,4-diyl;

N-methylpiperazinoborane-bis-η⁵-2-methylinden-1-yl zirconium dichloride;

N-methylpiperazinoborane-bis-η⁵-2-methylinden-1-yl zirconium dimethyl;

N-methylpiperazinoborane-bis-$\eta^5$-2-methylinden-1-yl zirconium dibenzyl;
N-methylpiperazinoborane-bis-$\eta^5$-2-methylinden-1-yl zirconium bis(trimethylsilyl);
N-methylpiperazinoborane-bis-$\eta^5$-2-methylinden-1-yl zirconium-2,3-dimethyl-2-butene-1,4-diyl;
N-methylpiperazinoborane-bis-$\eta^5$-(2-methyl-4-phenylinden-1-yl)zirconium dichloride;
N-methylpiperazinoborane-bis-$\eta^5$-(2-methyl-4-phenylinden-1-yl)zirconium dimethyl;
N-methylpiperazinoborane-bis-$\eta^5$-(2-methyl-4-phenylinden-1-yl)zirconium dibenzyl;
N-methylpiperazinoborane-bis-$\eta^5$-(2-methyl-4-phenylinden-1-yl)zirconium bis(trimethylsilyl);
N-methylpiperazinoborane-bis-$\eta^5$-(2-methyl-4-phenylinden-1-yl)zirconium -2,3-dimethyl-2-butene-1,4-diyl;
N-methylpiperazinoborane-bis-$\eta^5$-(2-ethyl-4-phenylinden-1-yl)zirconium dichloride;
N-methylpiperazinoborane-bis-$\eta^5$-(2-ethyl-4-phenylinden-1-yl)zirconium dimethyl;
N-methylpiperazinoborane-bis-$\eta^5$-(2-ethyl-4-phenylinden-1-yl)zirconium dibenzyl;
N-methylpiperazinoborane-bis-$\eta^5$-(2-ethyl-4-phenylinden-1-yl)zirconium bis(trimethylsilyl);
N-methylpiperazinoborane-bis-$\eta^5$-(2-ethyl-4-phenylinden-1-yl)zirconium-2,3-dimethyl-2-butene-1,4-diyl;
N-methylpiperazinoborane-bis-$\eta^5$-(2-isopropyl-4-phenylinden-1-yl)zirconium dichloride;
N-methylpiperazinoborane-bis-$\eta^5$-(2-isopropyl-4-phenylinden-1-yl)zirconium dimethyl;
N-methylpiperazinoborane-bis-$\eta^5$-(2-isopropyl-4-phenylinden-1-yl)zirconium dibenzyl;
N-methylpiperazinoborane-bis-$\eta^5$-(2-isopropyl-4-phenylinden-1-yl)zirconium bis(trimethylsilyl);
N-methylpiperazinoborane-bis-$\eta^5$-(2-isopropyl-4-phenylinden-1-yl)zirconium-2,3-dimethyl-2-butene-1,4-diyl;
N-methylpiperazinoborane-bis-$\eta^5$-(2-methyl-4-naphthylinden-1-yl)zirconium dichloride;
N-methylpiperazinoborane-bis-$\eta^5$-(2-methyl-4-naphthylinden-1-yl)zirconium dimethyl;
N-methylpiperazinoborane-bis-$\eta^5$-(2-methyl-4-naphthylinden-1-yl)zirconium dibenzyl;
N-methylpiperazinoborane-bis-$\eta^5$-(2-methyl-4-naphthylinden-1-yl)zirconium bis(trimethylsilyl);
N-methylpiperazinoborane-bis-$\eta^5$-(2-methyl-4-naphthylinden-1-yl)zirconium-2,3-dimethyl-2-butene-1,4-diyl;
N-methylpiperazinoborane-bis-$\eta^5$-(2-methyl-4-bis(3,5-trifluoromethyl)phenylinden-1-yl)zirconium dichloride;
N-methylpiperazinoborane-bis-$\eta^5$-(2-methyl-4-bis(3,5-trifluoromethyl)phenylinden-1-yl)zirconium dimethyl;
N-methylpiperazinoborane-bis-$\eta^5$-(2-methyl-4-bis(3,5-trifluoromethyl)phenylinden-1-yl)zirconium dibenzyl;
N-methylpiperazinoborane-bis-$\eta^5$-(2-methyl-4-bis(3,5-trifluoromethyl)phenylinden-1-yl)zirconium bis(trimethylsilyl);
N-methylpiperazinoborane-bis-$\eta^5$-(2-methyl-4-bis(3,5-trifluoromethyl)phenylinden-1-yl)zirconium-2,3-dimethyl-2-butene-1,4-diyl;
N-methylpiperazinoborane-bis-$\eta^5$-(2-ethyl-4-bis(3,5-trifluoromethyl)phenylinden-1-yl)zirconium dichloride;
N-methylpiperazinoborane-bis-$\eta^5$-(2-ethyl-4-bis(3,5-trifluoromethyl)phenylinden-1-yl)zirconium dimethyl;
N-methylpiperazinoborane-bis-$\eta^5$-(2-ethyl-4-bis(3,5-trifluoromethyl)phenylinden-1-yl)zirconium dibenzyl;
N-methylpiperazinoborane-bis-$\eta^5$-(2-ethyl-4-bis(3,5-trifluoromethyl)phenylinden-1-yl)zirconium bis(trimethylsilyl);
N-methylpiperazinoborane-bis-$\eta^5$-(2-ethyl-4-bis(3,5-trifluoromethyl)phenylinden-1-yl)zirconium-2,3-dimethyl-2-butene-1,4-diyl;
N-methylpiperazinoborane-bis-$\eta^5$-(2-isopropyl-4-bis(3,5-trifluoromethyl)phenylinden-1-yl)zirconium dichloride;
N-methylpiperazinoborane-bis-$\eta^5$-(2-isopropyl-4-bis(3,5-trifluoromethyl)phenylinden-1-yl)zirconium dimethyl;
N-methylpiperazinoborane-bis-$\eta^5$-(2-isopropyl-4-bis(3,5-trifluoromethyl)phenylinden-1-yl)zirconium dibenzyl;
N-methylpiperazinoborane-bis-$\eta^5$-(2-isopropyl-4-bis(3,5-trifluoromethyl)phenylinden-1-yl)zirconium bis(trimethylsilyl);
N-methylpiperazinoborane-bis-$\eta^5$-(2-isopropyl-4-bis(3,5-trifluoromethyl)phenylinden-1-yl)zirconium-2,3-dimethyl-2-butene-1,4-diyl;
N-methylpiperazinoborane-bis-$\eta^5$-(3-isopropylinden-1-yl)zirconium dichloride;
N-methylpiperazinoborane-bis-$\eta^5$-(3-isopropylinden-1-yl)zirconium dimethyl;
N-methylpiperazinoborane-bis-$\eta^5$-(3-isopropylinden-1-yl)zirconium dibenzyl;
N-methylpiperazinoborane-bis-$\eta^5$-(3-isopropylinden-1-yl)zirconium bis(trimethylsilyl);
N-methylpiperazinoborane-bis-$\eta^5$-(3-isopropylinden-1-yl)zirconium-2,3-dimethyl-2-butene-1,4-diyl;
N-methylpiperazinoborane-bis-$\eta^5$-(3-t-butylinden-1-yl)zirconium dichloride;
N-methylpiperazinoborane-bis-$\eta^5$-(3-t-butylinden-1-yl)zirconium dimethyl;
N-methylpiperazinoborane-bis-$\eta^5$-(3-t-butylinden-1-yl)zirconium dibenzyl;
N-methylpiperazinoborane-bis-$\eta^5$-(3-t-butylinden-1-yl)zirconium bis(trimethylsilyl);
N-methylpiperazinoborane-bis-$\eta^5$-(3-t-butylinden-1-yl)zirconium-2,3-dimethyl-2-butene-1,4-diyl;
morpholinoborane-bis-$\eta^5$-cyclopentadienyl zirconium dichloride;
morpholinoborane-bis-$\eta^5$-cyclopentadienyl zirconium dimethyl;
morpholinoborane-bis-$\eta^5$-cyclopentadienyl zirconium dibenzyl;
morpholinoborane-bis-$\eta^5$-cyclopentadienyl zirconium bis(trimethylsilyl);
morpholinoborane-bis-$\eta^5$-cyclopentadienyl zirconium-2,3-dimethyl-2-butene-1,4-diyl;
morpholinoborane-bis-$\eta^5$-n-butylcyclopentadienyl zirconium dichloride;
morpholinoborane-bis-$\eta^5$-n-butylcyclopentadienyl zirconium dimethyl;
morpholinoborane-bis-$\eta^5$-n-butylcyclopentadienyl zirconium dibenzyl;
morpholinoborane-bis-$\eta^5$-n-butylcyclopentadienyl zirconium bis(trimethylsilyl);
morpholinoborane-bis-$\eta^5$-n-butylcyclopentadienyl zirconium-2,3-dimethyl-2-butene-1,4-diyl;
morpholinoborane-bis-$\eta^5$-inden-1-yl zirconium dichloride;
morpholinoborane-bis-$\eta^5$-inden-1-yl zirconium dimethyl;
morpholinoborane-bis-$\eta^5$-inden-1-yl zirconium dibenzyl;
morpholinoborane-bis-$\eta^5$-inden-1-yl zirconium bis(trimethylsilyl);
morpholinoborane-bis-$\eta^5$-inden-1-yl zirconium-2,3-dimethyl-2-butene-1,4-diyl;
morpholinoborane-bis-$\eta^5$-2-methylinden-1-yl zirconium dichloride;

morpholinoborane-bis-$\eta^5$-2-methylinden-1-yl zirconium dimethyl;
morpholinoborane-bis-$\eta^5$-2-methylinden-1-yl zirconium dibenzyl;
morpholinoborane-bis-$\eta^5$-2-methylinden-1-yl zirconium bis(trimethylsilyl);
morpholinoborane-bis-$\eta^5$-2-methylinden-1-yl zirconium-2,3-dimethyl-2-butene-1,4-diyl;
morpholinoborane-bis-$\eta^5$-(2-methyl-4-phenylinden-1-yl) zirconium dichloride;
morpholinoborane-bis-$\eta^5$-(2-methyl-4-phenylinden-1-yl) zirconium dimethyl;
morpholinoborane-bis-$\eta^5$-(2-methyl-4-phenylinden-1-yl) zirconium dibenzyl;
morpholinoborane-bis-$\eta^5$-(2-methyl-4-phenylinden-1-yl) zirconium bis(trimethylsilyl);
morpholinoborane-bis-$\eta^5$-(2-methyl-4-phenylinden-1-yl) zirconium -2,3-dimethyl-2-butene-1,4-diyl;
morpholinoborane-bis-$\eta^5$-(2-ethyl-4-phenylinden-1-yl) zirconium dichloride;
morpholinoborane-bis-$\eta^5$-(2-ethyl-4-phenylinden-1-yl) zirconium dimethyl;
morpholinoborane-bis-$\eta^5$-(2-ethyl-4-phenylinden-1-yl) zirconium dibenzyl;
morpholinoborane-bis-$\eta^5$-(2-ethyl-4-phenylinden-1-yl) zirconium bis(trimethylsilyl);
morpholinoborane-bis-$\eta^5$-(2-ethyl-4-phenylinden-1-yl) zirconium-2,3-dimethyl-2-butene-1,4-diyl;
morpholinoborane-bis-$\eta^5$-(2-isopropyl-4-phenylinden-1-yl) zirconium dichloride;
morpholinoborane-bis-$\eta^5$-(2-isopropyl-4-phenylinden-1-yl) zirconium dimethyl;
morpholinoborane-bis-$\eta^5$-(2-isopropyl-4-phenylinden-1-yl) zirconium dibenzyl;
morpholinoborane-bis-$\eta^5$-(2-isopropyl-4-phenylinden-1-yl) zirconium bis(trimethylsilyl);
morpholinoborane-bis-$\eta^5$-(2-isopropyl-4-phenylinden-1-yl) zirconium-2,3-dimethyl-2-butene-1,4-diyl;
morpholinoborane-bis-$\eta^5$-(2-methyl-4-naphthylinden-1-yl) zirconium dichloride;
morpholinoborane-bis-$\eta^5$-(2-methyl-4-naphthylinden-1-yl) zirconium dimethyl;
morpholinoborane-bis-$\eta^5$-(2-methyl-4-naphthylinden-1-yl) zirconium dibenzyl;
morpholinoborane-bis-$\eta^5$-(2-methyl-4-naphthylinden-1-yl) zirconium bis(trimethylsilyl);
morpholinoborane-bis-$\eta^5$-(2-methyl-4-naphthylinden-1-yl) zirconium-2,3-dimethyl-2-butene-1,4-diyl;
morpholinoborane-bis-$\eta^5$-(2-methyl-4-bis(3,5-trifluoromethyl)phenylinden-1-yl)zirconium dichloride;
morpholinoborane-bis-$\eta^5$-(2-methyl-4-bis(3,5-trifluoromethyl)phenylinden-1-yl)zirconium dimethyl;
morpholinoborane-bis-$\eta^5$-(2-methyl-4-bis(3,5-trifluoromethyl)phenylinden-1-yl)zirconium dibenzyl;
morpholinoborane-bis-$\eta^5$-(2-methyl-4-bis(3,5-trifluoromethyl)phenylinden-1-yl)zirconium bis(trimethylsilyl);
morpholinoborane-bis-$\eta^5$-(2-methyl-4-bis(3,5-trifluoromethyl)phenylinden-1-yl)zirconium-2,3-dimethyl-2-butene-1,4-diyl;
morpholinoborane-bis-$\eta^5$-(2-ethyl-4-bis(3,5-trifluoromethyl)phenylinden-1-yl)zirconium dichloride;
morpholinoborane-bis-$\eta^5$-(2-ethyl-4-bis(3,5-trifluoromethyl)phenylinden-1-yl)zirconium dimethyl;
morpholinoborane-bis-$\eta^5$-(2-ethyl-4-bis(3,5-trifluoromethyl)phenylinden-1-yl)zirconium dibenzyl;
morpholinoborane-bis-$\eta^5$-(2-ethyl-4-bis(3,5-trifluoromethyl)phenylinden-1-yl)zirconium bis(trimethylsilyl);
morpholinoborane-bis-$\eta^5$-(2-ethyl-4-bis(3,5-trifluoromethyl)phenylinden-1-yl)zirconium-2,3-dimethyl-2-butene-1,4-diyl;
morpholinoborane-bis-$\eta^5$-(2-isopropyl-4-bis(3,5-trifluoromethyl)phenylinden-1-yl)zirconium dichloride;
morpholinoborane-bis-$\eta^5$-(2-isopropyl-4-bis(3,5-trifluoromethyl)phenylinden-1-yl)zirconium dimethyl;
morpholinoborane-bis-$\eta^5$-(2-isopropyl-4-bis(3,5-trifluoromethyl)phenylinden-1-yl)zirconium dibenzyl;
morpholinoborane-bis-$\eta^5$-(2-isopropyl-4-bis(3,5-trifluoromethyl)phenylinden-1-yl)zirconium bis(trimethylsilyl);
morpholinoborane-bis-$\eta^5$-(2-isopropyl-4-bis(3,5-trifluoromethyl)phenylinden-1-yl)zirconium-2,3-dimethyl-2-butene-1,4-diyl;
morpholinoborane-bis-$\eta^5$-(3-isopropylinden-1-yl) zirconium dichloride;
morpholinoborane-bis-$\eta^5$-(3-isopropylinden-1-yl) zirconium dimethyl;
morpholinoborane-bis-$\eta^5$-(3-isopropylinden-1-yl) zirconium dibenzyl;
morpholinoborane-bis-$\eta^5$-(3-isopropylinden-1-yl) zirconium bis(trimethylsilyl);
morpholinoborane-bis-$\eta^5$-(3-isopropylinden-1-yl) zirconium-2,3-dimethyl-2-butene-1,4-diyl;
morpholinoborane-bis-$\eta^5$-(3-t-butylinden-1-yl)zirconium dichloride;
morpholinoborane-bis-$\eta^5$-(3-t-butylinden-1-yl)zirconium dimethyl;
morpholinoborane-bis-$\eta^5$-(3-t-butylinden-1-yl)zirconium dibenzyl;
morpholinoborane-bis-$\eta^5$-(3-t-butylinden-1-yl)zirconium bis(trimethylsilyl); and
morpholinoborane-bis-$\eta^5$-(3-t-butylinden-1-yl)zirconium-2,3-dimethyl-2-butene-1,4-diyl.

The skilled artisan will recognize that additional members of the foregoing list, such as those wherein zirconium is replaced by hafnium are also included within the invention. Moreover, it should also be recognized that the terms $\eta^5$ or $\eta^4$ may not accurately reflect the actual electronic distribution of the molecule under use conditions, and that molecules including lesser numbers of contributing atoms to the electronic delocation are intended to be included within such descriptions as well.

In general, the process of synthesizing the foregoing compounds and complexes is performed under inert atmosphere using standard organometallic synthetic procedures. The recovery of the desired Group 4 transition metal complex is accomplished by separation of the product from any by-products and devolatilization of the reaction medium. Extraction into a secondary solvent may be employed if desired. Alternatively, if the desired product is an insoluble precipitate, filtration or other separation techniques may be employed. Final purification, if required, may be accomplished by recrystallization from an inert solvent, employing low temperatures if needed.

The complexes are rendered catalytically active by combination with an activating cocatalyst or use of an activating technique, such as those that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. A preferred ion forming compound is a tri($C_{1-20}$-hydrocarbyl)ammonium salt of a tetrakis (fluoroaryl)borate, especially a tetrakis(pentafluorophenyl) borate. The foregoing activating cocatalysts and activating techniques have been previously taught with respect to different metal complexes in the following references: EP-A-277,003, U.S. Pat. No. 5,153,157, U.S. Pat. No. 5,064,802, U.S. Pat. No. 5,321,106, U.S. Pat. No. 5,721,185, U.S. Pat. No. 5,350,723, U.S. Pat. No. 5,425,872, U.S. Pat. No. 5,625,087, U.S. Pat. No. 5,883,204, U.S. Pat. No. 5,919,983, U.S. Pat. No. 5,783,512, WO 99/15534, and U.S. Ser. No. 09/251,664, filed Feb. 17, 1999 (WO99/42467).

Combinations of neutral Lewis acids, especially the combination of a trialkylaluminum compound having from 1 to 4 carbons in each alkyl group and a halogenated tri (hydrocarbyl)boron compound having from 1 to 20 carbons in each hydrocarbyl group, especially tris (pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex: tris(pentafluoro-phenylborane: alumoxane are from 1:1:1 to 1:10:30, more preferably from 1:1:1.5 to 1:5:10.

Suitable ion forming compounds useful as cocatalysts in one embodiment of the present invention comprise a cation which is a Brønsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gallium, niobium or tantalum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*—H)_d^+(A)^{d-}$$

wherein:
L* is a neutral Lewis base;
$(L^*—H)^+$ is a conjugate Brønsted acid of L*;
$A^{d-}$ is a noncoordinating, compatible anion having a charge of d−, and
d is an integer from 1 to 3.

More preferably $A^{d-}$ corresponds to the formula: $[M'Q_4]^-$;
wherein:
M' is boron or aluminum in the +3 formal oxidation state; and
Q independently each occurrence is selected from hydride, dialkylamido, halide, hydrocarbyl, hydrocarbyloxide, halo-substituted hydrocarbyl, halo-substituted hydrocarbyloxy, and halo- substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is $A^-$. Activating cocatalysts comprising boron which are particularly useful in the preparation of catalysts of this invention may be represented by the following general formula:

$$(L^*—H)^+(BQ_4)^-;$$

wherein:
L* is as previously defined;
B is boron in a formal oxidation state of 3; and
Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl- group of up to 20 nonhydrogen atoms, with the proviso that in not more than one occasion is Q hydrocarbyl. Most preferably, Q is each occurrence a fluorinated aryl group, especially, a pentafluorophenyl group.

Preferred Lewis base salts are ammonium salts, more preferably trialkyl-ammonium- or dialkylarylammonium-salts containing one or more $C_{12-40}$ alkyl groups. The latter cocatalysts have been found to be particularly suitable for use in combination with not only the present metal complexes but other Group 4 metallocenes as well.

Illustrative, but not limiting, examples of boron compounds which may be used as an activating cocatalyst in the preparation of the improved catalysts of this invention (as well as previously known Group 4 metal catalysts) are tri-substituted ammonium salts such as:
trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(sec-butyl)ammonium tetrakis(pentafluorophenyl) borate, N,N-dimethylanilinium tetrakis(pentafluorophenyl) borate, N,N-dimethylanilinium n-butyltris(pentafluorophenyl) borate, N,N-dimethylanilinium benzyltris(pentafluorophenyl) borate,
N,N-dimethylanilinium tetrakis(4-(t-butyldimethylsilyl)-2,3,5,6-tetrafluorophenyl) borate,
N,N-dimethylanilinium tetrakis(4-(triisopropylsilyl)-2,3,5,6-tetrafluorophenyl) borate,
N,N-dimethylanilinium pentafluorophenoxytris(pentafluorophenyl) borate,
N,N-diethylanilinium tetrakis(pentafluorophenyl) borate,
N,N-dimethyl-2,4,6-trimethylanilinium tetrakis(pentafluorophenyl) borate,
dimethyltetradecylammonium tetrakis(pentafluorophenyl) borate,
dimethylhexadecylammonium tetrakis(pentafluorophenyl) borate,
dimethyloctadecylammonium tetrakis(pentafluorophenyl) borate,
methylditetradecylammonium tetrakis(pentafluorophenyl) borate,
methylditetradecylammonium (hydroxyphenyl)tris(pentafluorophenyl) borate,
methylditetradecylammonium (diethylaluminoxyphenyl)tris(pentafluorophenyl) borate,
methyldihexadecylammonium tetrakis(pentafluorophenyl) borate,
methyldihexadecylammonium (hydroxyphenyl)tris(pentafluorophenyl) borate,
methyldihexadecylammonium (diethylaluminoxyphenyl)tris(pentafluorophenyl) borate,
methyldioctadecylammonium tetrakis(pentafluorophenyl) borate,
methyldioctadecylammonium (hydroxyphenyl)tris(pentafluorophenyl) borate,
methyldioctadecylammonium (diethylaluminoxyphenyl)tris(pentafluorophenyl) borate,
methyldioctadecylammonium tetrakis(pentafluorophenyl) borate,
phenyldioctadecylammonium tetrakis(pentafluorophenyl) borate,
phenyldioctadecylammonium (hydroxyphenyl)tris(pentafluorophenyl) borate,
phenyldioctadecylammonium (diethylaluminoxyphenyl)tris(pentafluorophenyl) borate,
(2,4,6-trimethylphenyl)dioctadecylammonium tetrakis(pentafluorophenyl) borate,
(2,4,6-trimethylphenyl)dioctadecylammonium (hydroxyphenyl)tris(pentafluorophenyl)-borate,
(2,4,6-trimethylphenyl)dioctadecylammonium (diethylaluminoxyphenyl) tris(pentafluorophenyl)borate,
(2,4,6-trifluorophenyl)dioctadecylammonium tetrakis(pentafluorophenyl)borate,
(2,4,6-trifluorophenyl)dioctadecylammonium (hydroxyphenyl)tris(pentafluorophenyl)-borate,
(2,4,6-trifluorophenyl)dioctadecylammonium (diethylaluminoxyphenyl)tris-(pentafluoro-phenyl) borate,
(pentafluorophenyl)dioctadecylammonium tetrakis(pentafluorophenyl)borate,
(pentafluorophenyl)dioctadecylammonium (hydroxyphenyl)tris(pentafluorophenyl)-borate,
(pentafluorophenyl)dioctadecylammonium (diethylaluminoxyphenyl)tris(pentafluoro-phenyl) borate,
(pentafluoromethylphenyl)dioctadecylammonium tetrakis(pentafluorophenyl)borate,
(p-trifluoromethylphenyl)dioctadecylammonium (hydroxyphenyl)tris(pentafluoro-phenyl) borate,
(p-trifluoromethylphenyl)dioctadecylammonium (diethylaluminoxyphenyl)tris(pentafluorophenyl) borate,
p-nitrophenyldioctadecylammonium tetrakis(pentafluorophenyl)borate,
p-nitrophenyldioctadecylammonium (hydroxyphenyl)tris(pentafluorophenyl) borate,
p-nitrophenyldioctadecylammonium (diethylaluminoxyphenyl)tris(pentafluorophenyl) borate,
and mixtures of the foregoing,
  dialkyl ammonium salts such as:
di-(i-propyl)ammonium tetrakis(pentafluorophenyl) borate,
methyloctadecylammonium tetrakis(pentafluorophenyl) borate,
methyloctadodecylammonium tetrakis(pentafluorophenyl) borate, and
dioctadecylammonium tetrakis(pentafluorophenyl) borate;
  tri-substituted phosphonium salts such as:
triphenylphosphonium tetrakis(pentafluorophenyl) borate,
methyldioctadecylphosphonium tetrakis(pentafluorophenyl) borate, and
tri(2,6-dimethylphenyl)phosphonium tetrakis(pentafluorophenyl) borate;
  di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate;
  di-substituted sulfonium salts such as:
di(o-tolyl)sulfonium tetrakis(pentafluorophenyl) borate, and
methylcotadecylsulfonium tetrakis(pentafluorophenyl) borate.

Preferred trialkylammonium cations are methyldioctadecylammonium and dimethyloctadecylammonium. The use of the above Brønsted acid salts as activating cocatalysts for addition polymerization catalysts is known in the art, having been disclosed in U.S. Pat. Nos. 5,064,802, 5,919,983, 5,783,512 and elsewhere. Preferred dialkylarylammonium cations are fluorophenyldioctadecylammonium-, perfluorophenyldioctacecylammonium- and p-trifluoromethylphenyldi(octadecyl)ammonium cations. It should be noted that certain of the cocatalysts, especially those containing a hydroxyphenyl ligand in the borate anion, may require the addition of a Lewis acid, especially a trialkylaluminum compound, to the polymerization mixture or the catalyst composition, in order to form the active catalyst composition.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:
  $Ox^{e+}$ is a cationic oxidizing agent having a charge of e+;
  e is an integer from 1 to 3; and
  $A^{d-}$ and d are as previously defined.

Examples of cationic oxidizing agents include: ferrocenium, hydrocarbyl-substituted ferrocenium, $Ag^+$ or $Pb^{+2}$. Preferred embodiments of $A^{d-}$ are those anions previously defined with respect to the Brønsted acid containing activating cocatalysts, especially tetrakis(pentafluorophenyl)borate. The use of the above salts as activating cocatalysts for addition polymerization catalysts is known in the art, having been disclosed in U.S. Pat. No. 5,321,106.

Another suitable ion forming, activating cocatalyst comprises a compound which is a salt of a carbenium ion and a noncoordinating, compatible anion represented by the formula:

⁺A⁻ wherein:

©⁺ is a $C_{1-20}$ carbenium ion; and

A⁻ is as previously defined. A preferred carbenium ion is the trityl cation, that is triphenylmethylium. The use of the above carbenium salts as activating cocatalysts for addition polymerization catalysts is known in the art, having been disclosed in U.S. Pat. No. 5,350,723.

A further suitable ion forming, activating cocatalyst comprises a compound which is a salt of a silylium ion and a noncoordinating, compatible anion represented by the formula:

$R^3_3Si(X')_q{}^+A^-$ wherein:

$R^3$ is $C_{1-10}$ hydrocarbyl, and X', q and A⁻ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula: $(A^{1+a^1})_{b^1}(Z^1J^1_{j^1})^{-c^1}{}_{d^1}$, wherein:

$A^1$ is a cation of charge $+a^1$, $Z^1$ is an anion group of from 1 to 50, preferably 1 to 30 atoms, not counting hydrogen atoms, further containing two or more Lewis base sites;

$J^1$ independently each occurrence is a Lewis acid coordinated to at least one Lewis base site of $Z^1$, and optionally two or more such $J^1$ groups may be joined together in a moiety having multiple Lewis acidic functionality, $j^1$ is a number from 2 to 12 and $a^1$, $b^1$, $c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

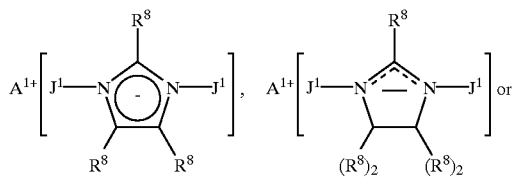

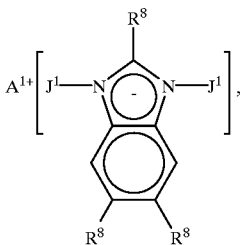

wherein:

$A^{1+}$ is a monovalent cation as previously defined, and preferably is a trihydrocarbyl ammonium cation, containing one or two $C_{10-40}$ alkyl groups, especially the methylbis (tetradecyl)ammonium- or methylbis(octadecyl) ammonium-cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris (pentafluorophenyl)aluminane.

Examples of these catalyst activators include the trihydrocarbylammonium-, especially, methylbis(tetradecyl) ammonium- or methylbis(octadecyl)ammonium- salts of:
bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide, bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide, bis(tris(pentafluorophenyl)borane)-4,5-bis(undecyl)imidazolinide,
bis(tris(pentafluorophenyl)borane)-4,5-bis(heptadecyl)imidazolinide,
bis(tris-(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide, bis(tris(pentafluorophenyl)alumane)-4,5-bis(undecyl)imidazolide,
bis(tris(pentafluorophenyl)alumane)-4,5-bis(heptadecyl)imidazolide,
bis(tris(pentafluorophenyl)alumane)imidazolinide,
bis(tris(pentafluorophenyl)alumane)-2-undecylimidazolinide,
bis(tris(pentafluorophenyl)alumane)-2-heptadecylimidazolinide,
bis(tris(pentafluorophenyl)alumane)4,5-bis(undecyl)imidazolinide,
bis(tris(pentafluorophenyl)alumane)-4,5-bis(heptadecyl)imidazolinide,
bis(tris(pentafluorophenyl)alumane)-5,6-dimethylbenzimidazolide, and
bis(tris(pentafluorophenyl)alumane)-5,6-bis(undecyl)benzimidazolide.

A further class of suitable activating cocatalysts include cationic Group 13 salts corresponding to the formula:

$$[M''Q^1{}_2L'_{l'}]^+(Ar^f{}_3M'Q^2)^-$$

wherein:

M" is aluminum, gallium, or indium;

M' is boron or aluminum;

$Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;

$Q^2$ is an alkyl group, optionally substituted with one or more cycloalkyl or aryl groups, said $Q^2$ having from 1 to 30 carbons;

L' is a monodentate or polydentate Lewis base, preferably L' is reversibly coordinated to the metal complex such that it may be displaced by an olefin monomer, more preferably L' is a monodentate Lewis base;

l' is a number greater than zero indicating the number of Lewis base moieties, L', and $Ar^f$ independently each occurrence is an anionic ligand group; preferably $Ar^f$ is selected from the group consisting of halide, $C_{1-20}$ halohydrocarbyl, and $Q^1$ ligand groups, more preferably $Ar^f$ is a fluorinated hydrocarbyl moiety of from 1 to 30 carbon atoms, most preferably $Ar^f$ is a fluorinated aromatic hydrocarbyl moiety of from 6 to 30 carbon atoms, and most highly preferably $Ar^f$ is a perfluorinated aromatic hydrocarbyl moiety of from 6 to 30 carbon atoms.

Examples of the foregoing Group 13 metal salts are alumicinium tris(fluoroaryl)borates or gallicinium tris (fluoroaryl)borates corresponding to the formula: $[M''Q^1{}_2L'_{1}]^+(Ar^f{}_3BQ^2)^-$, wherein M" is aluminum or gallium; $Q^1$ is $C_{1-20}$ hydrocarbyl, preferably $C_{1-8}$ alkyl; $Ar^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

The foregoing activating cocatalysts may also be used in combination. An especially preferred combination is a mixture of a tri(hydrocarbyl)aluminum or tri(hydrocarbyl) borane compound having from 1 to 4 carbons in each hydrocarbyl group or an ammonium borate with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. The term "overnight", if used, refers to a time of approximately 16–18 hours, the term "room temperature", refers to a temperature of about 20–25° C., and the term "mixed alkanes" refers to a commercially obtained mixture of $C_{6-8}$ aliphatic hydrocarbons available under the trade designation Isopar E®, from Exxon Chemicals Inc.

$^1$H (300 MHz) and $^{13}$C NMR (75 MHz) spectra were recorded on a Varian XL-300 spectrometer. $^1$H and $^{13}$C NMR spectra are referenced to the residual solvent peaks and are reported in ppm relative to tetramethylsilane. All J values are given in Hz. Tetrahydrofuran (THF), diethylether, toluene, and hexane were used following passage through double columns charged with activated alumina and a purifying catalyst (Q-5® available from Englehardt Chemicals Inc.) The compounds $BCl_3$-$SMe_2$, $BBr_3$-$SMe_2$, $B(NMe_2)_3$, n-BuLi were all used as purchased from Aldrich. The compound $TiCl_3(THF)_3$ was prepared as described in the literature. All syntheses were performed under dry nitrogen or argon atmospheres using a combination of glove box and high vacuum techniques.

Example 1 rac-isoindolenidoborane-bis-$\eta^5$-(2-methyl-4-phenylinden-1-yl)zirconium $\eta^4$-1,4-diphenyl-1,3-butadiene

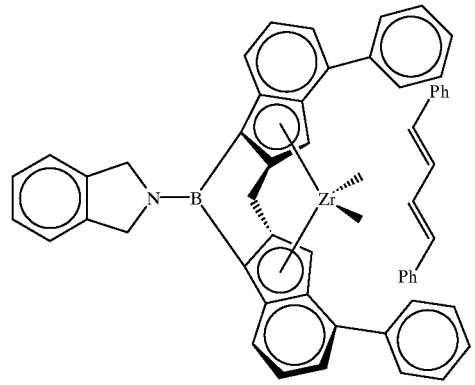

A. Synthesis of BrB(2-methyl-4-phenyl-indene)$_2$

To 40 mL toluene was added 0.220 mL BBr$_3$ (2.32 mmol). To this solution was added dropwise a solution of 1.010 g of Mg(2-Me-4-Ph-indenide)$_2$ (2.32 mmol) in about 10 mL toluene. Addition took approximately 10 minutes. Five mL fresh toluene was used to rinse the vial which had contained the Mg(2-Me-4-Ph-indenide)$_2$ solution, which was combined with the reaction contents. The reaction stirred for 1.5 hours at room temperature. The desired product is obtained as a mixture of two diastereomers. The diastereomers may be separated by triturating with hexane several times with complete drying between each application to remove residual toluene, washing with cold hexane and drying, and repeated extraction with hexane.

B. Synthesis of isoindoleno bis(2-methyl-4-phenyl-indene) borane 0.024 g (0.14 mmol) of BrB(2-Me-4-Ph-indenide)$_2$ was dissolved into 20 mL Et$_2$O. Lithium isoindolenide (LiCl) (made from addition of 2 equivalents of BuLi to the isoindolene HCl salt, 0.070 g, 0.14 mmol) was added and the reaction stirred overnight. Et$_2$O was removed in vacuo and the product as a mixture of two diastereoisomers obtained by drying.

$^1$H NMR (C$_6$D$_6$, δ): 7.7–6.4 (multiplets, aromatic and vinyl, 22 H); 4.72, 4.16, 3.52 (AB quartet, d, and d respectively; C$_6$H$_4$(CH$_2$)$_2$, 4H total); 3.90, 2.76 (s each, BCH, 2H total); 2.04, 1.88 (s each, CH$_3$, 6H total).

C. Synthesis of rac-isoindoleno bis(2-methyl-4-phenyl-indenyl) borane zirconium(η$^4$-1,4-diphenyl-1,3-butadiene)

The above mixture of isoindoleno bis(2-methyl-4-phenyl-indene) borane diastereoisomers (1.122 g, 2.08 mmol) was dissolved into 40 mL toluene followed by addition of 8.321 mL of a 0.5 M solution of KN(TMS)$_2$ (toluene solution, 4.16 mmol) via syringe. After 45 minutes the toluene was concentrated to approximately 5 mL and 20 to 30 mL hexane added to complete the precipitate formation. The product, K$_2$[isoindoleneB(2-Me-4-Ph-indenide)$_2$], was collected as a yellow solid by filtration and washed with 15 mL hexane and dried under vacuum. 0.269 g Of this dianion (0.44 mmol) was added to a toluene solution of Zr(PEt$_3$)$_2$Cl$_2$(1,4-diphenyl-1,3-butadiene) (30 mL toluene, 0.264 g, 0.44 mmol) using 10 mL fresh toluene to aid in the transfer. The reaction mixture was stirred overnight. Toluene was removed in vacuo and the product extracted from the salts with hexane (total of about 175 mL hexane used before the filterate was colorless). The combined filtrate was taken to dryness under vacuum. The red product, rac-isoindoleno bis(2-methyl-4-phenyl-indenyl) borane zirconium(η$^4$-1,4-diphenyl-1,3-butadiene), was isolated as only the racemic isomer in 41.6 percent yield (0.152 g).

Example 2

Synthesis of bis(4-dimethylaminophenyl)amido bis (2-methyl-4-phenyl-indenyl) borane zirconium(η$^4$-1,4-diphenyl-1,3-butadiene)

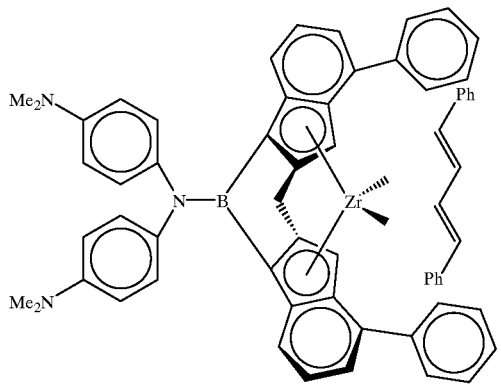

A. Synthesis of bis(4-dimethylaminophenyl)amido bis(2-methyl-4-phenyl-indene) borane:

To a toluene (30 to 40 mL) solution of BrB(2-methyl-4-phenyl-indene)$_2$ (Example 1A, 0.900 g, 1.80 mmol) was added 0.250 mL of NEt$_3$ (1.80 mmol) with stirring. This was followed by the addition of 0.458 g of (p-Me$_2$NC$_6$H$_4$)$_2$NH (1.80 mmol). The reaction was stirred at room temperature for several days (minimum stir time is 4 hours) followed by filtration through a diatomaceous earth pad. The insolubles are washed with 10 mL fresh toluene. The combined filtrate was taken to dryness in vacuo and the product dried. The product was triturated with hexane and filtered to give an olive colored powder after drying in dynamic vacuum.

$^1$H NMR (C$_6$D$_6$, 50° δ):

B. Synthesis of bis(4-dimethylaminophenyl)amido bis(2-methyl-4-phenyl-indenyl) borane zirconium(θ$^4$-1,4-diphenyl-1,3-butadiene):

To 40 mL of toluene was added 1.067 g of (p-Me$_2$NC$_6$H$_4$)$_2$NB(2-Me-4-Ph-indene)$_2$, (1.58 mmol) followed by the addition 2 equivalents of KN(TMS)$_2$ (0.630 g, 3.16 mmol). The reaction was stirred for 2 hours. The product, K$_2$[(p-Me$_2$NC$_6$H$_4$)$_2$NB(2-Me-4-Ph-indenyl)$_2$], was isolated by filtration and washed with hexane (2×15 mL) and dried in dynamic vacuum to give a yellow orange solid. 0.425 g (0.57 mmol) Of this salt was added with stirring to a toluene (30 mL) solution of Zr(PEt$_3$)$_2$Cl$_2$(1,4-diphenyl-1,3-butadiene) (0.342 g, 0.57 mmol). After 4 hours at room temperature a 2 mL portion was collected and taken to dryness in vacuo, and the product extracted with 1 mL C$_6$D$_6$ and filtered into an NMR tube. $^1$H NMR spectra indicated that only the rac isomer was obtained. The NMR sample was reclaimed and the toluene removed in dynamic vacuum from the reaction mixture. The product was triturated with hexane twice with drying between application followed by extraction with hexane (200 mL) and filtration. The hexane was concentrated to approximately 5 mL in vacuo and the product, (p-Me$_2$NC$_6$H$_4$)$_2$NB(2-Me-4-Ph-indenide)$_2$Zr(1,4-diphenyl-1,3-butadiene), was collected by filtration and drying in dynamic vacuum.

$^1$H NMR (C$_6$D$_6$, 50° δ):

Example 3

Synthesis of N-methyl-piperazino bis(2-methyl4-phenyl-indenyl) borane zirconium(η$^4$-1,4-diphenyl-1,3-butadiene)

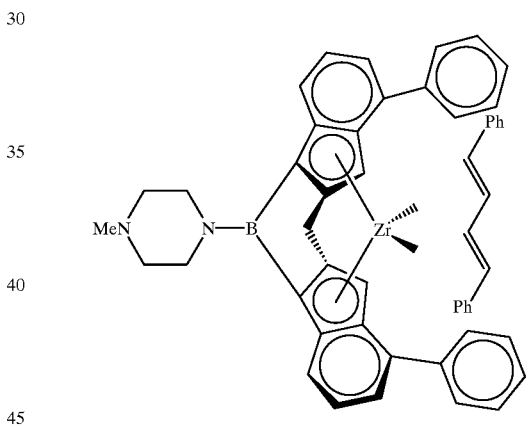

A. Synthesis of N-methyl-piperazino bis(2-methyl-4-phenyl-indene) borane:

To a toluene (30 mL) solution of BrB(2-methyl-4-phenyl-indene)$_2$ (example 2A, 0.750 g, 1.50 mmol) was added 0.209 mL of NEt$_3$ (1.50 mmol) with stirring. This was followed by the addition of 0.166 mL of N-methylpiperazine (1.50 mmol). The reaction was stirred at room temperature for 1.5 hours. The solvent was removed under vacuum and extracted with a 50/50 mixture of hexane/toluene (2×15 mL) and filtered through a pad of diatomaceous earth. The combined filtrate was taken to dryness in vacuo and the product dried. The product was triturated with hexane (10 mL, 4 times with drying between each application) and dried in dynamic vacuum.

B. Synthesis of N-methyl-piperazino bis(2-methyl-4-phenyl-indenyl) borane zirconium(η$^4$-1,4-diphenyl-1,3-butadiene)

To 40 mLs of toluene was added 0.503 g of MeN(CH$_2$CH$_2$)$_2$NB(2-Me-4-Ph-indene)$_2$, (0.97 mmol) followed by the addition 2 equivalents of KN(TMS)2 (0.385 g, 1.93 mmol). The reaction was stirred for 1.5 hours. The toluene was reduced in volume to approximately 10 to 15 mL and the product precipitated by addition of 30 mL of hexane. The product, K$_2$[MeN(CH$_2$CH$_2$)$_2$NB(2-Me-4-Ph-indenyl)$_2$], was isolated by filtration and washed with hexane (2×15 mL) and dried in dynamic vacuum to give a yellow orange solid. 0.418 g (0.70 mmol) Of this salt was added with stirring to a toluene (30 mL) solution of Zr(PEt$_3$)$_2$Cl$_2$(1,4-diphenyl-1,3-butadiene) (0.424 g, 0.70 mmol). After several days at room temperature the toluene was removed under dynamic vacuum from the reaction mixture. The product was triturated with hexane twice with drying between applications followed by extraction with hexane (70 mL) and filtration. The hexane was removed in vacuo and the product, MeN(CH$_2$CH$_2$)$_2$NB(2-Me-4-Ph-indenide)$_2$Zr(1,4-diphenyl-1,3-butadiene), was isolated after recrystallizing from cold hexane, decanting the mother liquor and drying in dynamic vacuum.

Example 4

Synthesis of morphlino bis(2-methyl-4-phenyl-indenyl) borane zirconium($\eta^4$-1,4-diphenyl-1,3-butadiene)

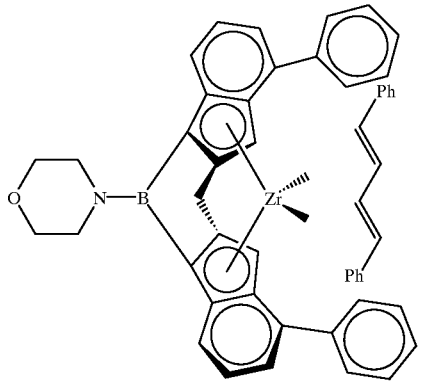

A. Synthesis of morphlino bis(2-methyl-4-phenyl-indene) borane:

To a toluene (25 ml) solution of BrB(2-Me-4-Ph-indenide)$_2$ (Example 2A, 0.750 g, 1.5 mmol)) was added triethyl amine (0.151 g, 1.5 mmol), then morpholine (0.130 g, 1.5 mmol). This mixture was stirred overnight at ambient temperature. The solvent was removed in vacuo, a hexane/toluene mixture was added to the residue and the white solid removed by filtration. Evaporation of the solvent from the filtered solution gave the borane as a white solid (0.17 g, 22 percent).

$^1$H NMR (C$_6$D$_6$, δ): (two diastereoisomers observed) 7.6–7.1 (multiplets, aromatic, 16H); 3.5 (multiplet, indene methylenes, 4H), 3.2 (multiplet, morpholine methylenes, 8H), 2.0 (s, CH$_3$, 3H), 1.9 (s, CH$_3$, 3H).

B. Synthesis of morphlino bis(2-methyl-4-phenyl-indenyl) borane zirconium($\eta^4$-1,4-diphenyl-1,3-butadiene)

To a solution of morpholino bis(2-methyl-4-phenyl-indene) borane (0.17 g, 0.33 mmol) was in 20 ml THF was added 0.14 g KN(TMS)$_2$ (0.70 mmol). This mixture was stirred overnight at ambient temperature. The solvent was removed in vacuo, hexane was added, the mixture stirred and the solvent again removed to give K$_2$[(morpholino)B (2-Me-4-Ph-indenide)$_2$] as an orange solid. 0.20 g Of this dianion (0.34 mmol) was added to a toluene solution of Zr(PEt$_3$)$_2$Cl$_2$(1,4-diphenyl-1,3-butadiene) (20 ml toluene, 0.207 g, 0.34 mmol) using 5 ml fresh toluene to aid in the transfer. This mixture was stirred for two days at ambient temperature. The resulting mixture was concentrated, cooled, and filtered (to remove KCl). The remaining toluene was removed in vacuo and hexane added to precipitate the crude product. This material was further purified by recrystallization in toluene/hexane to afford rac-morpholino bis(2-methyl-4-phenyl-indenyl) borane zirconium($\eta^4$-1,4-diphenyl-1,3-butadiene) as a red solid.

$^1$H NMR (C$_6$D$_6$, δ): 7.5–6.7 (multiplets, aromatic, 26 H), 5.5 (s, indenyl H, 2H), 3.5 (multiplet, morpholino CH$_2$, 4H), 3.5 (multiplet, vinyl H, 2H), 3.3 (multiplet, morpholino CH$_2$, 4H), 1.8 (multiplet, vinyl H, 2H), 1.7 (s, CH$_3$, 3H).

Example 5

Synthesis of diisopropylamido bis(2-methyl-4-{2-methylphenyl}-indenyl) borane zirconium($\eta^4$-1,4-diphenyl-1,3-butadiene);

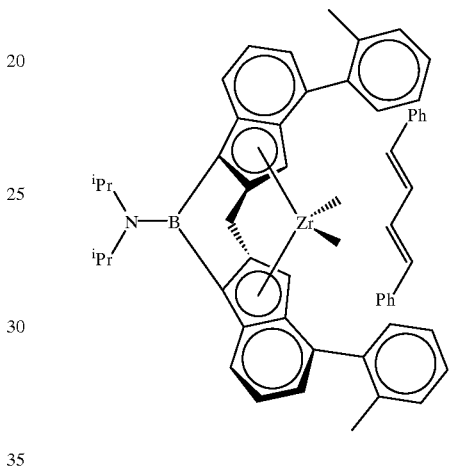

A. Synthesis of BrB(2-methyl-4-{2-methylphenyl}-indene)$_2$:

To 20 mL toluene was added 0.200 mL BBr$_3$ (2.12 mmol). To this solution was added dropwise a solution of 0.980 g of Mg(2-methyl-4-{2-methylphenyl}-indenide)$_2$ (2.12 mmol) in about 20 mL toluene. Addition took approximately 10 minutes. Five mL fresh toluene was used to rinse the vial which had contained the Mg(2-methyl-4-{2-methylphenyl}-indenide)$_2$ solution, which was combined with the reaction contents. The reaction stirred overnight at room temperature. Toluene solvent was removed in vacuo and the product was triturated with hexane, extracted with hexane (3×20 mL) and filtered. The combined filtrate was taken to dryness to give the product as a glassy pale yellow solid.

$^1$H NMR (C$_6$D$_6$, 50° δ):

B. Synthesis of diisopropylamido bis(2-methyl-4-{2-methylphenyl}-indene) borane:

To a toluene (20 mL)solution was dissolved 0.360 g of BrB(2-methyl-4-{2-methylphenyl}-indene)$_2$ (0.68 mmol) followed by 95 μL of HN$^i$Pr$_2$ (0.68 mmol) with stirring. To this mixture was added 95 μL of NEt$_3$. After stirring for 3 hours the yellow color of the initial reaction product had faded to a colorless salt suspension. The toluene was removed in vacuo and the product triturated with hexane twice, drying under vacuum between each application. The product was extracted with hexane, filtered, and washed with an additional 5 mL hexane. The combined filtrate was taken to dryness in vacuo to give the product as a glassy white solid.

$^1$H NMR (C$_6$D$_6$, 50° δ):

C. Synthesis of diisopropylamido bis(2-methyl-4-{2-methylphenyl}-indenyl) borane zirconium($\eta^4$-1,4-diphenyl-1,3-butadiene)

0.121 g of KN(TMS)$_2$ (0.60 mmol) was added with stirring to a toluene (20 mL) solution of $^i$Pr$_2$NB(2-Me-4-{2-MePh}-indene)$_2$ (0.166 g, 0.30 mmol), using 10 mL toluene to aid in the transfer. The reaction mixture was stirred at room temperature for 1.5 hours and the toluene was concentrated to a few mL. Hexane (about 25 mL) was added causing the yellow product to precipitate. The product was collected by filtration and washed with 10 mL hexane and dried under dynamic vacuum. 0.165 g of this potassium salt (0.26 mmol) was added to a toluene (20 mL) solution of Zr(PEt$_3$)$_2$Cl$_2$(1,4-diphenyl-1,3-butadiene) (0.159g, 0.26 mmol), using 30 mL toluene to aid in the transfer. The reaction was allowed to stir overnight. The solvent was removed in vacuo and the product dried. The product was extracted with hexane, filtered, and the filtrate taken to dryness. Hexane (10 mL) was added and the mixture was stirred at room temperature for 2 hours, after which time the product formed as a solid due to the break up of a toluene solvate. The red powdered product, $^i$Pr$_2$NB(2-Me-4-{2-MePh}-indene)$_2$Zr(1,4-diphenyl-1,3-butadiene), was washed with hexane, isolated by filtration, and dried in vacuo.

$^1$H NMR (C$_6$D$_6$, 70° δ):

Example 6

Synthesis of bis(4-dimethylaminophenyl)amido bis(2-methyl-4-{2-methylphenyl}-indenyl)borane zirconium($\eta^4$-1,4-diphenyl-1,3-butadiene):

A. Synthesis of bis(4-dimethylaminophenyl)amido bis(2-methyl-4-{2-methylphenyl}-indene) borane:

To a toluene (30 mL) solution of BrB(2-methyl-4-{2-methylphenyl}-indene)$_2$ (Example 5A, 0.877 g, 1.66 mmol) was added 0.231 mL of triethylamine (1.66 mmol) with stirring. This was followed by the addition of 0.423 g of (p-Me$_2$NC$_6$H$_4$)$_2$NH (1.66 mmol). The reaction was stirred at room temperature overnight followed by filtration through a diatomaceous earth pad. The insolubles are washed with 10 mL fresh toluene. The combined filtrate was taken to dryness in vacuo and the product dried. The product was triturated with hexane, filtered, and washed with 10 mL fresh hexane to give an olive colored powder after drying in dynamic vacuum.

$^1$H NMR (C$_6$D$_6$, 50° d):

B. Synthesis of bis(4-dimethylaminophenyl)amido bis(2-methyl-4-{2-methylphenyl}-indenyl) borane zirconium($\eta^4$-1,4-diphenyl-1,3-butadiene):

To 20 mLs of toluene was added 0.573 g of (p-Me$_2$NC6H$_4$)$_2$NB(2-Me-4-{2-methylphenyl}-indene)2, (0.81 mmol) followed by the addition 2 equivalents of KN(TMS)$_2$ (0.325 g, 1.63 mmol) in 15 mL toluene. The reaction was stirred for 2.5 hours. The product, K$_2$[(p-Me$_2$NC$_6$H$_4$)$_2$NB(2-Me-4-{2-methylphenyl}-indenyl)$_2$], was isolated by filtration and washed with hexane (2×15 mL) and dried in dynamic vacuum to give a yellow orange solid. 0.657 g (0.84 mmol) Of this salt was added, using 20 mL toluene to aid in the transfer, with stirring to a toluene (20 mL) solution of Zr(PEt$_3$)$_2$Cl$_2$(1,4-diphenyl-1,3-butadiene) (0.509 g, 0.84 mmol). After stirring overnight at room temperature the toluene was removed in dynamic vacuum from the reaction mixture. The product was triturated with hexane twice with drying between application followed by initial extraction with hexane (200 mL) followed by an approximate 50/50 hexane toluene mixture and filtered. The solvent was removed in vacuo. 40 mLs Of hexane was added with warming and toluene added slowly over 30 minutes until everything was dissolved. The solution was placed in the freezer overnight to recrystallize. The recrystallized mixture was filtered and the solvent was removed under reduced pressure and triturated with hexane and dried. Finally, the product was slurried into 15 mL hexane and filtered, giving 0.370 g of the product, (p-Me$_2$NC$_6$H$_4$)$_2$NB(2-Me-4-{2-methylphenyl}-indenide)$_2$Zr(1,4-diphenyl-1,3-butadiene), as a red solid after drying.

$^1$H NMR (C$_6$D$_6$, 65° δ):

Polymerization Details

Isopar™ E and 1-octene were purified by sparging with purified nitrogen followed by passage through columns containing alumina (A-2, available from LaRoche Inc.) and Q5 reactant (available from Englehard Chemicals Inc.) at 50 psig (340 kPa) using a purified nitrogen pad. All transfers of solvents and solutions described below were accomplished using a gaseous pad of dry, purified nitrogen or argon. Gaseous feeds to the reactor were purified by passage through columns of A-204 alumina (available from LaRoche Inc.) and Q5 reactant. The aluminas were previously activated by treatment at 375° C. with nitrogen. Q5 reactant was activated by treatment at 200° C. with 5 percent hydrogen in nitrogen.

Batch reactor polymerizations were conducted in a two liter Zipperclave reactor equipped with circulating water cooling (used for the 70° and 85° C. polymerizations) or steam heating (used for higher temperature polymerizations) and a bottom drain valve. Pressures, temperatures and block valves were computer monitored and controlled. Isopar™ E solvent and propylene (C$_3$) were measured in a solvent shot tank fitted with an injection system for adding the contents to the reactor. The contents of the reactor were stirred at 1000 rpm. Hydrogen was added by differential expansion (about δ20 psi, 140 kPa) from a 75 mL shot tank. The contents of the reactor were then heated to the desired run temperature of 70° C. The catalyst (0.4 μmole) and cocatalyst (either a mixture of methylbis(tetradecyl)ammonium- and methylbis(octadecyl)ammonium- salts of bis(tris (pentafluorophenyl)alumane)-2-undecylimidazolide (AAU) or MAO) as 0.0050 M toluene solutions were combined in the desired ratio (a molar ratio of 1:1 for AAU and 1:100 for MAO) in the glove box and transferred from the glove box to the catalyst shot tank through 1/16 in (0.16 cm) tubing using toluene to aid in the transfer. The catalyst tank was then pressurized to approximately 600 psig (4.1 MPa) using nitrogen. After the contents of the reactor had stabilized at the desired run temperature, the catalyst was injected into the reactor via a dip tube. The temperature was maintained throughout the run, with typical exotherms of 1 to 3° C. being observed. The run times varied from 5 to 30 minutes depending on activity. Additional injections of catalyst composition prepared and injected in the same manner were employed where indicated. The contents of the reactor were then expelled into a 4 liter nitrogen purged vessel. Volatile materials were removed from the polymers in a vacuum oven that gradually heated the polymer to 140° C. overnight and cooled the same to at least 50° C. prior to removal from the oven. After completion of the polymerization, the reactor was washed with 1200 mL of Isopar™ E solvent at 150° C. before reuse. Polymer melting points were determined using differential scanning calorimetry. Results are contained in Table 1.

TABLE 1

| Run | Cat. | Cocat. | Solvent (g) | $C_3$ (g) | $H_2$ ($\Delta$ psi*) | Yield (g) | Efficiency (gpol./μg Zr) | $T_m$ (°C.) | MW |
|---|---|---|---|---|---|---|---|---|---|
| 1 | Ex. 2[1] | AAU | 625 | 150 | 37.5 | 1.7 | 0.046 | 155.8 | 218,000 |
| 2 | " | MAO | 625 | 150 | 37.5 | 27.0 | 0.740 | 151.3 | 193,000 |
| 3 | " | AAU | 641 | 277 | 10 | 0.5 | 0.014 | 155.5 | 449,000 |
| 4 | " | MAO | 641 | 277 | 10 | 39.2 | 1.070 | 150.9 | 362,000 |
| 5 | Ex. 6[2] | AAU | 625 | 150 | 37.5 | 0.4 | 0.011 | — | — |
| 6 | " | MAO | 625 | 150 | 37.5 | 22.9 | 0.628 | 150.7 | 153,000 |
| 7 | " | MAO | 641 | 277 | 10 | 23.8 | 0.652 | 150.0 | — |
| 8 | " | AAU | 641 | 277 | 10 | 91.4 | 2.505 | 152.9 | 343,000 |
| 9 | Ex. 4[3] | AAU | 625 | 150 | 37.5 | 0.4 | 0.011 | — | — |
| 10 | " | MAO | 625 | 150 | 37.5 | 6.6 | 0.181 | — | — |
| 11 | " | AAU | 641 | 277 | 10 | 1.8 | 0.049 | 156.2 | — |
| 12 | " | MAO | 641 | 277 | 10 | 5.9 | 0.162 | 151.7 | — |

*37.5 psi = 255 kPa, 10 psi = 70 kPa
[1] rac-bis(4-dimethylaminophenyl)amido bis(2-methyl-4-phenylinden-1-yl) borane zirconium ($\eta^4$-1,4-diphenyl-1,3-butadiene)
[2] rac-bis(4-dimethylaminophenyl)amido bis(2-methyl-4-{2-methylphenyl}inden-1-yl) borane zirconium($\eta^4$-1,4-diphenyl-1,3-butadiene)
[3] rac-morpholino bis(2-methyl-4-phenyl-inden-1-yl)borane zirconium($\eta^4$-1,4-diphenyl-1,3-butadiene)

What is claimed is:

1. A process for forming a bridged Group 4 transition metal complex corresponding to the formula:

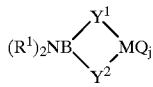

Formula 1 wherein:

M is a Group 4 metal in the +2, +3 or +4 formal oxidation state;

$Y^1$ and $Y^2$ are independently anionic, cyclic or non-cyclic, π-bonded groups, Q, independently each occurrence, is a neutral, anionic or dianionic ligand group, said Q having up to 50 atoms not counting hydrogen;

j is an integer from 1 to 4, selected with respect to the oxidation state of M and the electronic nature of Q to provide overall charge balance to the compound;

$R^1$ is independently each occurrence hydrogen, a hydrocarbyl group, a tri(hydrocarbyl)silyl group, or a tri (hydrocarbyl)silylhydrocarbyl group, or one of the foregoing multiatomic groups further substituted with one or more di(hydrocarbyl)amino- or hydrocarbyloxy- groups, said $R^1$ group containing up to 50 atoms not counting hydrogen, and optionally both $R^1$ groups may be joined together, optionally by means of one or more divalent bridging group moieties derived from the foregoing di(hydrocarbyl)amino- or hydrocarbyloxy- substituent groups, thereby forming a dianionic ligand group, the steps of the process comprising:

(1) contacting a boron trihalide with a magnesium dianionic salt corresponding to the formula $Mg(Y^1H)(Y^2H)$, wherein $Y^1$ and $Y^2$ are as previously defined to prepare a metal complex according to the formula:

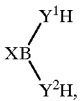

Formula 2 wherein X is halide;

(2) aminating the boron bridging atom thereby forming a compound of Formula 3,

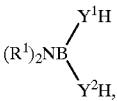

Formula 3 wherein $R^1$ is as previously defined, (3) deprotonating the product of step (2) of Formula 3 by contact with a deprotonating agent; and (4) contacting the product of step (3) with a transition metal salt of the formula $MY^3{}_y(LB)_b$, wherein M is as previously defined;

$Y^3$ is Q or a leaving group;

y is an integer from 0 to 4 selected to provide charge balance in the transition metal salt;

LB is a Lewis base compound; and b is an integer from 0 to 3.

2. The process of claim 1 wherein amination of the boron bridging atom (step (2)) is accomplished by the use of an alkali metal amide- or Grignard amide- reagent of the formula $MeNR^1{}_2$, wherein Me is an alkali metal cation or Grignard cation of the formula: $MgBr^+$ or $MgCl^+$, by a secondary amine of the formula $HNR^1{}_2$, or by a mixture of a secondary amine reagent of the formula $HNR^1{}_2$ and a tertiary amine of the formula, $NR^3{}_3$, wherein $R^1$ is as previously defined and $R^3$ is $R^1$ or $C_{1-4}$ alkyl.

3. The process of claim 1 wherein in step (3) the deprotonating agent is an alkali metal bis(trialkylsilyl)amide.

4. The process of claim 1 wherein $Y^1$ and $Y^2$ are inden-1-yl, 2-methyl-4-phenylinden-1-yl, 2-methyl-4-(2-methylphenyl)inden-1-yl, 3-isopropylinden-1-yl, or 3-t-butylinden-1-yl groups.

5. The process of claim 1 wherein M is Zr.

6. A process for forming a compound corresponding to formula 2:

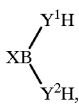

Formula 2 wherein

X is halide, and $Y^1$ and $Y^2$ are independently anionic, cyclic or non-cyclic, π-bonded groups, said process comprising contacting a boron trihalide with a magnesium dianionic salt corresponding to the formula $Mg(Y^1H)(Y^2H)$, wherein $Y^1$ and $Y^2$ are as previously defined under reaction conditions to thereby prepare the metal complex of formula 2.

7. The process of claim 6 wherein X is Br.

8. A metal complex corresponding to the formula:

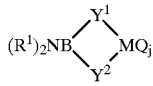

Formula 1' wherein:

M is a Group 4 metal, in the +2, +3 or +4 formal oxidation state;

$Y^1$ and $Y^2$ are independently anionic, cyclic or non-cyclic, π-bonded groups, Q is a neutral, anionic or dianionic ligand group depending on the oxidation state of M, said Q having up to 50 atoms not counting hydrogen;

j is an integer from 1 to 4, selected with respect to the oxidation state of M and the electronic nature of Q to provide overall charge balance to the compound; and $R^1$ is independently each occurrence is a substituted hydrocarbyl group, a substituted tri(hydrocarbyl)silyl group, or a substituted tri(hydrocarbyl)silylhydrocarbyl group, said group being substituted with one or more di(hydrocarbyl)amino- or hydrocarbyloxy- groups and containing up to 50 atoms not counting hydrogen, and optionally both $R^1$ groups may be joined together, optionally by means of one or more divalent bridging group moieties derived from the foregoing di(hydrocarbyl)amino- or hydrocarbyloxy- substituent groups, thereby forming a dianionic ligand group.

9. A metal complex according to claim 8 corresponding to formula 1a:

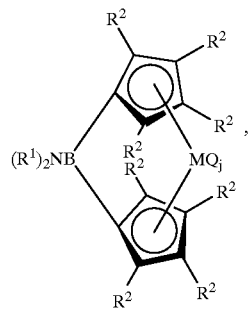

formula 1a wherein

M, Q, and j are as defined in claim 8;

$R^1$ each occurrence is 4-dimethylaminophenyl or two $R^1$ groups together with N are an isoindolenino, N-methylpiperazino, or morpholino group;

$R^2$ is hydrogen, or a hydrocarbyl, halohydrocarbyl, dihydrocarbylamino-hydrocarbyl, tri(hydrocarbylsilyl) hydrocarbyl, $Si(R^4)_3$, $N(R^4)_2$, or $OR^4$ group of up to 20 carbon or silicon atoms, and optionally two adjacent $R^2$ groups can be joined together, thereby forming a fused ring structure, and $R^4$ is independently hydrogen, a hydrocarbyl group, a trihydrocarbylsilyl group or a tri(hydrocarbyl) silylhydrocarbyl group, said $R^4$ having up to 20 atoms not counting hydrogen.

10. The complex of claim 9 wherein Q is: 1,4-diphenyl-1,3-butadiene, 1,3-pentadiene, 3-methyl-1,3-pentadiene, 2,4-hexadiene, 1-phenyl-1,3-pentadiene, 1,4-dibenzyl-1,3-butadiene, 1,4-ditolyl-1,3-butadiene, 1,4-bis(trimethylsilyl)-1,3-butadiene, or 1,4-dinaphthyl-1,3-butadiene.

11. The complex of claim 9 wherein $Y^1$ and $Y^2$ are both inden-1-yl, 2-methyl-4-phenylinden-1-yl, 2-methyl-4-(2-methylphenyl)inden-1-yl, 3-isopropylinden-1-yl, or 3-t-butylinden-1-yl groups.

* * * * *